(12) United States Patent
Salahieh et al.

(10) Patent No.: US 7,988,724 B2
(45) Date of Patent: Aug. 2, 2011

(54) SYSTEMS AND METHODS FOR DELIVERING A MEDICAL IMPLANT

(75) Inventors: Amr Salahieh, Saratoga, CA (US);
Hans F. Valencia, San Jose, CA (US);
Brian D. Brandt, San Jose, CA (US);
Claudio Argento, Los Gatos, CA (US);
Ulrich R. Haug, Campbell, CA (US);
Jean-Pierre Dueri, Stockton, CA (US);
Daniel Hildebrand, Menlo Park, CA (US);
Dwight P. Morejohn, Davis, CA (US);
Tom Saul, El Granada, CA (US)

(73) Assignee: Sadra Medical, Inc., Saratoga, CA (US)

( * ) Notice: Subject to any disclaimer, the term of this patent is extended or adjusted under 35 U.S.C. 154(b) by 489 days.

(21) Appl. No.: 11/706,549

(22) Filed: Feb. 14, 2007

(65) Prior Publication Data
US 2007/0203503 A1    Aug. 30, 2007

Related U.S. Application Data

(63) Continuation-in-part of application No. 10/982,388, filed on Nov. 5, 2004, which is a continuation-in-part of application No. 10/746,120, filed on Dec. 23, 2003, now abandoned.

(60) Provisional application No. 60/743,288, filed on Feb. 14, 2006.

(51) Int. Cl.
*A61F 2/24* (2006.01)
*A61F 2/06* (2006.01)

(52) U.S. Cl. ....................................... 623/2.12
(58) Field of Classification Search ............... 623/1.15, 623/2.11, 2.12, 2.14, 2.18, 1.24, 1.26
See application file for complete search history.

(56) References Cited

U.S. PATENT DOCUMENTS

| 3,334,629 | A |   | 8/1967  | Cohn              |
|-----------|---|---|---------|-------------------|
| 3,409,013 | A | * | 11/1968 | Berry ........ 606/1 |
| 3,540,431 | A |   | 11/1970 | Mobin-Uddin       |
| 3,628,535 | A |   | 12/1971 | Ostrowsky et al.  |
| 3,642,004 | A |   | 2/1972  | Osthagen et al.   |
| 3,657,744 | A |   | 4/1972  | Ersek             |

(Continued)

FOREIGN PATENT DOCUMENTS
CN            1338951 A        3/2002
(Continued)

OTHER PUBLICATIONS

Haug, et al; U.S. Appl. No. 11/716,123, entitled "Methods and apparatus for endovascularly replacing a heart valve," filed Mar. 9, 2007 (SLG #10012-701.301).

(Continued)

*Primary Examiner* — Alvin J. Stewart
(74) *Attorney, Agent, or Firm* — Vidas, Arrett & Steinkraus

(57) ABSTRACT

The present invention relates to apparatus and methods for endovascularly delivering and releasing a prosthesis, e.g., an aortic prosthesis, within and/or across a patient's native heart valve, referred to hereinafter as replacing the patient's heart valve. In some embodiments the delivery system comprises a plurality of first actuatable element adapted to engage a plurality of second elements in a first configuration to capture the implant within the delivery system, and wherein the plurality of first actuatable element are adapted to engage the plurality of second elements in a second configuration and to release the implant from the delivery system.

10 Claims, 76 Drawing Sheets

U.S. PATENT DOCUMENTS

| | | | |
|---|---|---|---|
| 3,671,979 A | 6/1972 | Moulopoulos | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |
| 4,291,420 A | 9/1981 | Reul | |
| 4,326,306 A | 4/1982 | Poler | |
| 4,423,809 A | 1/1984 | Mazzocco | |
| 4,425,908 A | 1/1984 | Simon | |
| 4,501,030 A | 2/1985 | Lane | |
| 4,580,568 A | 4/1986 | Gianturco | |
| 4,602,911 A | 7/1986 | Ahmadi et al. | |
| 4,610,688 A | 9/1986 | Silvestrini et al. | |
| 4,617,932 A * | 10/1986 | Kornberg | 606/108 |
| 4,647,283 A | 3/1987 | Carpentier et al. | |
| 4,648,881 A | 3/1987 | Carpentier et al. | |
| 4,655,218 A * | 4/1987 | Kulik et al. | 606/207 |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,755,181 A * | 7/1988 | Igoe | 623/2.11 |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,865,600 A * | 9/1989 | Carpentier et al. | 623/2.11 |
| 4,872,874 A | 10/1989 | Taheri | |
| 4,909,252 A | 3/1990 | Goldberger | |
| 4,917,102 A | 4/1990 | Miller et al. | |
| 4,954,126 A | 9/1990 | Wallsten | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,064,435 A | 11/1991 | Porter | |
| 5,161,547 A | 11/1992 | Tower | |
| 5,163,953 A | 11/1992 | Vince | |
| 5,209,741 A | 5/1993 | Spaeth | |
| 5,217,483 A | 6/1993 | Tower | |
| 5,258,042 A | 11/1993 | Mehta | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,425,762 A | 6/1995 | Muller | |
| 5,431,676 A | 7/1995 | Dubrul et al. | |
| 5,443,495 A | 8/1995 | Buscemi et al. | |
| 5,443,499 A | 8/1995 | Schmitt | |
| 5,476,506 A | 12/1995 | Lunn | |
| 5,476,510 A * | 12/1995 | Eberhardt et al. | 623/2.11 |
| 5,480,423 A | 1/1996 | Ravenscroft et al. | |
| 5,507,767 A | 4/1996 | Maeda et al. | |
| 5,534,007 A | 7/1996 | St. Germain et al. | |
| 5,545,133 A | 8/1996 | Burns et al. | |
| 5,545,211 A | 8/1996 | An et al. | |
| 5,549,665 A | 8/1996 | Vesely et al. | |
| 5,554,185 A | 9/1996 | Block et al. | |
| 5,571,215 A | 11/1996 | Sterman et al. | |
| 5,575,818 A | 11/1996 | Pinchuk | |
| 5,645,559 A | 7/1997 | Hachtman et al. | |
| 5,662,671 A | 9/1997 | Barbut et al. | |
| 5,667,523 A | 9/1997 | Bynon et al. | |
| 5,674,277 A | 10/1997 | Freitag | |
| 5,693,083 A | 12/1997 | Baker et al. | |
| 5,695,498 A | 12/1997 | Tower | |
| 5,713,953 A | 2/1998 | Vallana et al. | |
| 5,716,370 A | 2/1998 | Williamson, IV et al. | |
| 5,720,391 A | 2/1998 | Dohm et al. | |
| 5,733,325 A | 3/1998 | Robinson et al. | |
| 5,735,842 A | 4/1998 | Krueger et al. | |
| 5,769,812 A | 6/1998 | Stevens et al. | |
| 5,800,456 A | 9/1998 | Maeda et al. | |
| 5,800,531 A * | 9/1998 | Cosgrove et al. | 623/2.11 |
| 5,807,405 A | 9/1998 | Vanney et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,055 A | 10/1998 | Spiridigliozzi et al. | |
| 5,824,056 A | 10/1998 | Rosenberg | |
| 5,824,064 A | 10/1998 | Taheri | |
| 5,840,081 A | 11/1998 | Andersen et al. | |
| 5,843,158 A | 12/1998 | Lenker et al. | |
| 5,855,597 A | 1/1999 | Jayaraman | |
| 5,855,601 A | 1/1999 | Bessler et al. | |
| 5,860,996 A | 1/1999 | Urban | |
| 5,861,024 A | 1/1999 | Rashidi | |
| 5,861,028 A | 1/1999 | Angell | |
| 5,868,783 A | 2/1999 | Tower | |
| 5,876,448 A | 3/1999 | Thompson et al. | |
| 5,885,228 A * | 3/1999 | Rosenman et al. | 600/587 |
| 5,888,201 A | 3/1999 | Stinson et al. | |
| 5,891,191 A | 4/1999 | Stinson | |
| 5,895,399 A | 4/1999 | Barbut et al. | |
| 5,907,893 A | 6/1999 | Zadno-Azizi et al. | |
| 5,910,154 A | 6/1999 | Tsugita et al. | |
| 5,911,734 A | 6/1999 | Tsugita et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A | 9/1999 | Leonhardt et al. | |
| 5,968,070 A | 10/1999 | Bley et al. | |
| 5,984,957 A | 11/1999 | Laptewicz, Jr. et al. | |
| 5,984,959 A * | 11/1999 | Robertson et al. | 623/2.11 |
| 5,993,469 A | 11/1999 | McKenzie et al. | |
| 5,997,557 A | 12/1999 | Barbut et al. | |
| 6,010,522 A | 1/2000 | Barbut et al. | |
| 6,022,370 A | 2/2000 | Tower | |
| 6,027,520 A | 2/2000 | Tsugita et al. | |
| 6,027,525 A | 2/2000 | Suh et al. | |
| 6,042,598 A | 3/2000 | Tsugita et al. | |
| 6,042,607 A | 3/2000 | Williamson, IV et al. | |
| 6,093,203 A | 7/2000 | Uflacker | |
| 6,123,723 A | 9/2000 | Konya et al. | |
| 6,142,987 A | 11/2000 | Tsugita | |
| 6,162,245 A | 12/2000 | Jayaraman | |
| 6,165,200 A | 12/2000 | Tsugita et al. | |
| 6,165,209 A | 12/2000 | Patterson et al. | |
| 6,168,579 B1 | 1/2001 | Tsugita | |
| 6,168,614 B1 | 1/2001 | Andersen et al. | |
| 6,171,327 B1 | 1/2001 | Daniel et al. | |
| 6,179,859 B1 | 1/2001 | Bates | |
| 6,187,016 B1 | 2/2001 | Hedges et al. | |
| 6,197,053 B1 | 3/2001 | Cosgrove et al. | |
| 6,200,336 B1 | 3/2001 | Pavcnik et al. | |
| 6,214,036 B1 | 4/2001 | Letendre et al. | |
| 6,221,006 B1 | 4/2001 | Dubrul et al. | |
| 6,221,091 B1 | 4/2001 | Khosravi | |
| 6,221,096 B1 * | 4/2001 | Aiba et al. | 623/1.11 |
| 6,231,544 B1 | 5/2001 | Tsugita et al. | |
| 6,231,551 B1 | 5/2001 | Barbut | |
| 6,241,757 B1 | 6/2001 | An et al. | |
| 6,245,102 B1 | 6/2001 | Jayaraman | |
| 6,251,135 B1 | 6/2001 | Stinson et al. | |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,267,783 B1 | 7/2001 | Letendre et al. | |
| 6,270,513 B1 | 8/2001 | Tsugita et al. | |
| 6,277,555 B1 | 8/2001 | Duran et al. | |
| 6,309,417 B1 | 10/2001 | Spence et al. | |
| 6,319,281 B1 | 11/2001 | Patel | |
| 6,327,772 B1 | 12/2001 | Zadno-Azizi et al. | |
| 6,336,934 B1 | 1/2002 | Gilson et al. | |
| 6,336,937 B1 | 1/2002 | Vonesh et al. | |
| 6,338,735 B1 | 1/2002 | Stevens | |
| 6,348,063 B1 | 2/2002 | Yassour et al. | |
| 6,352,708 B1 | 3/2002 | Duran et al. | |
| 6,361,545 B1 | 3/2002 | Macoviak et al. | |

| Patent | Date | Inventors |
|---|---|---|
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,425,916 B1 * | 7/2002 | Garrison et al. ............. 623/2.11 |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsuigita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 * | 9/2003 | Thompson et al. .......... 623/1.11 |
| 6,632,243 B1 | 10/2003 | Zadno-Azizi et al. |
| 6,635,068 B1 | 10/2003 | Dubrul et al. |
| 6,635,079 B2 * | 10/2003 | Unsworth et al. ........... 623/1.11 |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 * | 8/2004 | Stallings et al. ............. 623/1.11 |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 * | 5/2005 | Macoviak .................... 623/2.11 |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,974,464 B2 | 12/2005 | Quijano et al. |
| 6,974,474 B2 | 12/2005 | Pavcnik et al. |
| 6,974,476 B2 * | 12/2005 | McGuckin et al. .......... 623/2.36 |
| 6,979,350 B2 | 12/2005 | Moll et al. |
| 6,984,242 B2 | 1/2006 | Campbell et al. |
| 7,011,681 B2 * | 3/2006 | Vesely ......................... 623/2.11 |
| 7,018,406 B2 | 3/2006 | Seguin et al. |
| 7,025,791 B2 * | 4/2006 | Levine et al. .............. 623/23.64 |
| 7,037,331 B2 * | 5/2006 | Mitelberg et al. ............ 623/1.15 |
| 7,122,020 B2 | 10/2006 | Mogul |
| 7,166,097 B2 | 1/2007 | Barbut |
| 7,175,653 B2 * | 2/2007 | Gaber ......................... 623/1.15 |
| 7,175,654 B2 * | 2/2007 | Bonsignore et al. ......... 623/1.15 |
| 7,189,258 B2 * | 3/2007 | Johnson et al. ............. 623/2.11 |
| 7,191,018 B2 | 3/2007 | Gielen et al. |
| 7,201,772 B2 | 4/2007 | Schwammenthal et al. |
| 7,235,093 B2 | 6/2007 | Gregorich .................... 623/1.11 |
| 7,258,696 B2 * | 8/2007 | Rabkin et al. ................ 623/1.11 |
| 7,374,560 B2 | 5/2008 | Ressemann et al. |
| 7,632,298 B2 | 12/2009 | Hijlkema et al. |
| 7,722,666 B2 | 5/2010 | Lafontaine |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 * | 3/2003 | Yang et al. .................. 623/2.11 |
| 2003/0055495 A1 * | 3/2003 | Pease et al. ................. 623/2.11 |
| 2003/0060844 A1 | 3/2003 | Borillo et al. |
| 2003/0070944 A1 | 4/2003 | Nigam |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149478 A1 | 8/2003 | Figulla et al. |
| 2003/0176884 A1 | 9/2003 | Berrada et al. |

| | | |
|---|---|---|
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1* | 2/2004 | Quijano et al. ............ 623/2.11 |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri et al. |
| 2004/0088045 A1 | 5/2004 | Cox |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0107004 A1* | 6/2004 | Levine et al. ............ 623/23.64 |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1* | 9/2004 | Lobbi ......................... 623/2.11 |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0254636 A1 | 12/2004 | Flagle et al. |
| 2005/0033402 A1 | 2/2005 | Cully et al. |
| 2005/0043711 A1 | 2/2005 | Corcoran et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1* | 6/2005 | Salahieh et al. ............ 623/2.11 |
| 2005/0137687 A1* | 6/2005 | Salahieh et al. ............ 623/2.11 |
| 2005/0137688 A1* | 6/2005 | Salahieh et al. ............ 623/2.11 |
| 2005/0137689 A1* | 6/2005 | Salahieh et al. ............ 623/2.11 |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1* | 6/2005 | Haug et al. ................. 623/2.11 |
| 2005/0137694 A1 | 6/2005 | Haug et al. |
| 2005/0137695 A1* | 6/2005 | Salahieh et al. ............ 623/2.11 |
| 2005/0137696 A1* | 6/2005 | Salahieh et al. ............ 623/2.11 |
| 2005/0137697 A1* | 6/2005 | Salahieh et al. ............ 623/2.11 |
| 2005/0137698 A1 | 6/2005 | Salahieh et al. |
| 2005/0137699 A1* | 6/2005 | Salahieh et al. ............ 623/2.11 |
| 2005/0137701 A1* | 6/2005 | Salahieh et al. ............ 623/2.38 |
| 2005/0137702 A1* | 6/2005 | Haug et al. ................. 623/2.38 |
| 2005/0143809 A1* | 6/2005 | Salahieh et al. ............ 623/2.11 |
| 2005/0165352 A1 | 7/2005 | Henry et al. |
| 2005/0165477 A1 | 7/2005 | Anduiza et al. |
| 2005/0182486 A1 | 8/2005 | Gabbay |
| 2005/0197694 A1 | 9/2005 | Pai et al. |
| 2005/0197695 A1* | 9/2005 | Stacchino et al. ........... 623/2.18 |
| 2005/0203614 A1 | 9/2005 | Forster |
| 2005/0203615 A1 | 9/2005 | Forster |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1* | 12/2005 | Haug et al. .................. 623/2.11 |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1* | 3/2006 | Salahieh et al. ............ 623/2.18 |
| 2006/0155312 A1* | 7/2006 | Levine et al. ................. 606/153 |
| 2006/0161249 A1 | 7/2006 | Realyvasquez et al. |
| 2006/0173524 A1* | 8/2006 | Salahieh et al. ............ 623/1.11 |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0288089 A1 | 12/2007 | Gurskis et al. |
| 2008/0082165 A1 | 4/2008 | Wilson et al. |
| 2008/0288054 A1 | 11/2008 | Pulnev et al. |
| 2009/0005863 A1 | 1/2009 | Goetz et al. |
| 2009/0171456 A1* | 7/2009 | Kveen et al. ................. 623/2.11 |
| 2009/0222076 A1 | 9/2009 | Figulla et al. |
| 2010/0219092 A1 | 9/2010 | Salahieh et al. |

FOREIGN PATENT DOCUMENTS

| | | |
|---|---|---|
| EP | 0409929 B1 | 4/1997 |
| EP | 1000590 A1 | 5/2000 |
| EP | 1057459 | 12/2000 |
| EP | 1057460 | 12/2000 |
| EP | 0937439 B1 | 9/2003 |
| EP | 1340473 A2 | 9/2003 |
| EP | 1356793 | 10/2003 |
| EP | 1042045 B1 | 5/2004 |
| EP | 0819013 | 6/2004 |
| EP | 1229864 B1 | 4/2005 |
| EP | 1430853 A2 | 6/2005 |
| EP | 1059894 B1 | 7/2005 |
| EP | 1078610 B1 | 8/2005 |
| EP | 1576937 A2 | 9/2005 |
| EP | 1582178 A2 | 10/2005 |
| EP | 1582179 A2 | 10/2005 |
| EP | 1469797 | 11/2005 |
| EP | 1600121 A1 | 11/2005 |
| EP | 1156757 B1 | 12/2005 |
| EP | 1616531 | 1/2006 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 96/24306 A1 | 8/1996 |
| WO | WO 98/36790 | 8/1998 |
| WO | WO 98/50103 A1 | 11/1998 |
| WO | WO 98/57599 A2 | 12/1998 |
| WO | WO 99/44542 A2 | 9/1999 |
| WO | WO 00/09059 | 2/2000 |
| WO | WO 00/44308 | 8/2000 |
| WO | WO 00/44313 | 8/2000 |
| WO | WO 00/49970 A1 | 8/2000 |
| WO | WO 00/67661 | 11/2000 |
| WO | WO 01/05331 | 1/2001 |
| WO | WO 01/08596 A1 | 2/2001 |
| WO | WO 01/10320 A1 | 2/2001 |
| WO | WO 01/10343 A1 | 2/2001 |

| | | |
|---|---|---|
| WO | WO 01/35870 | 5/2001 |
| WO | WO 01/64137 | 9/2001 |
| WO | WO 02/36048 | 5/2002 |
| WO | WO 02/41789 A2 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO03/030776 A2 | 4/2003 |
| WO | WO 03/015851 | 11/2003 |
| WO | WO03/094797 | 11/2003 |
| WO | WO 2004/014256 A1 | 2/2004 |
| WO | WO 2004/019811 | 3/2004 |
| WO | WO 2004/023980 | 3/2004 |
| WO | WO 2004/026117 A2 | 4/2004 |
| WO | WO 2004/041126 | 5/2004 |
| WO | WO 2004/047681 A1 | 6/2004 |
| WO | WO 2004/066876 A1 | 8/2004 |
| WO | WO 2004/082536 A1 | 9/2004 |
| WO | WO 2005/084595 A1 | 9/2005 |
| WO | WO 2005/087140 A1 | 9/2005 |

OTHER PUBLICATIONS

Salahieh, et al., U.S. Appl. No. 11/274,889, entitled "Medical implant deployment tool," filed Nov. 14, 2005 (SLG Reference No. 10012-718.201).

Salahieh, et al., U.S. Appl. No. 11/314,183, entitled "Medical Device Delivery," filed Dec. 20, 2005 (SLG Reference No. 10012-725.201).

Salahieh, et al., U.S. Appl. No. 11/314,969, entitled "Methods and Apparatus for Performing Valvuloplasty," filed Dec. 20, 2005 (WSGR Reference No. 10012-727.201).

Salahieh, et al., U.S. Appl. No. 11/275,913, entitled "Two-Part Package for Medical Implant," filed Feb. 2, 2006 (WSGR Reference No. 10012-723.201).

Salahieh, et al., U.S. Appl. No. 11/531,980, entitled "Externally expandable heart valve anchor and method," filed Sep. 14, 2006 (SLG Reference No. 10012-703.301).

Salahieh, et al., U.S. Appl. No. 11/532,019, entitled "Methods and apparatus for endovascularly replacing heart valve," filed Sep. 14, 2006 (SLG Reference No. 10012-703.302).

Salahieh, et al; U.S. Appl. No. 11/732,906 entitled "Assessing the location and performance of replacement heart valves," filed Apr. 4, 2007 (SLG #10012-702.505).

Andersen, H.R. et al. "Transluminal implantation of artificial heart valves. Description of a new expandable aortic valve and initial results with implantation by catheter technique in closed chest pigs." Euro. Heart J. 1992; 13:704-708.

Atwood, A. et al. "Insertion of Heart Valves by Catheterization." Project Supervised by Prof. S. Muftu of Northeaster University 2001-2002: 36-40.

Bodnar, E. et al. Replacement Cardiac Valves R Chapter 13: Extinct cardiac valve prostheses. Pergamon Publishing Corporation. New York, 1991: 307-322.

Boudjemline, Y. et al. "Percutaneous implantation of a biological valve in the aorta to treat aortic valve insufficiency—a sheep study." Med Sci. Monit. 2002; vol. 8, No. 4: BR113-116.

Boudjemline, Y. et al. "Percutaneous implantation of a valve in the descending aorta in lambs." Euro. Heart J. 2002; 23: 1045-1049.

Boudjemline, Y. et al. "Percutaneous valve insertion: A new approach?" J. of Thoracic and Cardio. Surg. 2003; 125(3): 741-743.

Boudjemline, Y. et al. "Steps Toward Percutaneous Aortic Valve Replacement." Circulation. 2002; 105: 775-778.

Cribier, A., et al. "Percutaneous Transcatheter Implantation of an Aortic Valve Prosthesis for Calcific Aortic Stenosis: First Human Case Description." Circulation. 2002; 106: 3006-3008.

Cribier, A., et al. "Percutaneous Transcatheter Implantation of an Aortic Valve Prosthesis for Calcific Aortic Stenosis: First Human Case." Percutaneous Valve Technologies, Inc. 2002: 16 pages.

Ferrari, M. et al. "Percutaneous transvascular aortic valve replacement with self expanding stent-valve device." Poster from the presentation given at SMIT 2000, 12th International Conference. Sep. 5, 2000.

Knudsen, L. L. et al. "Catheter-implanted prosthetic heart valves." Int'l J. of Art. Organs. 1993; 16(5): 253-262.

Kort, S. et al. "Minimally invasive aortic valve replacement: Echocardiographic and clinical results." Am. Heart J. 2001; 142(3): 476-481.

Love, C. et al. "The Autogenous Tissue Heart Valve: Current Status." Journal of Cardiac Surgery. 1991; 6(4): 499-507.

Lutter, G. et al. "Percutaneous aortic valve replacement: An experimental study. I. Studies on implantation." J. of Thoracic and Cardio. Surg. 2002; 123(4): 768-776.

Moulopoulos, S. D. et al. "Catheter-Mounted Aortic Valves." Annals of Thoracic Surg. 1971; 11 (5): 423-430.

Paniagua, D. et al. "Percutaneous heart valve in the chronic in vitro testing model." Circulation. 2002; 106: e51-e52.

Pavcnik, D. et al. "Percutaneous bioprosthetic venous valve: A long-term study in sheep." J. of Vascular Surg. 2002; 35(3): 598-603.

Phillips, S. J. at al. "A Temporary Catheter-Tip Aortic Valve: Hemodynamic Effects on Experimental Acute Aortic Insufficiency." Annals of Thoracic Surg. 1976; 21(2): 134-136.

Sochman, J. et al. "Percutaneous Transcatheter Aortic Disc Valve Prosthesis Implantation: A Feasibility Study." Cardiovasc. Intervent. Radiol. 2000; 23: 384-388.

Van Herwerden, L. A. et al., "Percutaneous valve implantation: back to the future?" Euro. Heart J. 2002; 23(18): 1415-1416.

Zhou, J. Q. et al. "Self-expandable valved stent of large size: off-bypass implantation in pulmonary position." Eur. J. Cardiothorac. 2003; 24: 212-216.

Haug et al.; U.S. Appl. No. 12/028,452 entitled "Methods and apparatus for endovascularly replacing a patient's heart valve," filed Feb. 8, 2008.

Salahieh, et al., U.S. Appl. No. 12/132,304 entitled "Low profile heart valve and delivery system," filed Jun. 3, 2008.

Boudjemline, Y. et al. "Percutaneous pulmonary valve replacement in a large right ventricular outflow tract: an experimental study." Journal of the Americal College of Cardiology. 2004; vol. 43(6): 1082-1087.

Cribier, A. et al. "Early Experience with Percutaneous Transcatheter Implantation of Heart Valve Prosthesis for the Treatment of End-Stage Inoperable Patients with Calcific Aortic Stenosis." J. of Am. Coll. of Cardio. 2004; 43(4): 698-703.

Hijazi, Z.M. "Transcatheter Valve Replacement: A New Era of Percutaneous Cardiac Intervention Begins." J. of Am. College of Cardio. 2004; 43(6): 1088-1089.

Huber, C.H. et al. "Do valved stents compromise coronary flow?" European Journal of Cardio-thoracic Surgery. 2004; vol. 25: 754-759.

Paniagua, D. et al. Heart Watch (2004). Texas Heart Institute. Spring, 2004 Edition: 8 pages.

Stuart, M. "In Heart Valves, A Brave, New Non-Surgical World." Start-Up. 2004: 9-17.

Vahanian, A. et al. "Percutaneous Approaches to Valvular Disease." Circulation. 2004; 109: 1572-1579.

Paul et al.; U.S. Appl. No. 12/578,463 entitled "Medical Devices and Delivery Systems for Delivering Medical Devices," filed Oct. 13, 2009.

Paul et al.; U.S. Appl. No. 12/578,447 entitled "Medical Devices and Delivery Systems for Delivering Medical Devices," filed Oct. 13, 2009.

* cited by examiner

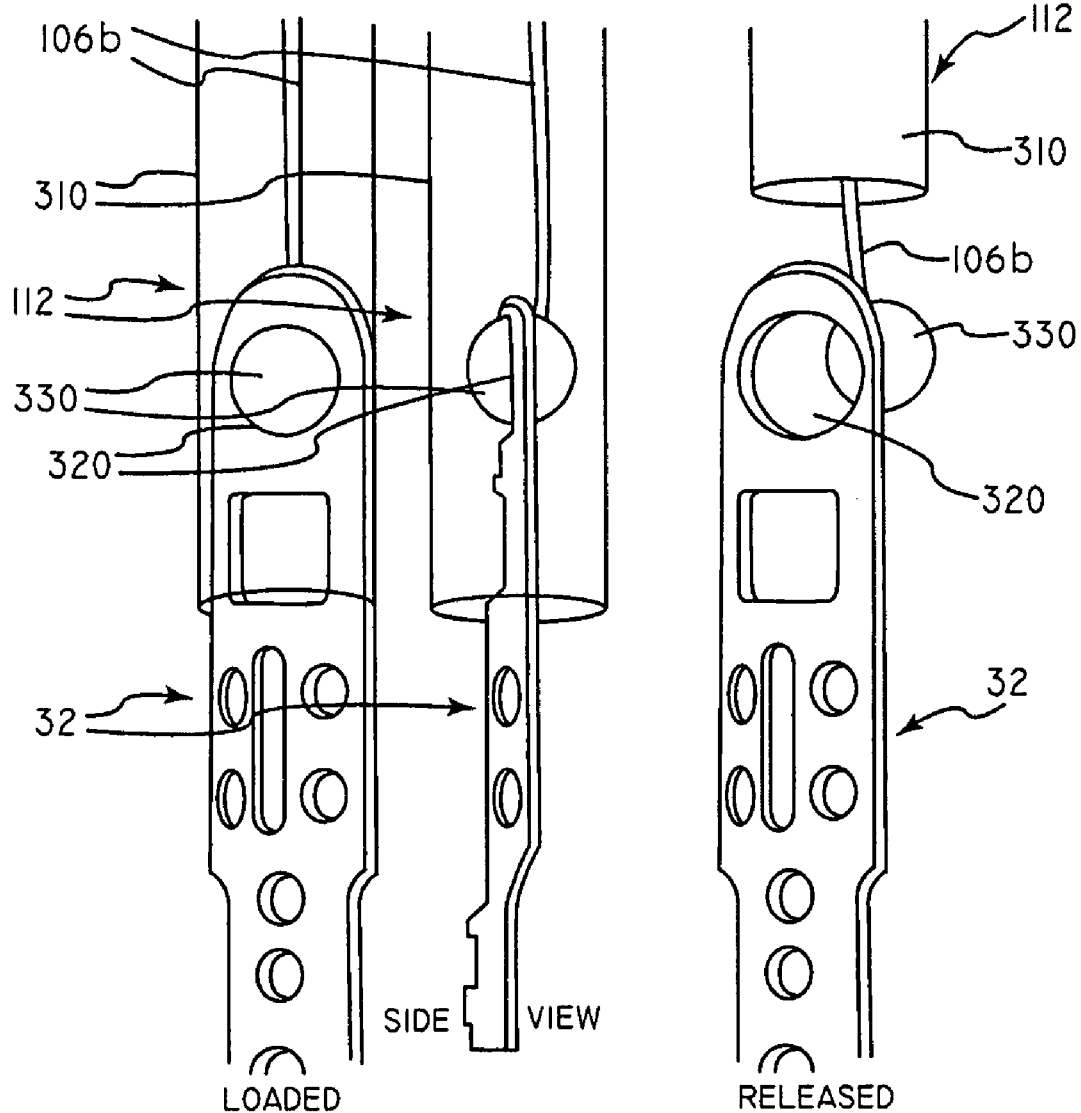

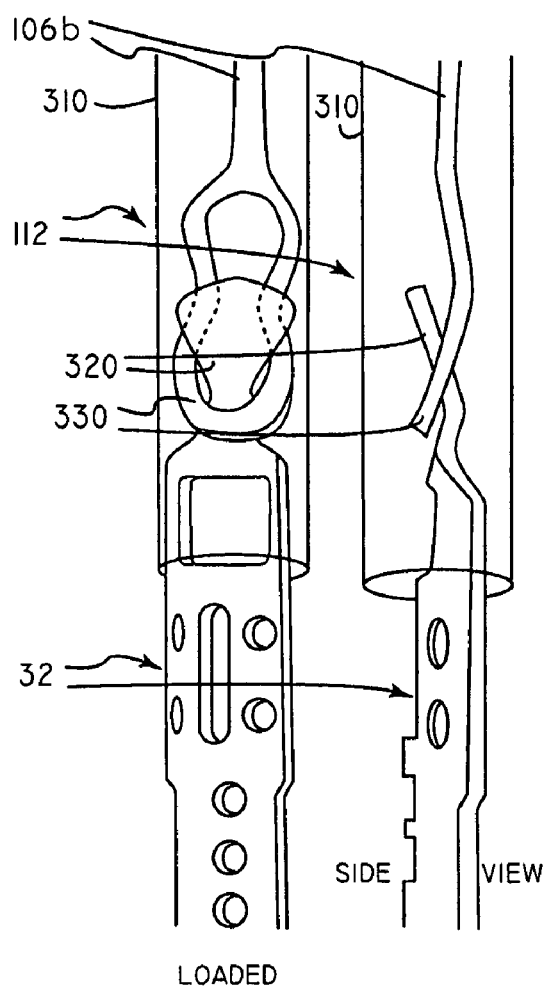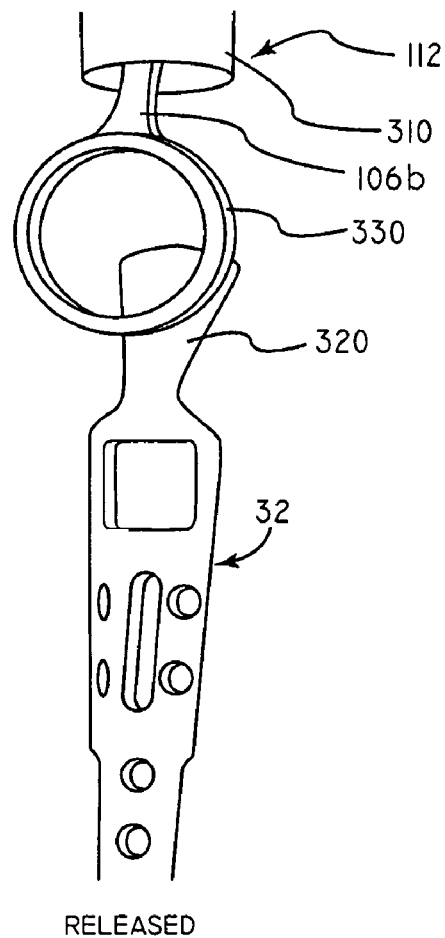
LOADED                    RELEASED
FIG 23A    FIG 23B         FIG 23C

LOADED      RELEASED

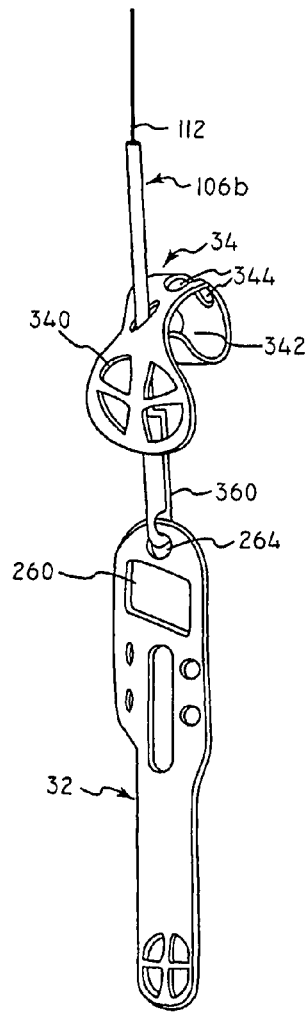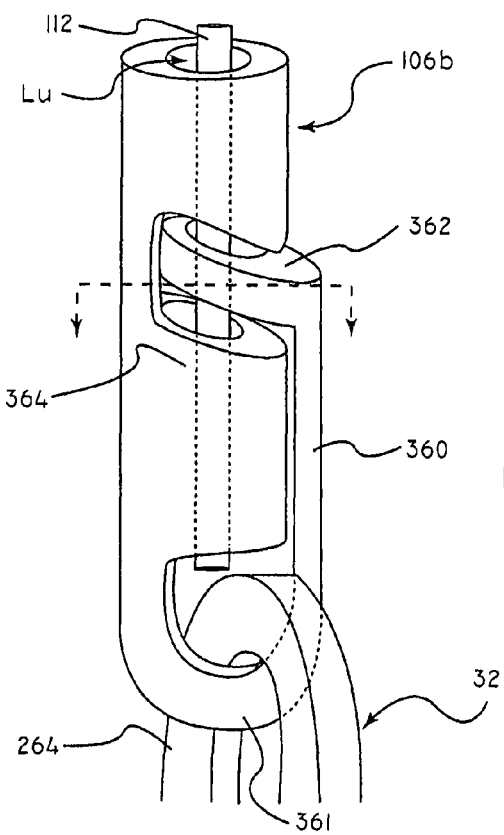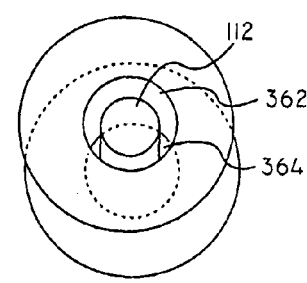
FIG 26A
FIG 26B
FIG 26C

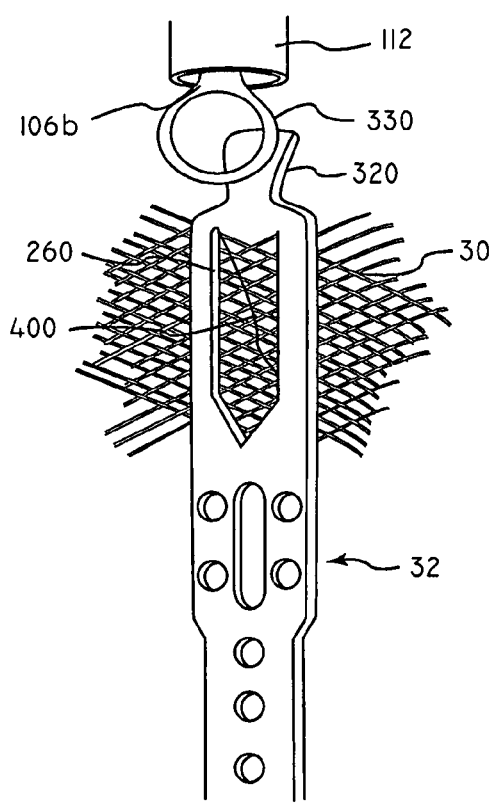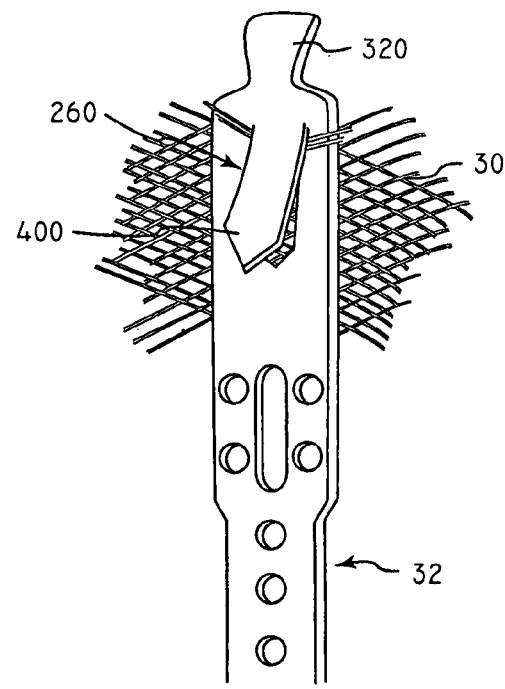
FIG 30A
FIG 30B

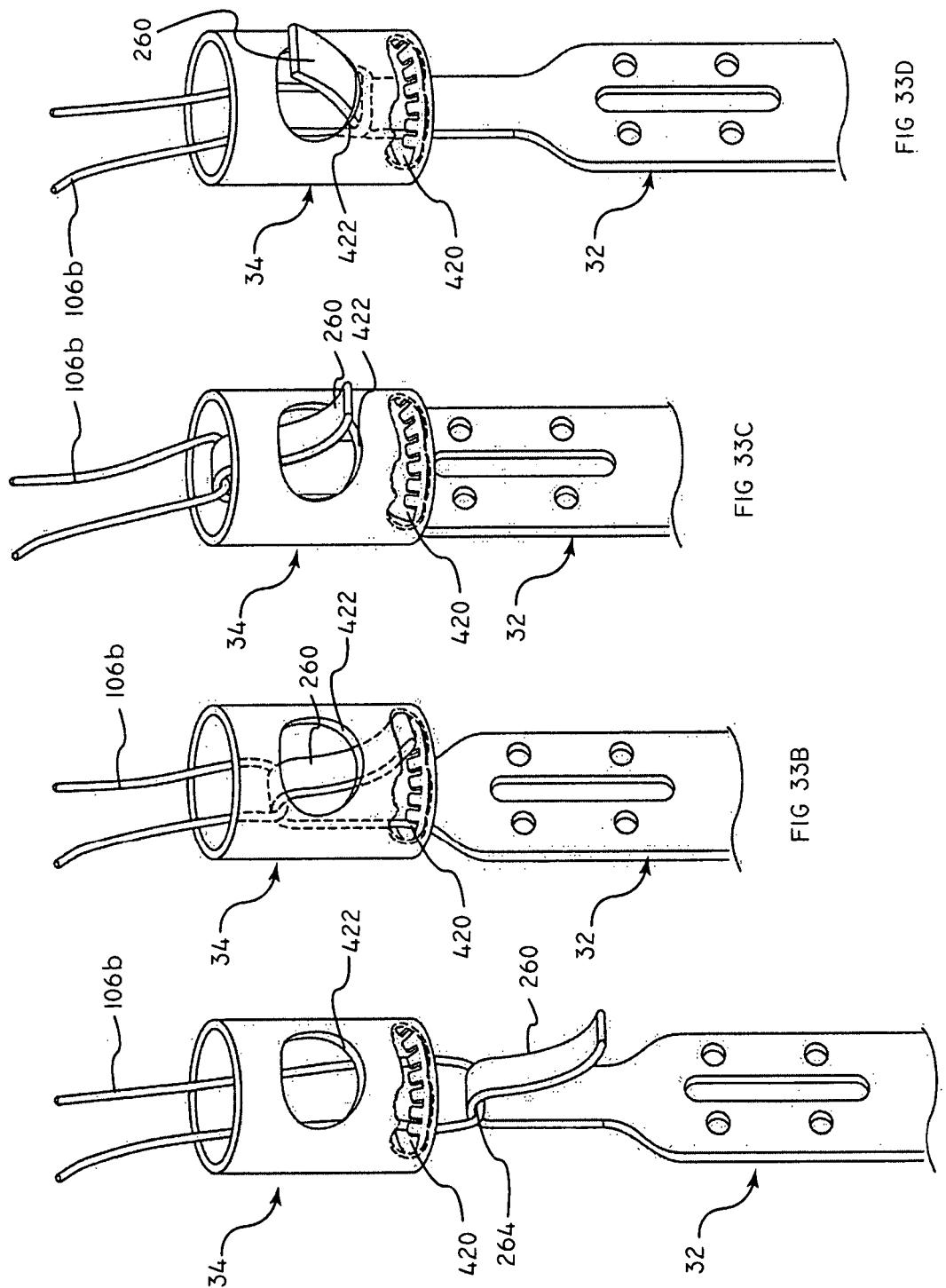

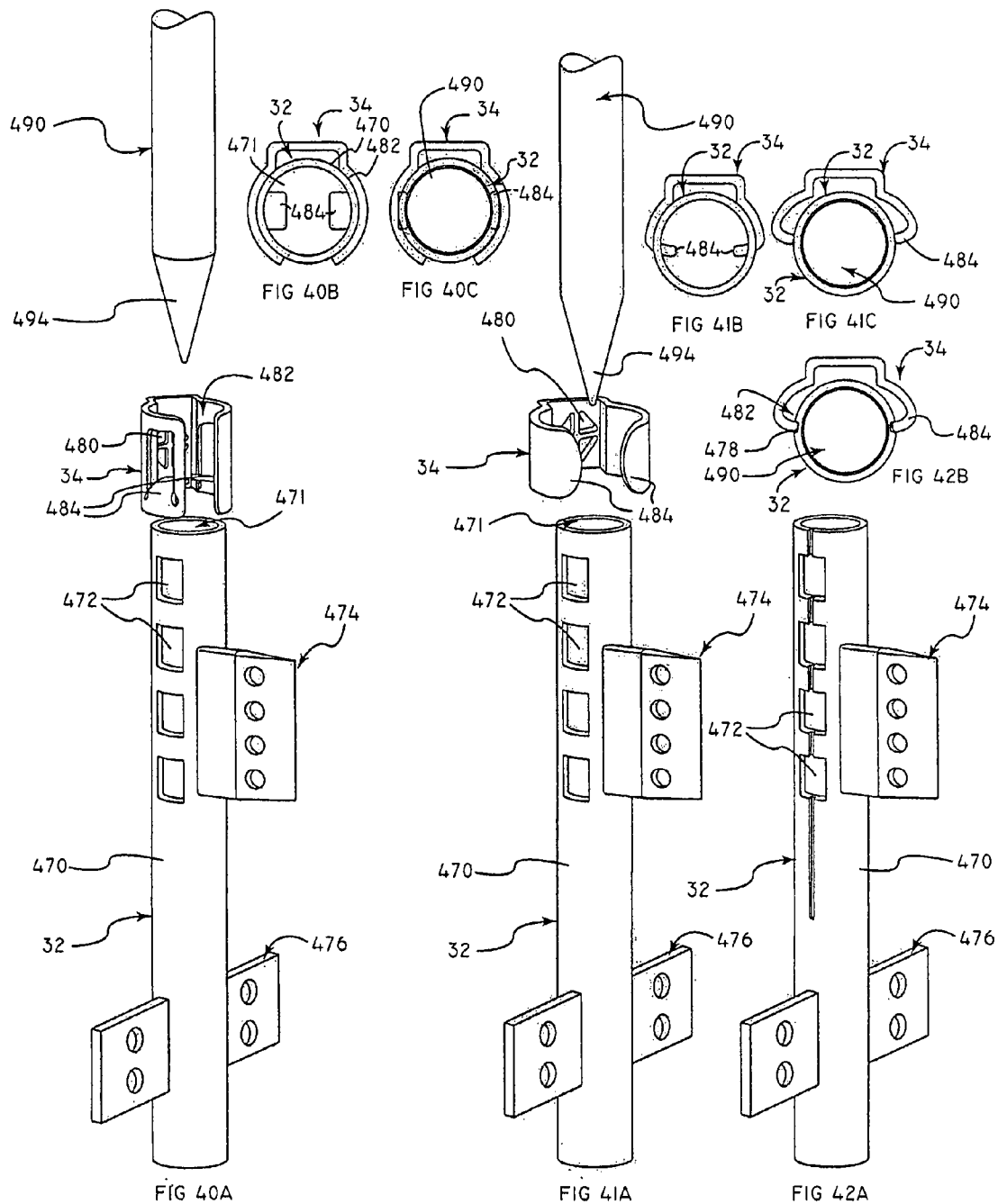

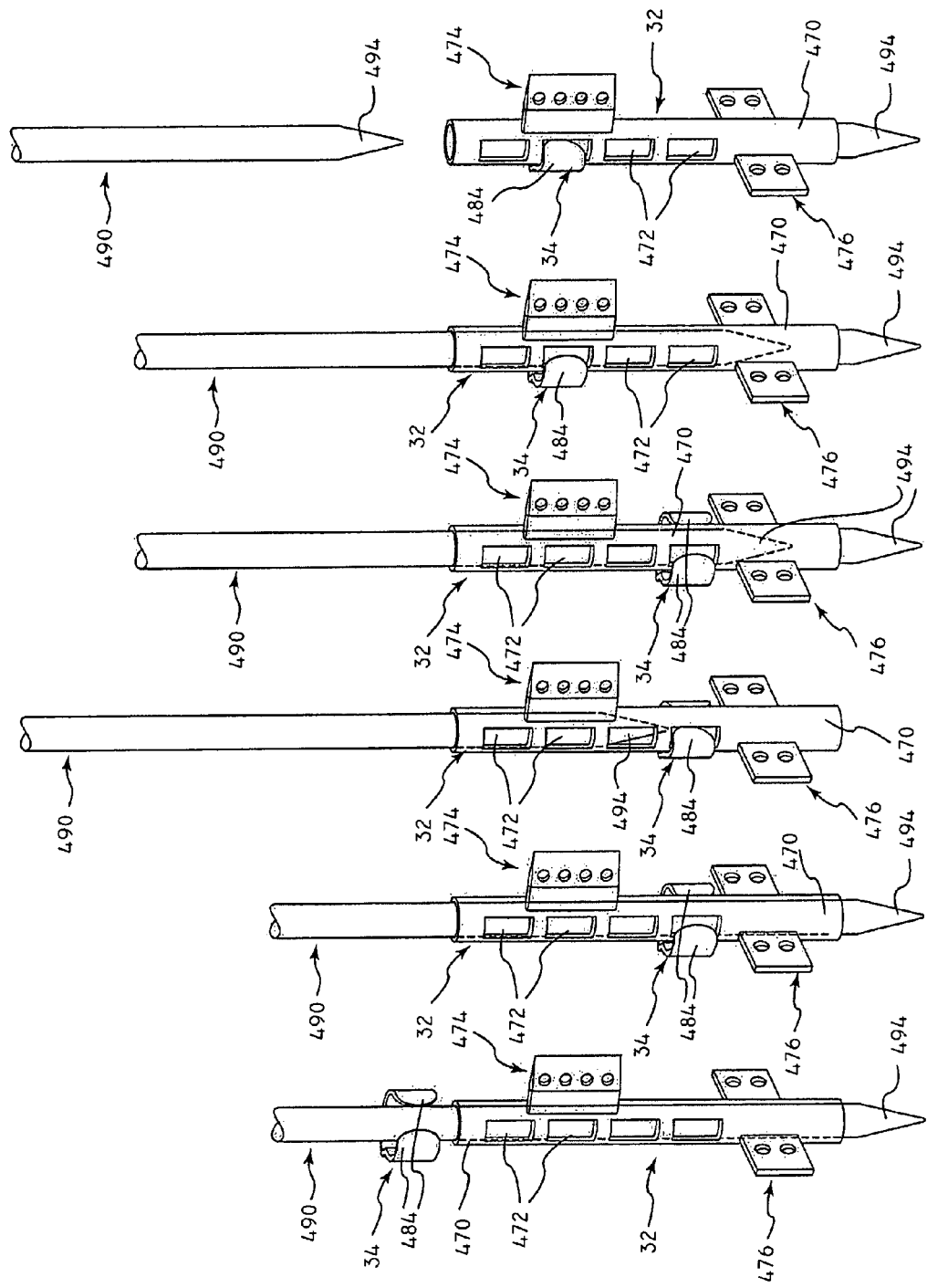

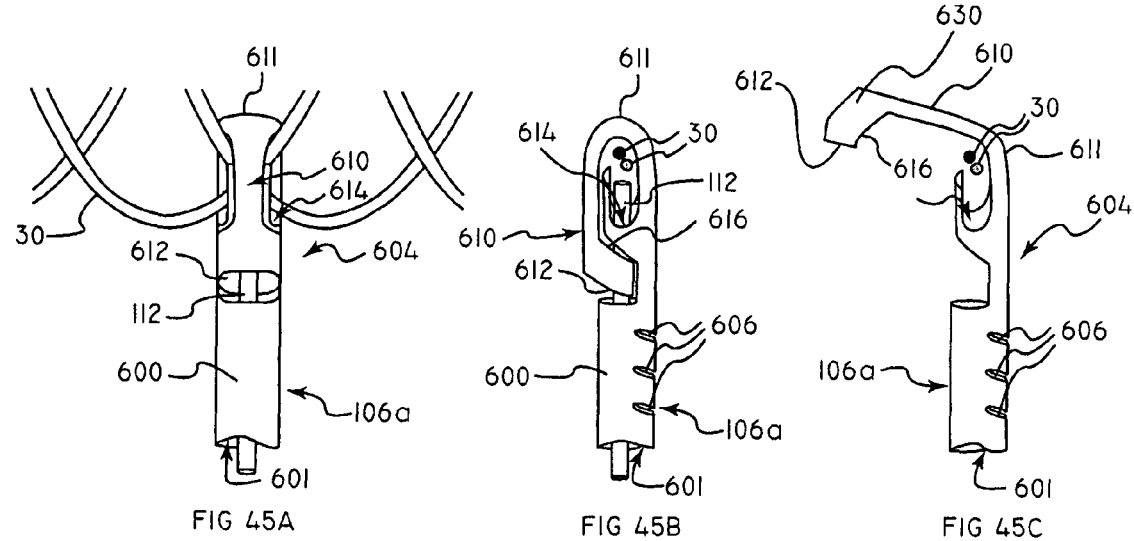

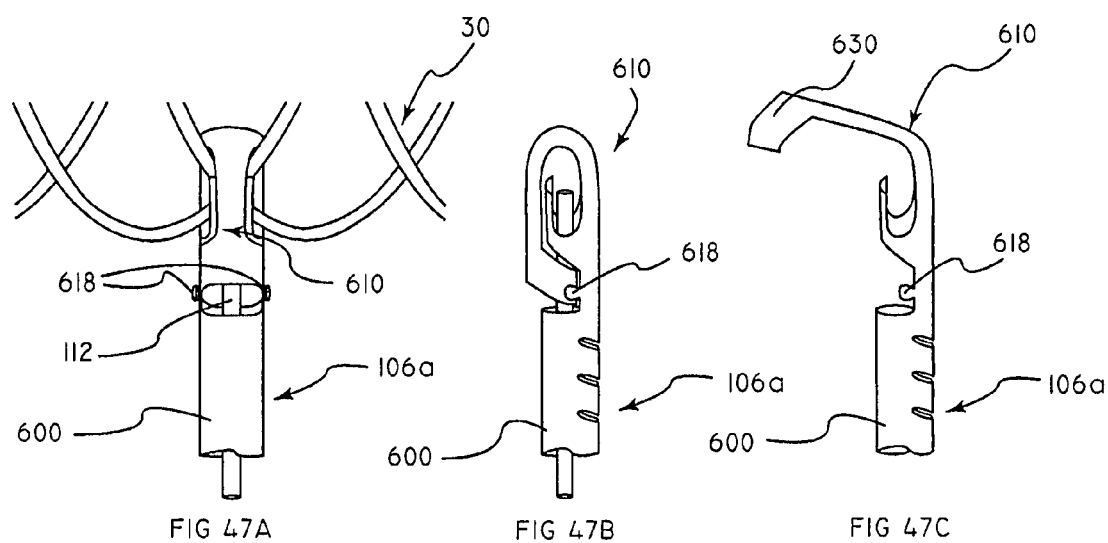

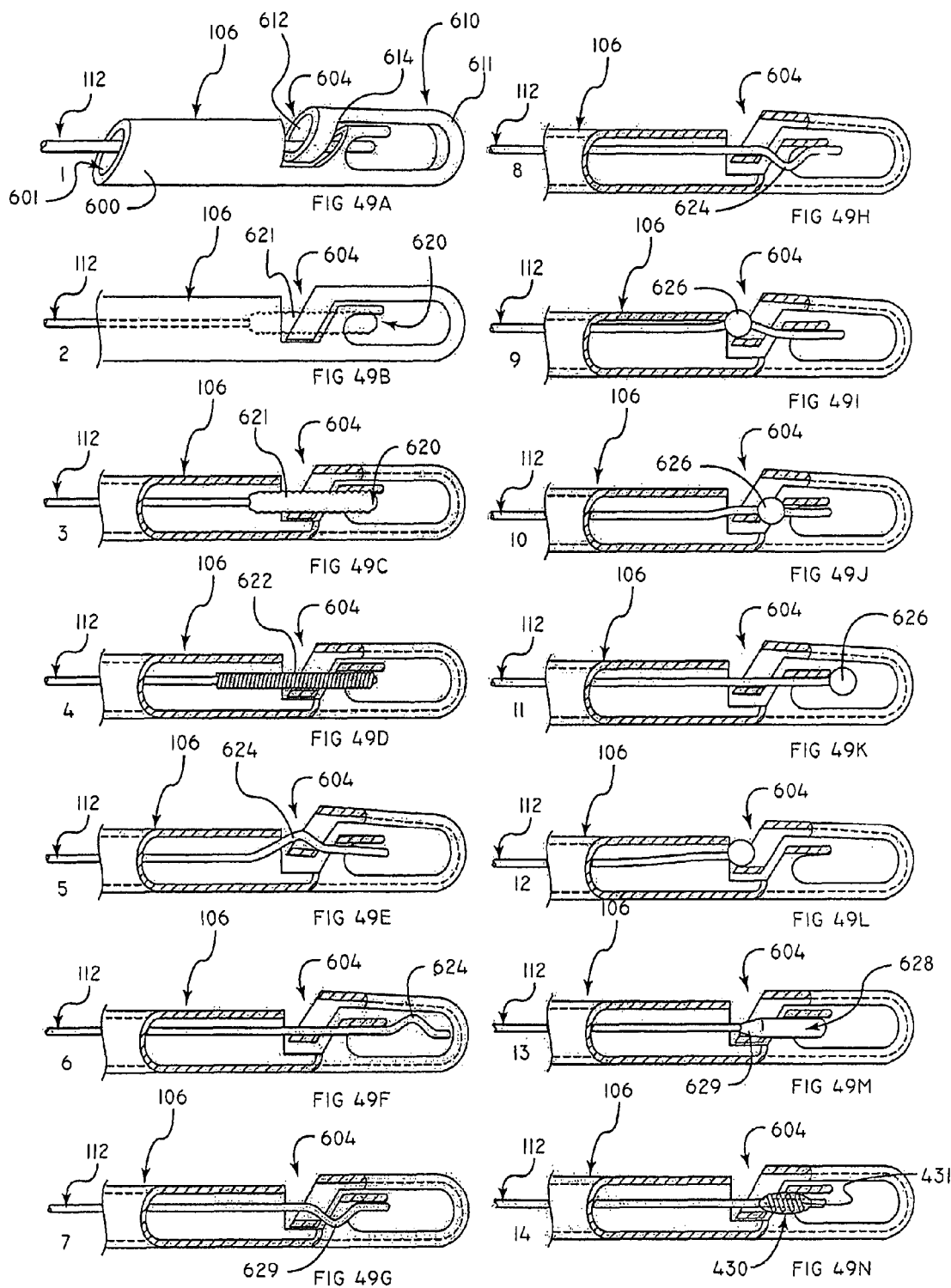

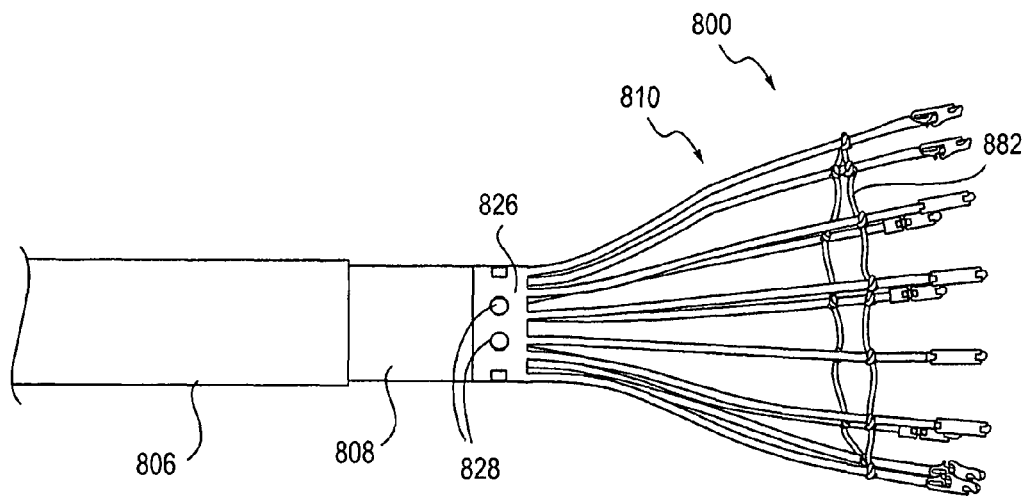
FIG. 58
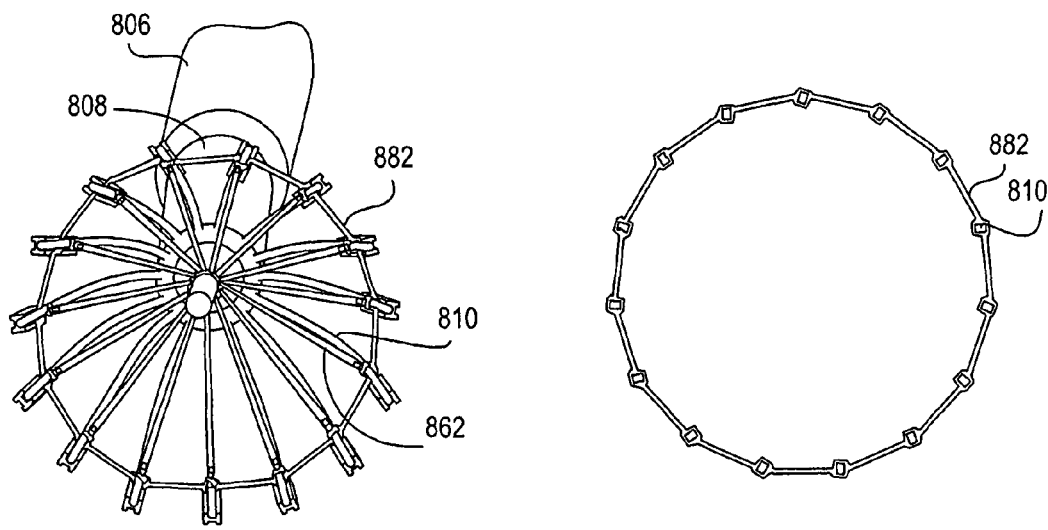
FIG. 59
FIG. 60

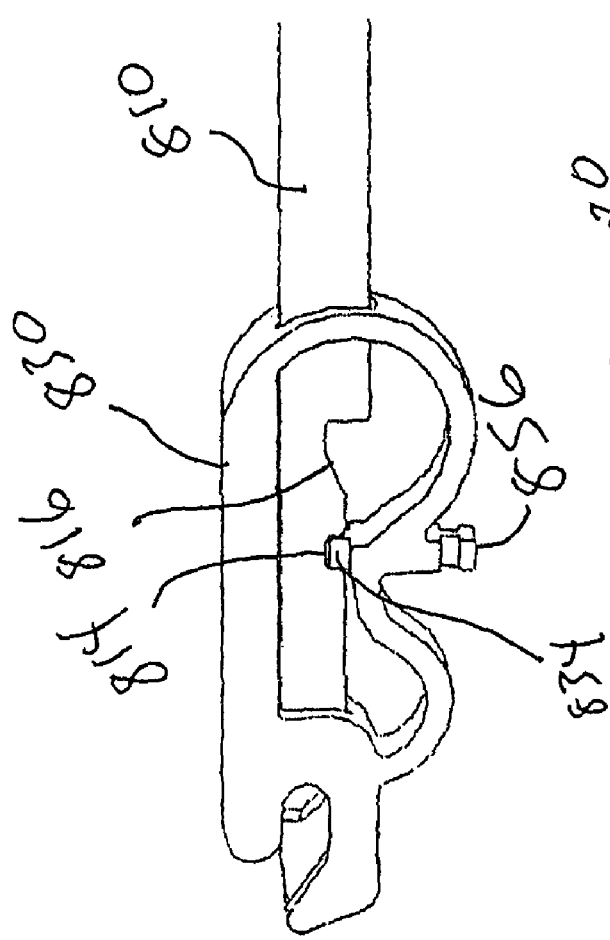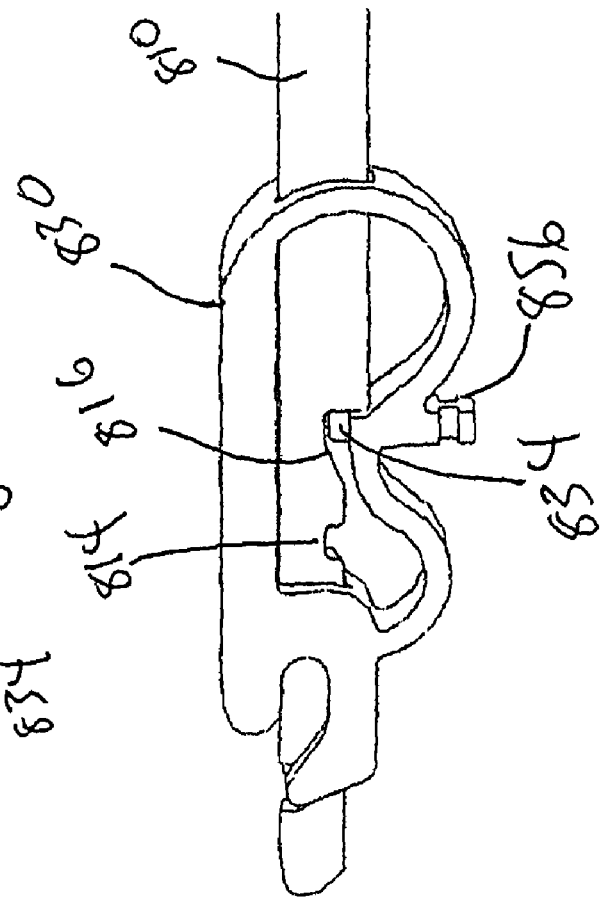

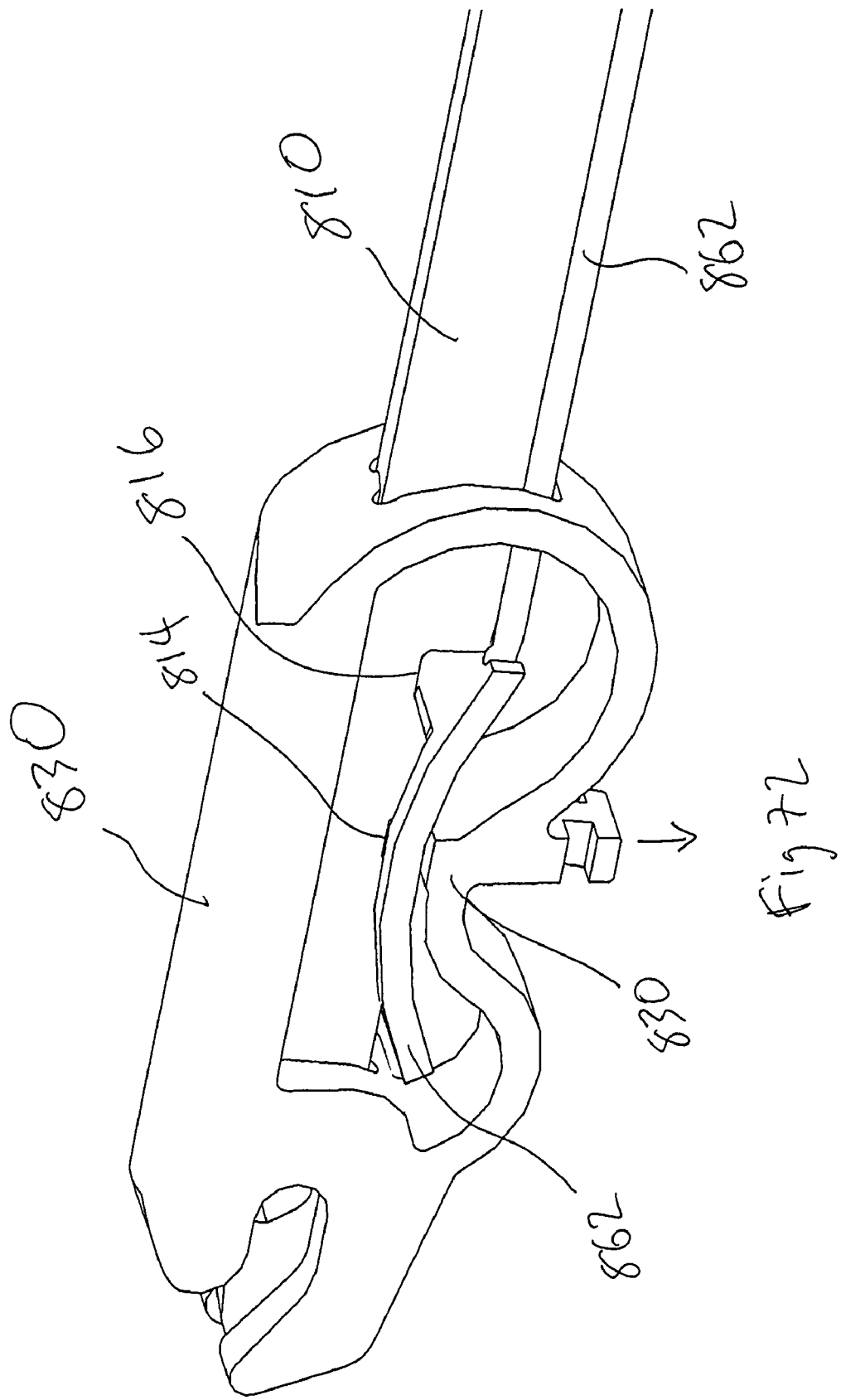

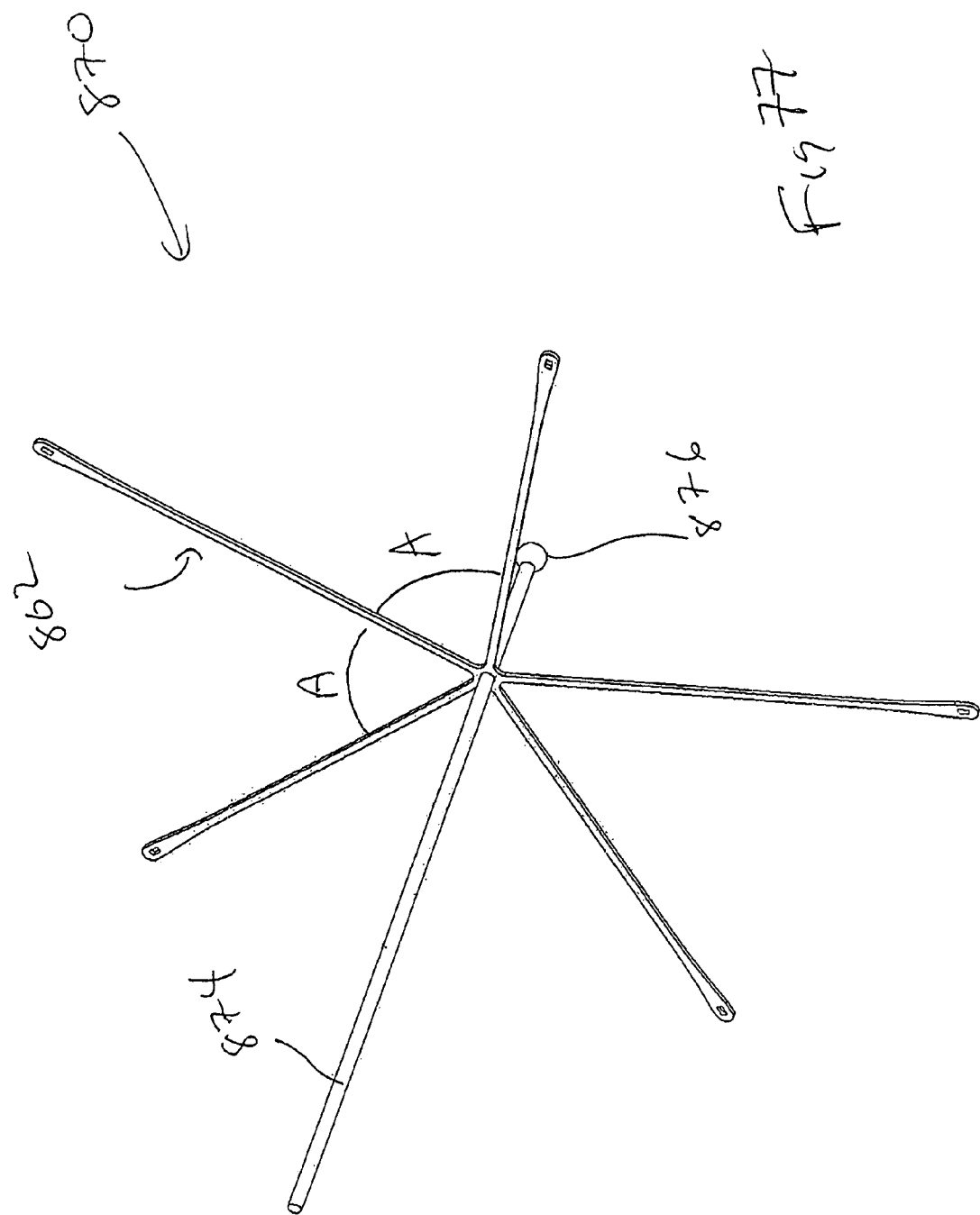

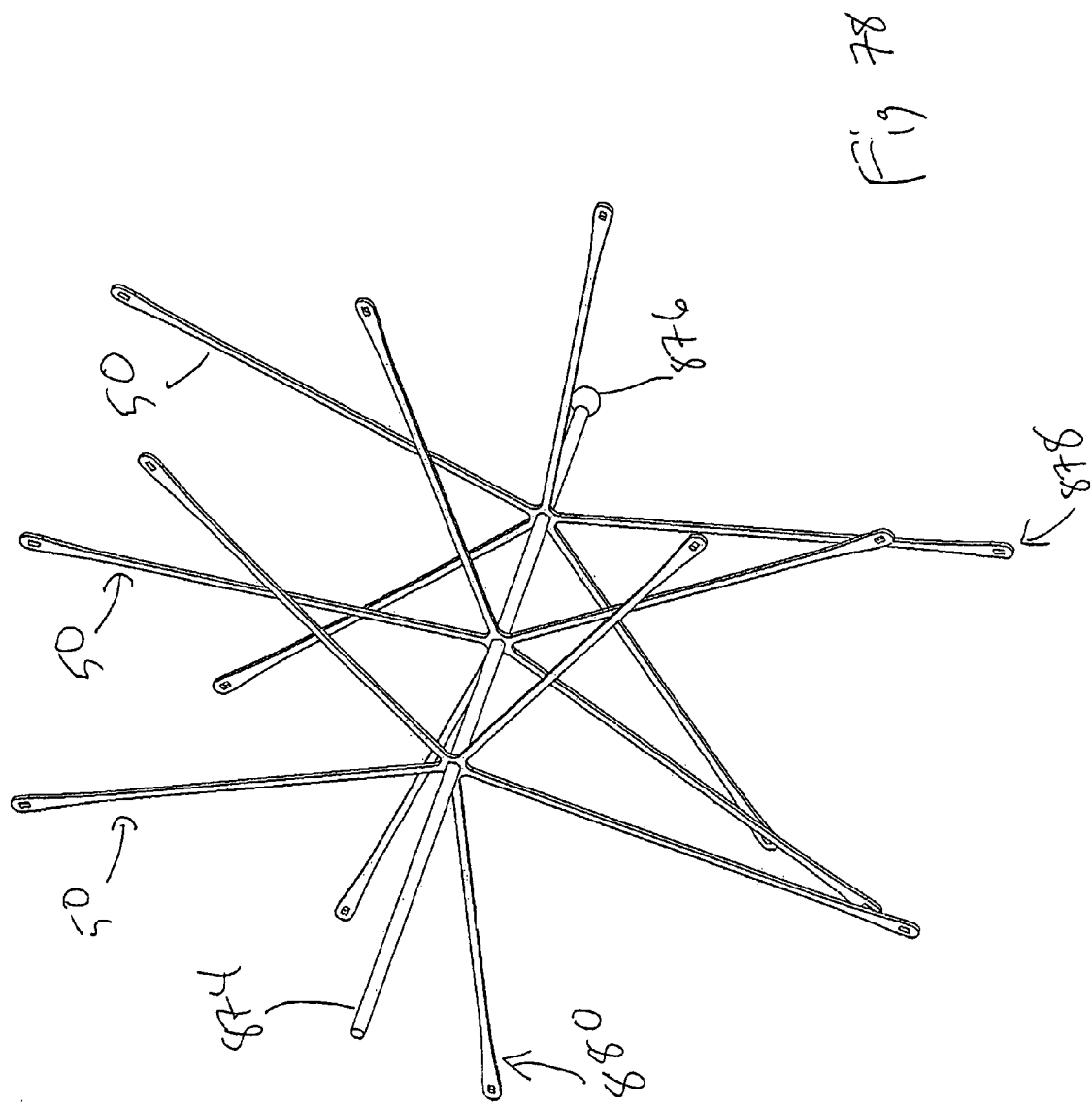

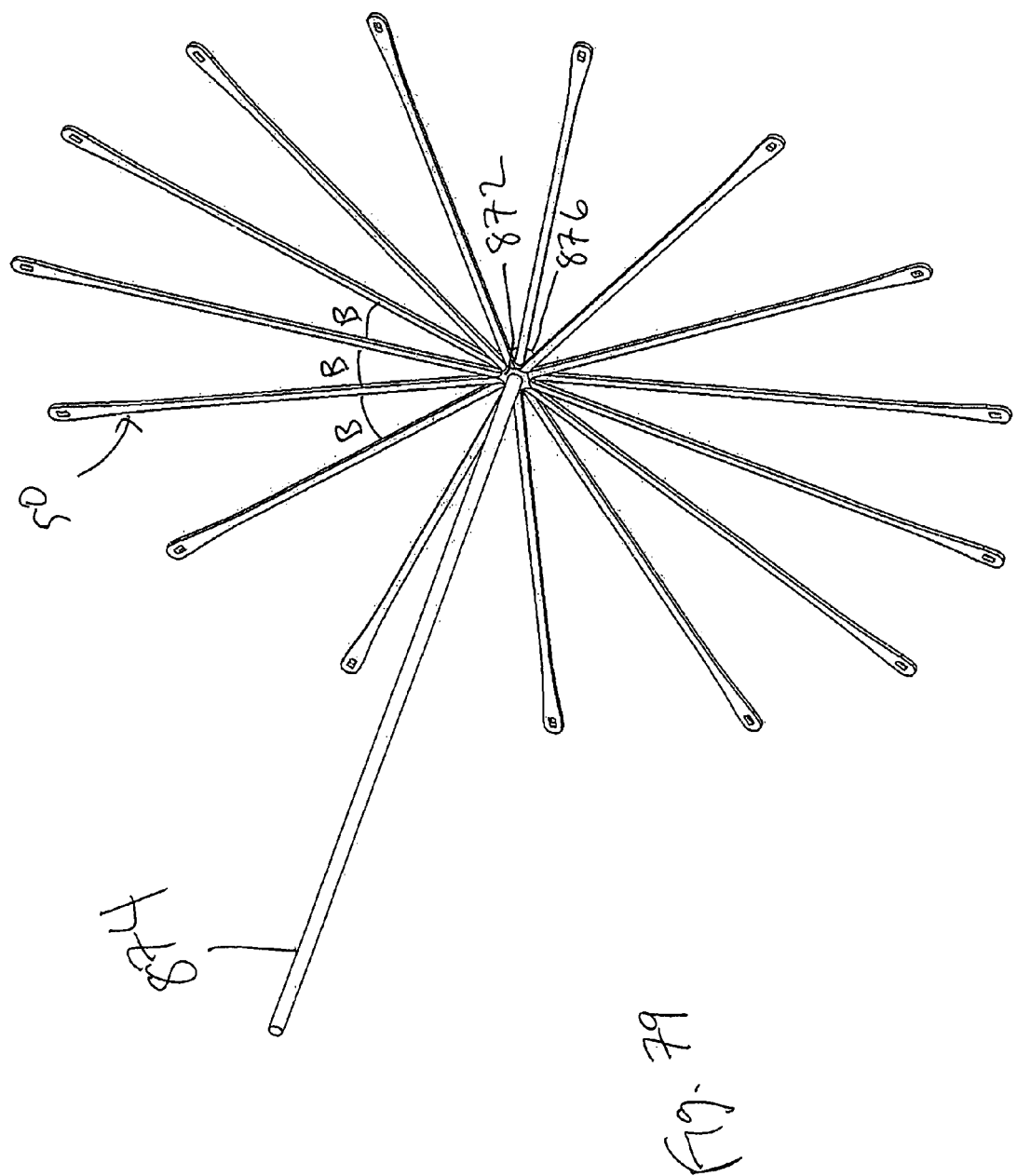

SYSTEMS AND METHODS FOR DELIVERING A MEDICAL IMPLANT

CROSS REFERENCE TO RELATED APPLICATIONS

This application is a continuation-in-part of U.S. patent application Ser. No. 10/982,388, filed Nov. 5, 2004, which is a continuation-in-part application of U.S. patent application Ser. No. 10/746,120, filed Dec. 23, 2003, now abandoned which applications are hereby incorporated by reference in their entirety. This application also claims the benefit of U.S. Provisional Application No. 60/743,288, filed Feb. 14, 2006, which application is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. Two to five percent of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. See, e.g., U.S. Pat. No. 6,168,614. In many of these procedures, the replacement valve is deployed across the native diseased valve to permanently hold the valve open, thereby alleviating a need to excise the native valve and to position the replacement valve in place of the native valve.

In the endovascular aortic valve replacement procedure, accurate placement of aortic valves relative to coronary ostia and the mitral valve is critical. Valve anchors comprising standard self-expanding stent systems are expected to have very poor accuracy in deployment, however. In a typical deployment procedure, the proximal end of the stent is not released from the delivery system until accurate placement is verified by fluoroscopy. The stent may jump to another position once released, making it impossible to know where the ends of the stent will be after release with respect to the native valve, the coronary ostia and the mitral valve.

Also, visualization of the way the new valve is functioning prior to final deployment is very desirable. Due to the expected jumping action of some self-expanding anchors, and because the replacement valve may not be fully functional before final deployment, visualization of valve function and position prior to final and irreversible deployment may not be possible with these systems.

Another expected drawback of prior art self-expanding replacement heart valve systems is their relative lack of radial strength. In order for self-expanding systems to be easily delivered through a delivery sheath, the metal needs to flex and bend inside the delivery catheter without being plastically deformed. Expandable stent designs suitable for endovascular delivery for other purposes may not have sufficient radial strength to serve as replacement heart valve anchors. For example, there are many commercial arterial stent systems that apply adequate radial force against the artery wall to treat atherosclerosis and that can collapse to a small enough of a diameter to fit inside a delivery catheter without plastically deforming. However, when the stent has a valve fastened inside it, and that valve must reside within the heart, as is the case in aortic valve replacement, the anchoring of the stent to vessel walls takes significantly more radial force, especially during diastole. The force to hold back arterial pressure prevent blood from going back inside the ventricle during diastole will be directly transferred to the stent/vessel wall interface. Therefore, the amount of radial force required to keep the self-expanding stent/valve in contact with the vessel wall and not sliding will be much higher than in stents that do not have valves inside of them. Moreover, a self-expanding stent without sufficient radial force will end up dilating and contracting with each heartbeat, thereby distorting the valve, affecting its function and possibly causing it to migrate and dislodge completely. Simply increasing strut thickness of the self-expanding stent is not a good solution as it increases profile and/or a risk of plastic deformation of the self-expanding stent.

In view of drawbacks associated with previously known techniques for endovascularly replacing a heart valve, it would be desirable to provide methods and apparatus that overcome those drawbacks.

SUMMARY OF THE INVENTION

One aspect of the invention is a delivery system adapted to deliver a medical implant through a body lumen and release the medical implant at a location within the body. The delivery system includes a plurality of first actuatable element adapted to engage a plurality of second elements in a first configuration to capture the implant within the delivery system, and wherein the plurality of first actuatable element are adapted to engage the plurality of second elements in a second configuration and to release the implant from the delivery system.

In some embodiments the plurality of first actuatable element are adapted to engage the plurality of second element in the first configuration so as to create a space in which the medical implant is captured by the delivery system.

In some embodiments the plurality of first actuatable elements and the plurality of second elements are adapted such that by actuating the plurality of first actuatable elements the implant is released from the plurality of second elements.

In some embodiments the plurality of first actuatable elements and the plurality of second elements are adapted to engage to lock in the first configuration.

In some embodiments the plurality of first actuatable elements are adapted to be actuated with a proximally directed force which may be directed from outside of the body.

In some embodiments the plurality of actuatable elements are rigid elements, and in some embodiments the medical implant is an expandable anchor.

In some embodiments the system further comprises a restraining mechanism adapted to limit the expansion of the delivery system.

In some embodiments neither the plurality of first actuatable elements nor the plurality of second elements are adapted to be coupled to the implant in the first position.

In some embodiments the medical implant comprises an expandable braid.

One aspect of the invention is a capturing system adapted to releasably capture a medical implant in a delivery system, wherein the delivery system is adapted to deliver the medical implant through a body lumen. The coupling system includes a plurality of finger elements, and a plurality of actuatable elements each configured to slidably interface with one of the plurality of finger elements. Each of the plurality of actuatable elements is adapted to engage one of the plurality of finger elements in a first position so as to capture at least a portion of the medical implant, and each of the plurality actuatable elements is adapted to engage one of the plurality of finger elements in a second position to release the portion of the medical implant from the coupling system.

In some embodiments the plurality of finger elements and the plurality of actuatable elements are adapted to engage to lock together. The plurality of finger elements and the plurality of actuatable elements can be adapted to engage to lock in the first position and optionally in the second position.

In some embodiments the plurality of actuatable elements are adapted to be actuated by a proximally directed force. The actuatable elements can be adapted to be actuated to be unlocked from the plurality of finger elements. The actuatable element can comprise a lock element which is adapted to engage with the finger element to lock them together, the actuatable element further comprising a lock stop element adapted to prevent movement of the lock element after the actuatable element is unlocked from the first position. The lock element and the lock stop element can be shaped to mate. The plurality of actuatable elements are adapted to be actuated to be moved, such as by sliding on the second elements, from the unlocked position to the second position.

In some embodiments the plurality of actuatable elements are adapted to be locked in the second position by releasing an actuation force, such a proximally directed actuation force, on the plurality of actuatable elements.

In some embodiments the system further comprises a plurality of release actuators, which may comprise release actuator arrays, wherein the plurality of actuatable elements are adapted to be actuated by the plurality of release actuators.

In some embodiments the plurality of finger elements comprise an implant interface, which may be disposed near the distal end of the plurality of finger elements, and which may comprise a cavity adapted to receive the implant.

In some embodiments neither the plurality of actuatable elements nor the plurality of finger elements are adapted to be coupled to the implant.

In some embodiments the implant is released from the coupling system as the actuatable element is moved from the first position to the second position. The actuatable elements may include an ejection element, which may be disposed substantially at the distal end of the actuatable element, adapted to eject the implant from the finger element while the actuatable element is being moved from the first position to the second position, thus releasing the implant from the capturing system.

In some embodiments the plurality of finger elements comprise a restraining device adapted to limit expansion of the capturing system. The restraining device may pass through each of a set of holes in the plurality of finger elements, thereby coupling the plurality of finger elements and limiting the expansion of the plurality of finger elements.

In some embodiments the medical implant comprises an expandable braid.

One aspect of the invention is a method of endovascularly delivering and releasing a medical implant near a heart valve of a patient. The method comprises endovascularly delivering the medical implant to a location near or within a heart valve in a delivery configuration with a delivery system, preventing the implant from being released from the delivery system, wherein the delivery system comprises a plurality of first actuatable elements engaging a plurality of finger elements in a first configuration, and actuating the plurality of first actuatable elements such that the plurality of first actuatable elements engage the plurality of finger elements in a second configuration, thereby releasing the medical implant from the delivery system.

In some embodiments delivery of the medical implant includes expanding the delivery system from the delivery configuration to an expanded configuration. In some embodiments the expansion is limited by a restraining device.

In some embodiments preventing the implant from being released includes capturing at least a portion of the medical implant in a space between the finger element and the actuatable element.

In some embodiments actuating the plurality of first actuatable elements includes unlocking the plurality of actuatable elements from the plurality of finger elements. Unlocking can comprise applying a proximally directed force on the plurality of actuatable elements.

In some embodiments actuating the plurality of first actuatable elements includes sliding the plurality of actuatable elements on the exterior face of the finger elements. Sliding can comprise applying a proximally directed force to the plurality of actuatable elements.

In some embodiments releasing the medical implant from the delivery system includes ejecting the implant from the delivery system. Ejecting can comprise ejecting the implant from the delivery system as the plurality of actuatable elements move from the first configuration to the second configuration. Ejecting can comprise engaging a distal end of the actuatable element with at least a portion of the medical implant to release the medical implant from the finger element.

In some embodiments the method further includes releasing a proximally directed force applied to the plurality of actuatable elements, wherein releasing the proximally directed force relocks the plurality of actuatable elements with the plurality of finger elements.

BRIEF DESCRIPTION OF THE DRAWINGS

FIG. 1 illustrates the apparatus in a collapsed delivery configuration within a delivery system. FIG. 1B illustrates the apparatus in an expanded configuration partially deployed from the delivery system.

FIGS. 21A-21C show a variation of the post, actuator and release actuator that form an alternative releasable attachment mechanism.

FIGS. 23A-23C show yet another variation of the releasable attachment mechanism.

FIGS. 26A-26C show a variation of the actuator, lock actuator and release actuator.

FIGS. 30A and 30B show a variation of the post that is configured to lock against the braid of the anchor.

FIGS. 33A-33D show actuation of a variation of the anchor lock element that may be formed from a cut tube.

FIGS. 40A-40C show a tubular variation of the ratcheting lock element.

FIGS. 41A-41C show a variation of the anchor lock element of FIG. 40.

FIGS. 42A and 42B show a variation of the apparatus of FIG. 41 comprising a lock alignment feature.

FIGS. 43A-43F show a method of actuating and adjusting the ratcheting lock of the apparatus of FIG. 41.

FIGS. 45A-45C show detail views of the releasable attachment mechanism of the actuator of FIG. 44.

FIGS. 47A-47C show another variation of the releasable attachment mechanism.

FIGS. 49A-49N show variations of a release actuator used in conjunction with the releasable attachment mechanism of FIG. 45.

FIG. 58 is a side view shows an exemplary capturing system with a restraining device which limits the expansion of the delivery system.

FIG. 59 is an end view showing an expanded capturing system.

FIG. 60 is an end view showing an exemplary restraining device.

FIGS. 70 and 71 show an alternate embodiment in which a portion of a first actuatable element is reconfigured as a continuous spring element.

FIG. 72 shows an alternate embodiment of a release actuator.

FIG. 77 shows a release actuator array and an release actuator array tool.

FIG. 78 shows a plurality of release actuator arrays.

FIG. 79 shows a plurality of release actuator arrays in a stacked position.

DETAILED DESCRIPTION OF THE INVENTION

The present invention relates to apparatus and methods for endovascularly delivering and deploying a prosthesis, e.g., an aortic prosthesis, within and/or across a patient's native heart valve, referred to hereinafter as replacing the patient's heart valve. A delivery system and/or deployment tool is provided including a sheath assembly and a guidewire for placing the prosthetic apparatus endovascularly within the patient and a user control allowing manipulation of the prosthetic apparatus from external to the patient through the application of a non-hydraulically expanding or non-pneumatically expanding force on the anchor. A hydraulically or pneumatically expanding force would be, for example, a force applied to the anchor by a balloon expanded within the anchor. In certain embodiments, the application of a non-hydraulically expanding or non-pneumatically expanding force could include the use of a hydraulic component transmitting a proximally or distally directed force on an anchor.

The apparatus includes an anchor and a replacement valve. The anchor includes an expandable anchor such as a braid. In preferred embodiments, the expandable braid includes closed edges, but the edges may alternatively be open. The replacement valve is adapted to be secured within the anchor, and as such, be delivered endovascularly to the patient's heart to replace one of the patient's native heart valves. More preferably, the apparatus and methods of the present invention contemplate replacement of the patient's aortic valve.

Figure 1A:
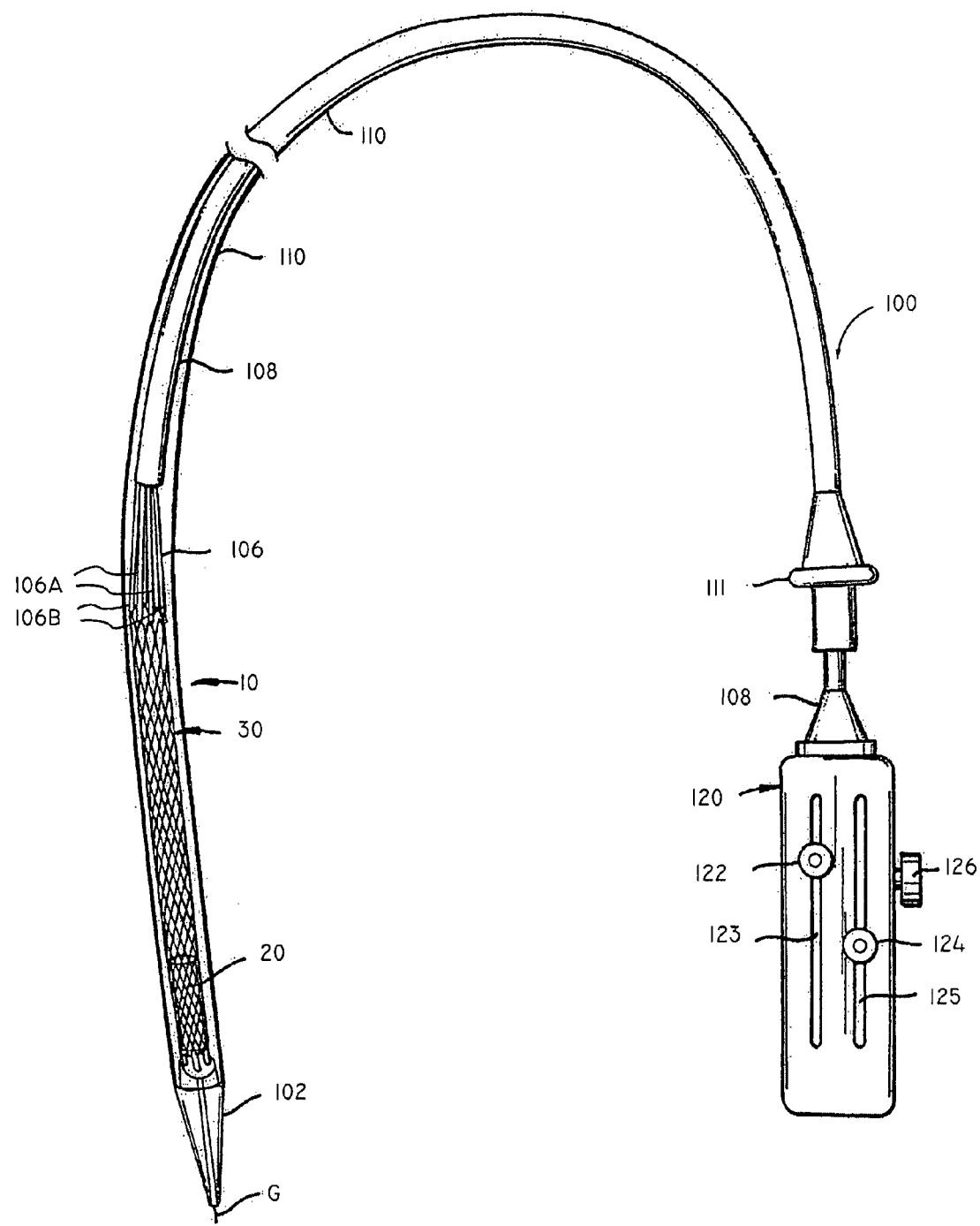
FIGS. 1A and 1B show replacement valve apparatus in accordance with the present invention.
Figures 1B, 2A:
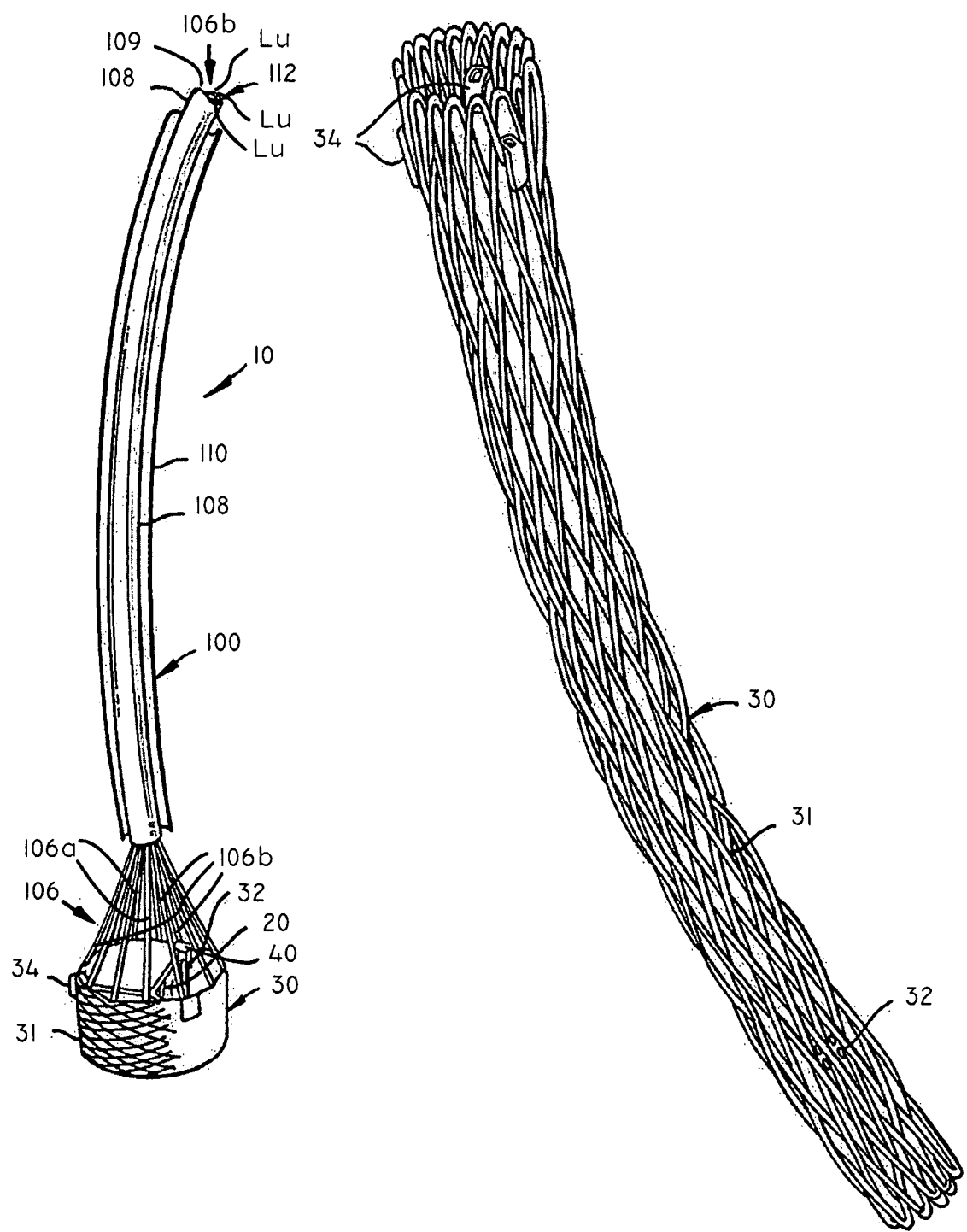
FIGS. 2A-2F show an anchor of the apparatus of FIG. 1 in the collapsed delivery configuration and the expanded deployed configuration, as well as the full apparatus in the deployed configuration, and optional locking mechanisms for use with the apparatus.

FIGS. 1A and 1B illustrate one embodiment of a delivery system/deployment tool and apparatus in accordance with the present invention. As seen in FIG. 1A, apparatus 10 may be collapsed for delivery within delivery system/deployment tool 100. Delivery system 100 includes guidewire G, nosecone 102, anchor actuation elements 106, multi-lumen shaft or catheter 108 having optional central lumen 109 and a plurality of circumferentially disposed lumens Lu, external sheath 110 having optional proximal handle 111, and control handle 120. Nosecone 102 may, for example, be manipulated via a shaft extending through central lumen 109 of multi-lumen catheter 108.

Anchor actuation elements 106 preferably comprise both proximal anchor actuation elements and distal anchor actuation elements. The proximal anchor actuation elements may, for example, comprise actuators 106a that are releasably coupled to a proximal region of anchor 30 of apparatus 10 via releasable attachment mechanisms for manipulating a proximal region of apparatus 10. The distal anchor actuation elements may comprise actuators 106b that are releasably coupled to a distal region of anchor 30 via releasable attachment mechanisms for manipulating the distal region of apparatus 10. In some embodiments, the distal anchor actuation elements may comprise posts or anchor attachment elements 32 of anchor 30 and the releasable attachment mechanisms connecting actuators 106b to posts 32. In an alternative configuration, the proximal anchor actuation elements may be releasably coupled to a proximal region of apparatus 10 through posts and releasable attachment mechanisms for manipulation of a proximal region of the apparatus, while the distal anchor actuation elements may connect to a distal region of anchor 30 via releasable attachment mechanisms to manipulate a distal region of the apparatus. As another alternative, both proximal and distal anchor actuation element may connect to anchor 30 via releasable attachment mechanisms.

In the embodiment shown in FIG. 1, actuators 106a may, for example, include stiff finger elements extending from a distal region of multi-lumen shaft 108, while actuators 106b may include control wires (e.g., stands of suture, or metal or polymer wires) which pass through one or more lumens Lu of shaft 108. Release actuators 112 for the releasable attachment mechanisms for both sets of actuators also may pass through one or more lumens Lu of shaft 108. The release actuators may comprise, for example, control wires (e.g., strands of suture, or metal or polymer wires), covers, mandrels, elongated elements, friction surfaces, wrap portions, interference shapes, etc. The release actuators preferably are movable relative to anchor actuation elements 106, e.g., via control handle 120.

Control handle 120 is coupled to multi-lumen shaft 108. Knob 122 disposed in slot 123 may actuate release actuators 112 that couple actuators 106a of anchor actuation elements 106 to apparatus 10. Likewise, knob 124 disposed in slot 125 may actuate release actuators 112 that couple actuators 106b of anchor actuation elements 106 to posts 32 of anchor 30 of apparatus 10. Handle 120 also comprises knob 126 for, e.g., manipulating the actuators 106b to control movement of the distal region of apparatus 10 relative to its proximal region. Conversely, controlled movement of the proximal region of apparatus 10 relative to its distal region may be achieved by holding knob 126 stationary while advancing or retracting handle 120. Knob 126 optionally may move actuators 106b in unison with their concomitant release actuators 112.

Apparatus 10 comprises anchor 30 and replacement valve 20. Anchor 30 preferably comprises a braid. Such braid can have closed ends at either or both its ends. Replacement valve 20 is preferably coupled to the anchor along posts 32, e.g., along a valve attachment structure, such as a tab and/or a plurality of holes. Posts 32, therefore, may function as valve supports and may be adapted to support the replacement valve within the anchor. In the embodiment shown, there are three posts, corresponding to the valve's three commissural attachment points. The posts can be attached to the braid portion of anchor 30. The posts can be attached to the braid's distal end, as shown in FIG. 2A, central region, or proximal end. Replacement valve 20 can be composed of a synthetic material and/or may be derived from animal tissue. Replacement valve 20 is preferably configured to be secured within anchor 30.

Figure 2B:
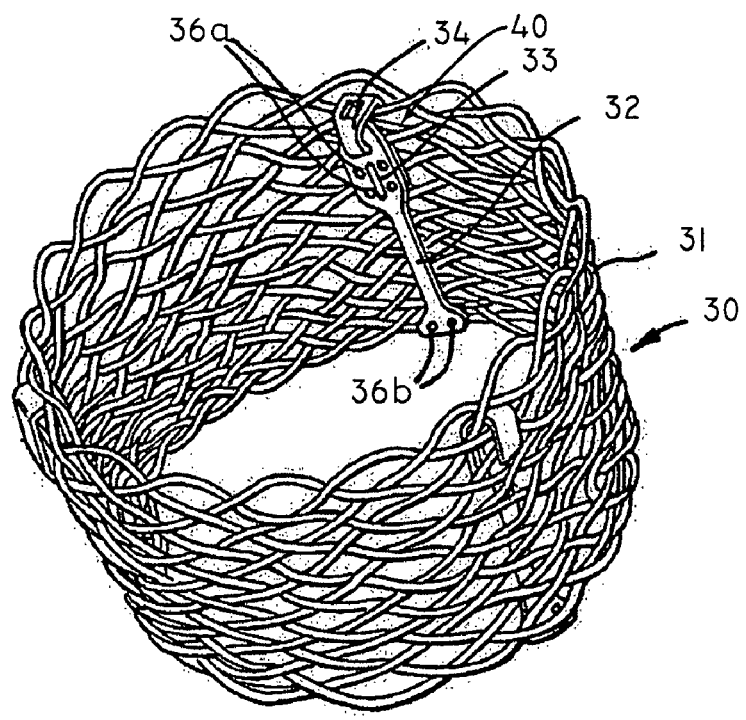
Figure 2C:
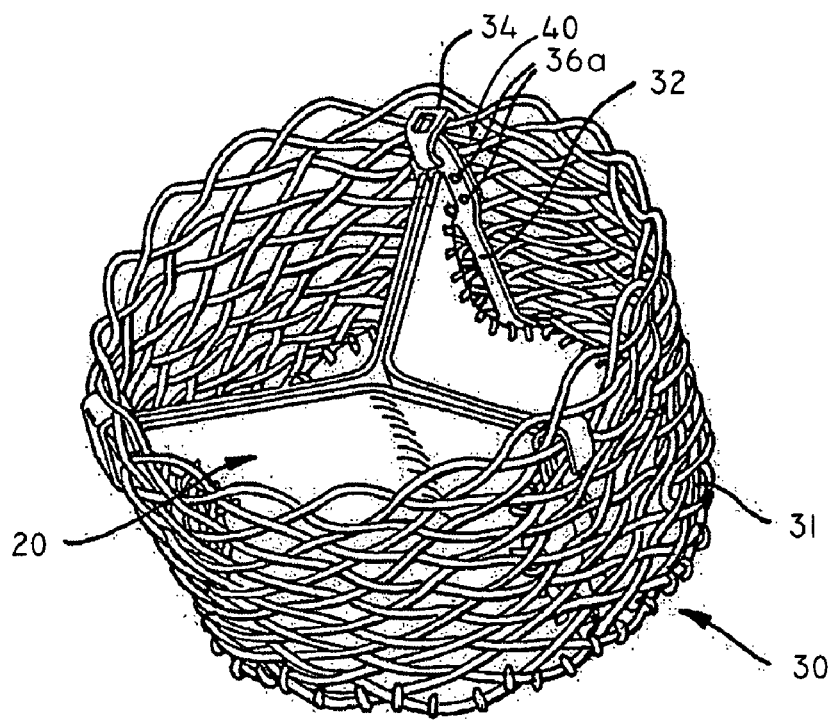

Anchor 30 comprises a plurality of anchor lock elements 34, e.g., buckles 34, attached to its proximal region, one for each post 32. Posts 32 may comprise a lock element that forms a two-part locking mechanism with anchor lock elements 34 for maintaining anchor 30 in a deployed or expanded configuration (e.g., as illustrated in FIGS. 1B, 2B and 2C).

In this embodiment, anchor 30 is formed from a collapsible and expandable wire braid. Anchor braid 30 is preferably self-expanding and is preferably formed from a material such as Nitinol, cobalt-chromium steel or stainless steel wire using one or more strands of wire. Delivery and deployment of braided anchor 30 is similar to the delivery and deployment of the anchors described in U.S. patent application Ser. No. 10/746,120. Specifically, in one embodiment described below, during deployment braided anchor 30 is actively foreshortened by proximally retracting the actuators 106b relative to the actuators 106a to expand and lock the anchor in place. In some embodiments, foreshortening may expand anchor 30 to a radially symmetrical, bilaterally symmetrical, or asymmetrical expanded shape. The foreshortening step can include expanding a first region of the anchor to a first diameter and a second region of the anchor to a second diameter larger than the first diameter. A third region may also be expanded to a diameter larger than the first diameter. The expansion of various regions of the anchor (e.g., the distal region) can be especially useful in locating the aortic valve and centering the anchor within it. Preferably, the secured anchor does not interfere with the mitral valve or the ostia. In some embodiments, the anchor is allowed to self-expand prior to the foreshortening step.

As seen in FIG. 1, after endovascular delivery through sheath 110 to the vicinity of the patient's native valve (such as the aortic valve), apparatus 10 may be expanded from the collapsed delivery configuration of FIG. 1A to the expanded deployed configuration of FIG. 1B using delivery system/deployment tool 100. To deploy apparatus 10, external sheath 110 may be retracted relative to apparatus 10 by proximally retracting sheath handle 111 relative to control handle 120. Sheath 110 is thereby removed from the exterior of apparatus 10, permitting the anchor 30 to self-expand. For example, if anchor braid 30 is composed of a shape memory material, it may self-expand to or toward its "at-rest" configuration. This at-rest configuration of the braid can be, for example its expanded configuration, a collapsed configuration, or a partially expanded configuration between the collapsed configuration and the expanded configuration, or some combination. In preferred embodiments, the anchor's at-rest configuration is between the collapsed configuration and the expanded configuration. Depending on the at-rest diameter of the braid and the diameter of the patient's anatomy at the chosen deployment location, the anchor may or may not self-expand to come into contact with the diameter of the patient's anatomy at that location.

In its collapsed configuration, anchor 30 preferably has a collapsed delivery diameter between about 3 to 30 Fr, or more preferably 6 to 28 Fr, or more preferably 12 to 24 Fr. In some embodiments, anchor 30 in its collapsed configuration will have a length ranging from about 5 to about 170 mm, more preferably from about 10 to about 160 mm, more preferably from about 15 to about 150 mm, more preferably from about 20 to about 140 mm, or more preferably from about 25 mm to about 130 mm.

Similarly, in its expanded configuration, anchor 30 preferable has a diameter ranging between about 10 to about 36 mm, or more preferably from about 24 to about 33 mm, or more preferably from about 24 to about 30 mm. In some embodiments, anchor 30 in its expanded configuration will have a length ranging from about 1 to about 50 mm, more preferably from about 2 to about 40 mm, more preferably from about 5 to about 30 mm, or more preferably from about 7 to about 20 mm.

Overall, the ratio of deployed to collapsed/sheathed lengths is preferably between about 0.05 and 0.5, more preferably about 0.1 to 0.35, or more preferably about 0.15 to 0.25. In any of the embodiments herein, anchor 30 in its expanded configuration preferably has a radial crush strength that maintains the anchor substantially un-deformed in response to a pressure of up to about 0.5 atm directed substantially radially inward toward the central axis, or more preferably up to about 2 atm directed substantially radially inward toward the central axis. In addition, in any of the embodiments herein, the anchor preferably has an axial spring constant of between about 10 to 250 g/cm, more preferably between about 20 to 200 g/cm, or more preferably between about 40 to 160 g/cm. In addition, in any of the embodiments herein, the anchor is preferably adapted to support the replacement valve at the anchor site in response to a differential pressure of up to about 120 mm Hg, more preferably up to about 240 mm Hg, or more preferably up to about 320 mm Hg.

These parameters are not intended to be limiting. Additional parameters within the scope of the present invention will be apparent to those of skill in the art.

As seen in FIG. 1B, anchor 30 may be expanded to a fully deployed configuration from a partial deployed configuration (e.g., self-expanded configuration) by actively foreshortening anchor 30 during endovascular deployment. In some embodiments, foreshortening of the apparatus involves applying a distally directed force on the proximal end of the anchor by one or more anchor actuation elements to move the proximal end of the anchor distally while maintaining the position of the distal end of the anchor. For example, the proximal region of anchor 30 may be pushed distally by certain anchor actuation elements 106, e.g., actuators 106a. Alternatively, foreshortening of the apparatus involves applying a proximally directed force on the distal end of the anchor by one or more anchor actuation elements to move the distal end of the anchor proximally while maintaining the position of the proximal end of the anchor. For example, the distal region of anchor 30 may be pulled proximally via a proximally directed force applied by post actuation elements 106b, this force opposed by anchor actuators 106a.

Anchor actuation elements 106 preferably are adapted to expand radially as the anchor expands radially and to contract radially as the anchor contracts radially. Furthermore, proximally or distally directed forces by the anchor actuation elements on one end of the anchor do not diametrically constrain the opposite end of the anchor. In addition, when a proximally or distally directed force is applied on the anchor by the anchor actuation elements, it is preferably applied without passing any portion of a deployment system through a center opening of the replacement valve. This arrangement enables the replacement valve to operate during deployment and before removal of the deployment system.

The distal anchor actuation elements may include, for example, actuators 106b and/or release actuators 112 that are controlled, e.g., by control knobs 124 and 126 of control handle 120. Similarly, the proximal regions of anchor 30 may be pushed distally via proximal anchor actuation elements, e.g., actuators 106*a*, at the proximal region of the anchor. The proximal anchor actuation elements facilitate application of a distally directed force to the proximal end of anchor 30 to move or constrain the proximal end of the anchor distally and are controlled through motion of shaft 108 relative to the distal anchor actuation elements. Control knob 122 of control handle 120 may control release actuators 112 for releasing the proximal anchor actuation elements from the braid. The proximal anchor actuation elements may be further adapted to expand as the proximal end of the anchor expands radially during application of a distally directed force on the proximal end of the anchor. Preferably, the proximal anchor actuation elements apply a distally directed force on the proximal end of the anchor system through a plurality of actuators 106*a* in order to expand the braid of anchor 30. Such braid expansion optionally may be assisted via inflation of a balloon catheter (see FIGS. 12 and 13) reversibly disposed within apparatus 10, as described in U.S. patent application Ser. No. 10/746,120.

In the fully deployed configuration, lock elements of posts 32 and anchor lock elements or buckles 34 of anchor 30 may be used to lock and maintain the anchor in the deployed configuration. Apparatus 10 may be repositioned or retrieved from the patient until the lock elements of posts 32 have been interlocked with anchor lock elements 34 of anchor 30 to form lock 40. In one embodiment, actuators 106*b* and attendant release actuators 112 comprise control wires attached to posts 32 that are threaded through buckles 34 so that the proximally directed force exerted on posts 32 by the control wires during deployment pulls a lock element of posts 32 toward and through buckles 34 to form lock 40. In this manner, the control wires may act as both anchor actuators and lock actuators.

Such lock optionally may be selectively reversible to allow for repositioning and/or retrieval of apparatus 10 during or post-deployment. When the lock is selectively reversible, the apparatus may be repositioned and/or retrieved as desired, i.e., even after actuation of lock 40.

Locks used herein may also include a plurality of levels of locking wherein each level of locking results in a different amount of expansion. For example, the anchor lock elements at the proximal end of the post can have multiple configurations for locking within the buckle wherein each configuration results in a different amount of anchor expansion (see, e.g., FIG. 2F). Such locking mechanisms may, for example, comprise ratchets having multiple lock locations. Furthermore, lock alignment features may be provided to facilitate alignment of the post and anchor lock elements, such as a hinge or an oversized width of the post or anchor lock elements. Further still, lock prevention mechanisms may be provided to preclude locking until desired by a medical practitioner.

When apparatus 10 is placed across a patient's diseased heart valve, anchor 30 may be used to displace the patient's native valve leaflets, and replacement valve 20 will thereafter serve in place of the native valve. After final positioning and expansion, apparatus 10 may be decoupled from delivery system 100 by decoupling the proximal and distal anchor actuation elements 106 from the apparatus via releasable attachment mechanisms, e.g., by decoupling proximal actuators 106*a* from braided anchor 30 and distal actuators 106*b* from posts 32 of the anchor via the releasable attachment mechanisms. Moving release actuators 112, e.g., using knobs 122 and 124 of handle 120, may, for example, actuate the releasable attachment mechanisms. Preferably, the releasable attachment mechanisms may be actuated by moving the release actuator(s) less than about 1 inch. After decoupling, delivery system/deployment tool 100 may be removed from the patient, thereby completing endovascular replacement of a patient's heart valve.

Prior to implantation of replacement valve apparatus described herein, it may be desirable to perform a valvuloplasty on the patient's diseased valve by inserting a balloon into the valve and expanding it using, e.g., saline mixed with a contrast agent. In addition to preparing the valve site for implant, fluoroscopic viewing of the valvuloplasty will help determine the appropriate size of replacement valve implant to use.

FIGS. 2A-2C show further details of anchor 30 of apparatus 10. FIG. 2A shows the apparatus in a collapsed configuration, such as for delivery within a sheath or other lumen or for retrieval and recapture into a sheath or other lumen. FIGS. 2B and 2C show the anchor and valve in an expanded and locked configuration.

As shown in FIG. 2B, anchor 30 illustratively has three posts and three buckles. As seen in FIG. 2C, the three leaflets of replacement valve 20 may be coupled to the three posts 32 along valve support structures. Thus, posts 32 act as valve supports. The posts, unlike the braid, do not collapse or expand. In some embodiments, a post 32 has one or more proximal slots 33, at least one proximal hole 36*a* and at least one distal hole 36*b*. Leaflet tissue may, for example, be passed through slot 33 and sutured in place via suture routed through one or more proximal holes 36*a*. In this manner, slot(s) 33 and hole(s) 36*a* may form a valve support structure. Alternative valve support structures known in the art for fixing valve leaflets to posts may also be employed.

Posts 32 may be coupled to anchor braid 30 via one or more distal holes 36*b*. For example, anchor braid 30 may be woven through holes 36*b*, or a suture or wire may be routed through holes 36*b* and tied to the braid. Yet another proximal hole (not shown) in post 32 serves as an anchor lock element that interfaces with the anchor lock element provided by buckle 34 to form lock 40. Buckles 34 may likewise be attached to anchor braid 30 via weaving or suturing.

Figure 2D:
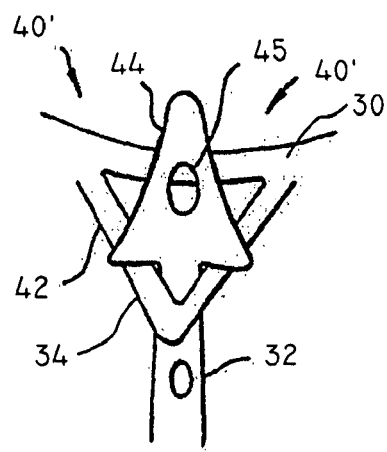
Figure 2E:
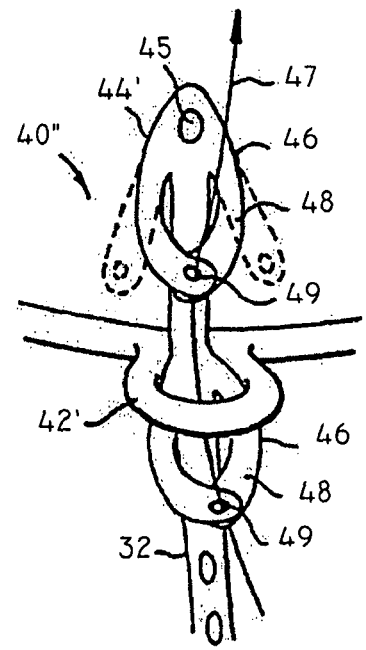
Figure 2F:
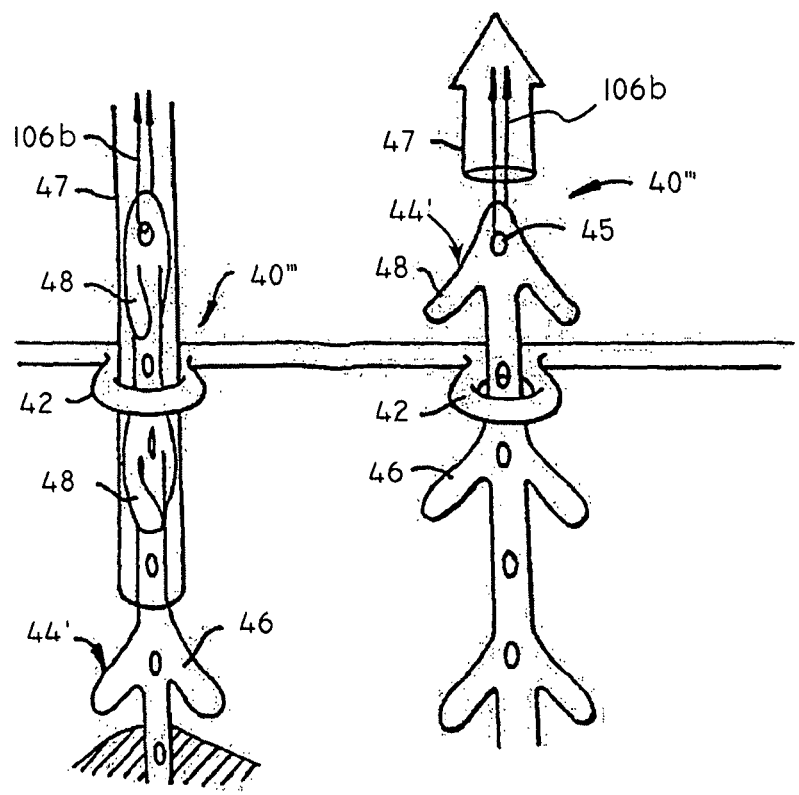

Alternative locks may be used to lock the anchor of the present invention in the foreshortened configuration, as shown, e.g., in FIGS. 2D-2F. Preferably, a lock of the present invention can have multiple locking options such that locking can confer a plurality of amounts of expansion. Furthermore, the locking option can be employed asymmetrically to confer non-cylindrical shapes to the anchor. In FIG. 2D, lock 40' comprises male lock element 44 disposed on post 32 and anchor lock element 34 disposed on braided anchor 30. Anchor lock element 34 illustratively comprises triangular protrusion or eyelet 42 of anchor 30. The triangular shape of female lock element 42 may facilitate mating of male lock element 44 with the female lock element without necessitating deformation of the male lock element. One or more holes 45 may be provided through post 32, e.g., for releasably attaching an actuator 106*b* to the post.

In FIG. 2E, lock 40" comprises alternative male lock element 44' having multiple inline arrowheads 46 along posts 32. Each arrowhead comprises resiliently deformable appendages 48 to facilitate passage through female lock element 42', which illustratively comprises a rounded eyelet. Appendages 48 optionally comprise holes 49, such that releasable lock prevention mechanism 47, illustratively a control wire, may pass through the holes to constrain the appendages in the deformed configuration. To actuate lock 40", one or more arrowheads 46 of male lock element 44' are drawn through female lock element 42', e.g., via a post/lock actuator, and the lock prevention mechanism is removed from holes 49, thereby causing appendages 48 to resiliently expand and actuate lock 40".

Advantageously, providing multiple arrowheads 46 along posts 32 yields a ratchet that facilitates in-vivo determination of a degree of foreshortening and expansion imposed upon anchor 30. Furthermore, optionally constraining appendages 48 of arrowheads 46 via mechanism 47 prevents actuation of lock 40" (and thereby deployment of apparatus 10) even after male element 44' has been advanced through female element 42'. Only after a medical practitioner has removed lock prevention mechanism 47, which constrains appendages 48, is lock 40" fully engaged and is deployment no longer reversible.

Lock 40''' of FIG. 2F is similar to lock 40" of FIG. 2E, except that holes 49 on appendages 48 have been eliminated, and the lock prevention mechanism comprises overtube or cover 47. Overtube 47 constrains appendages 48 to prevent locking until a medical practitioner has determined that apparatus of the present invention has been foreshortened and positioned adequately at a treatment site. Lock 40''' may, for example, be actuated by applying a proximally-directed force to actuator 106b. Actuator 106b illustratively comprises a control wire releasably disposed through hole 45 in post 32. Lock prevention mechanism 47 then is withdrawn proximally relative to anchor 30, which causes the appendages to resiliently expand, thereby fully actuating lock 40'''.

Referring now to FIG. 3 in conjunction with FIGS. 1 and 2, a method of endovascularly replacing a patient's diseased aortic valve with apparatus 10 and delivery system/deployment tool 100 is described. As seen in FIG. 3A, sheath 110 of delivery system 100, having apparatus 10 disposed therein, is endovascularly advanced over guidewire G, preferably in a retrograde fashion (although an antegrade or hybrid approach alternatively may be used), through a patient's aorta A to the patient's diseased aortic valve AV. Nosecone 102 precedes sheath 110 in a known manner. In FIG. 3B, sheath 110 is positioned such that its distal region is disposed within left ventricle LV of the patient's heart H.

Figure 3A:
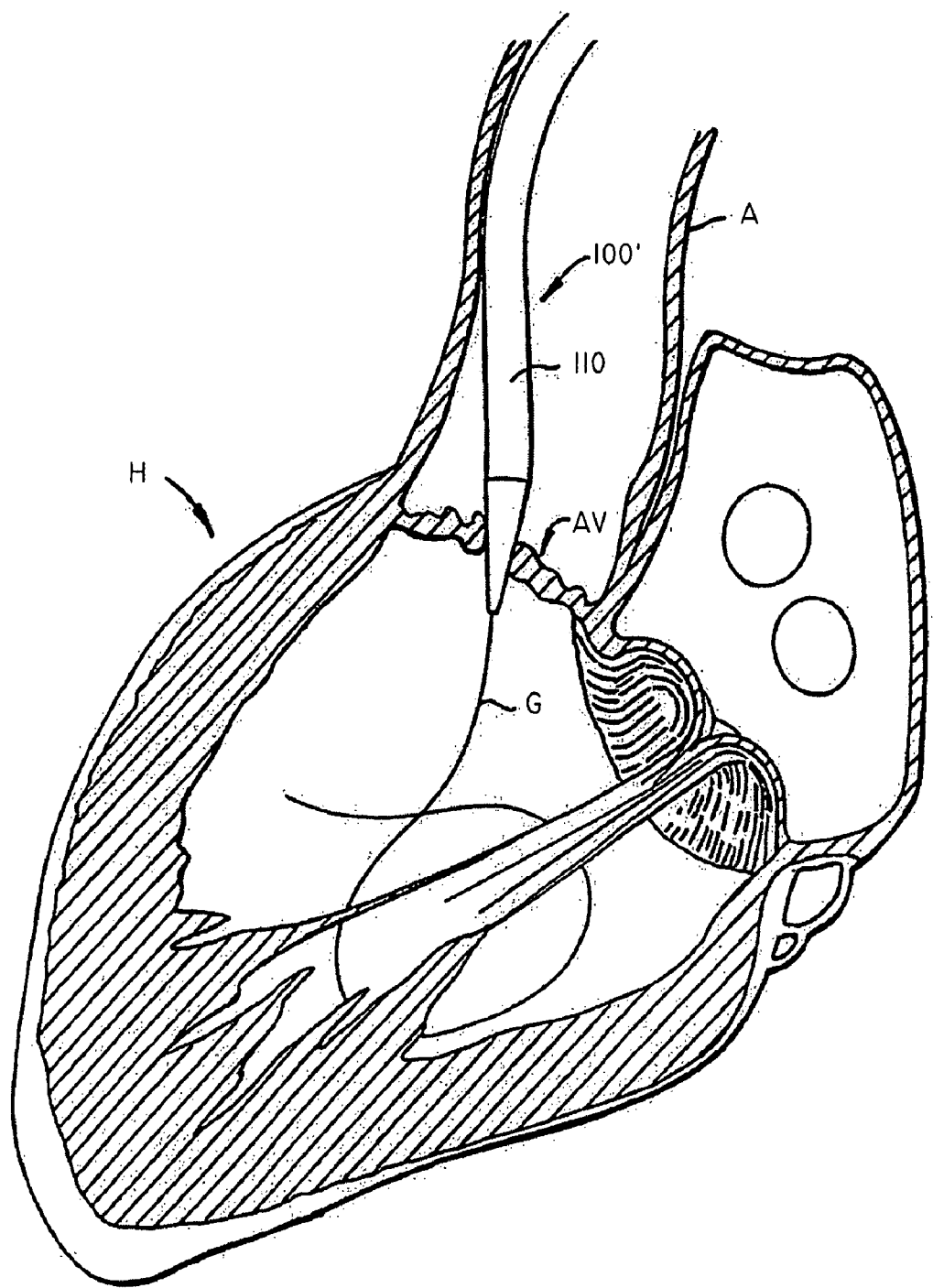
FIGS. 3A-3E show the use of a replacement heart valve and anchor to replace an aortic valve.
Figure 3B:
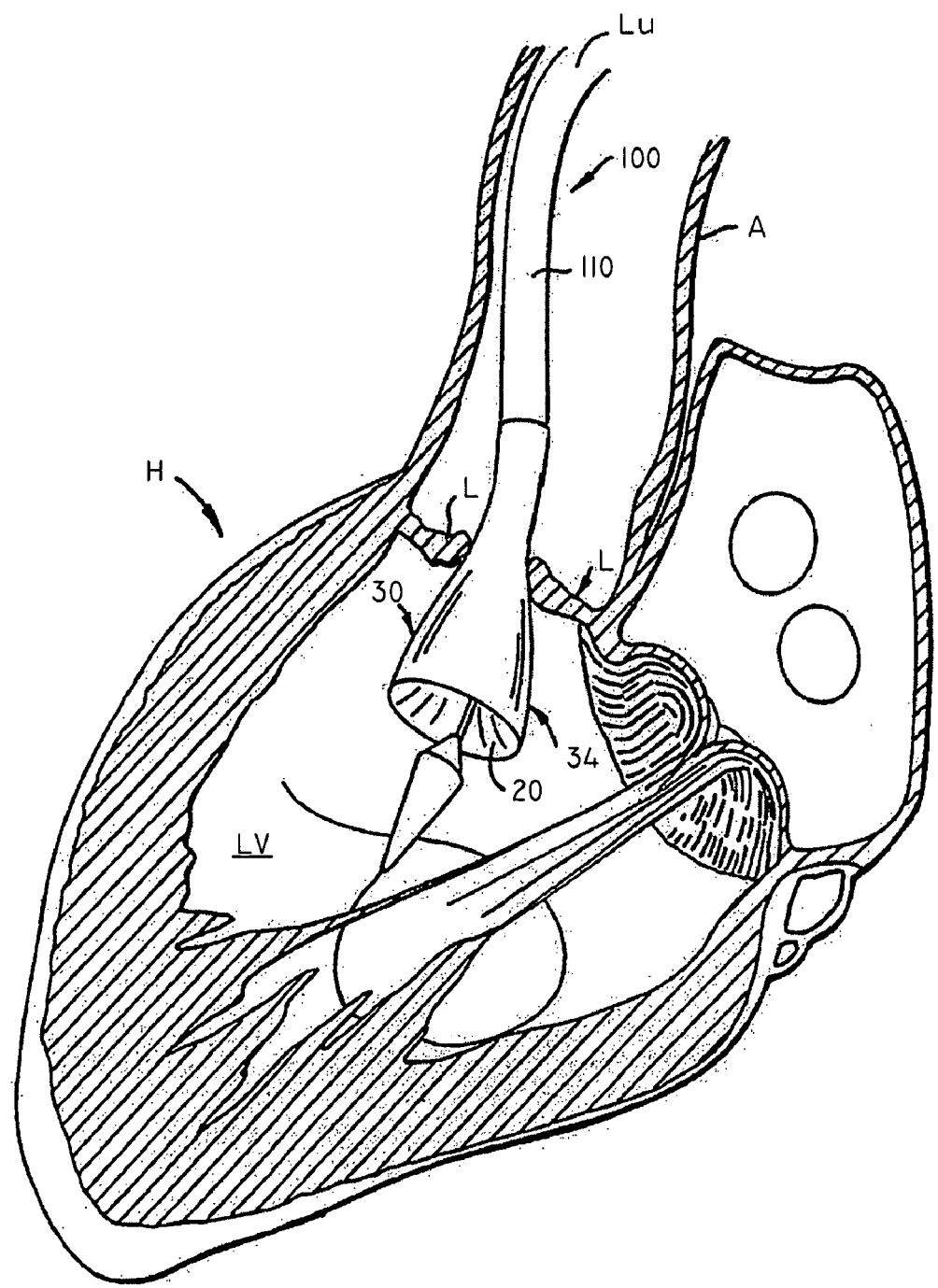
Figure 3C:
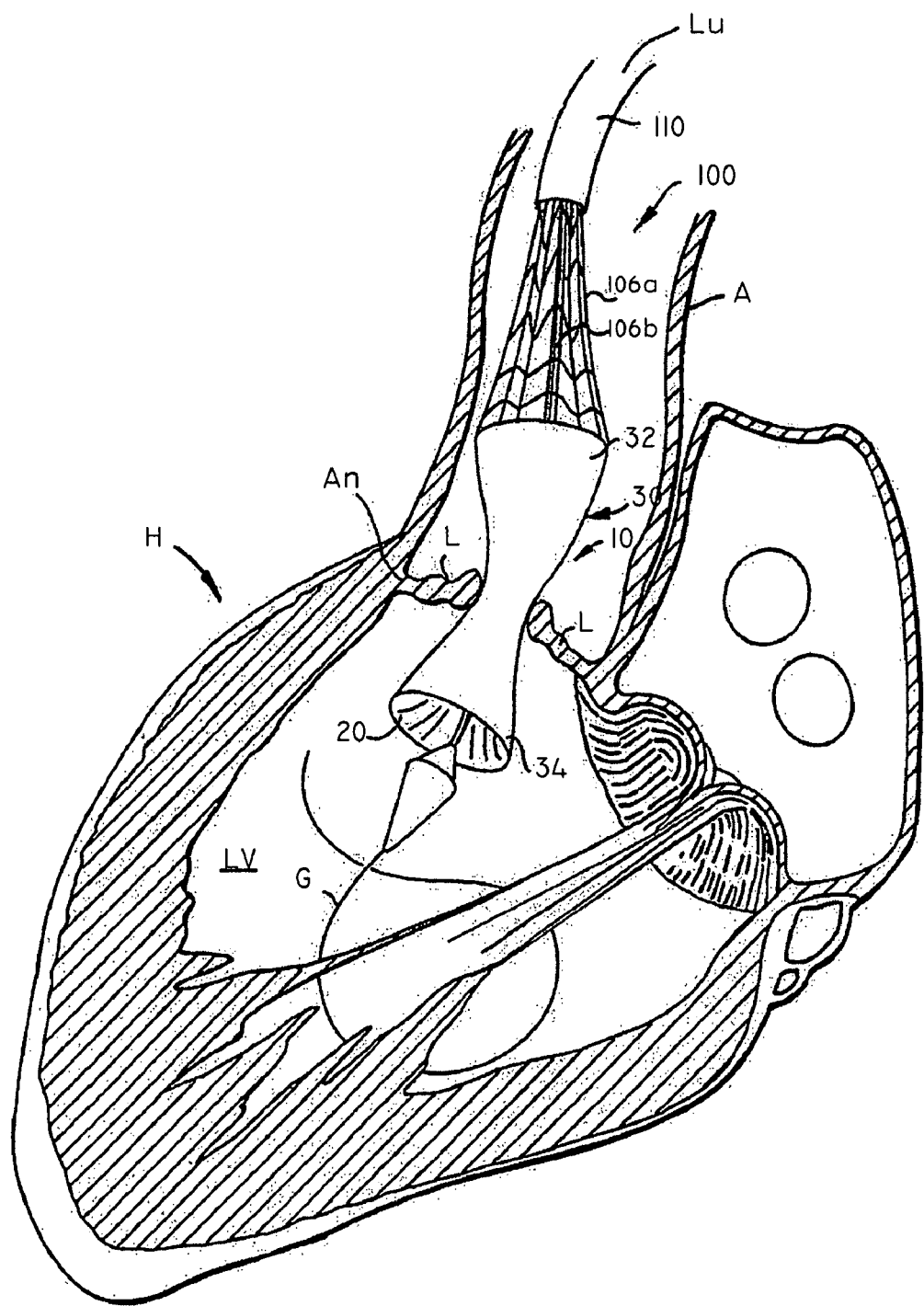

Apparatus 10 is deployed from lumen Lu of sheath 110, for example, under fluoroscopic guidance by proximally retracting proximal handle 111 of sheath 110 relative to shaft 108, such that anchor 30 of apparatus 10 dynamically self-expands to the partially deployed configuration of FIG. 3C. Advantageously, apparatus 10 may be retracted within lumen Lu of sheath 110 by retracting shaft 108 relative to the sheath, and thereby retracting actuators 106a coupled to anchor 30 relative to sheath 110. In this manner, anchor 30 may be retrieved even after the anchor has dynamically expanded to the partially deployed configuration, for example, to abort the procedure or to reposition apparatus 10 or delivery system 100. As yet another advantage, apparatus 10 may be dynamically repositioned, in order to properly align the apparatus relative to anatomical landmarks, such as the patient's coronary ostia or the patient's native valve leaflets L. When properly aligned, a distal region of anchor 30 preferably is disposed distal of the leaflets, while a central region of the anchor is disposed across the leaflets and a proximal region is disposed proximal of the leaflets.

Figure 3D:
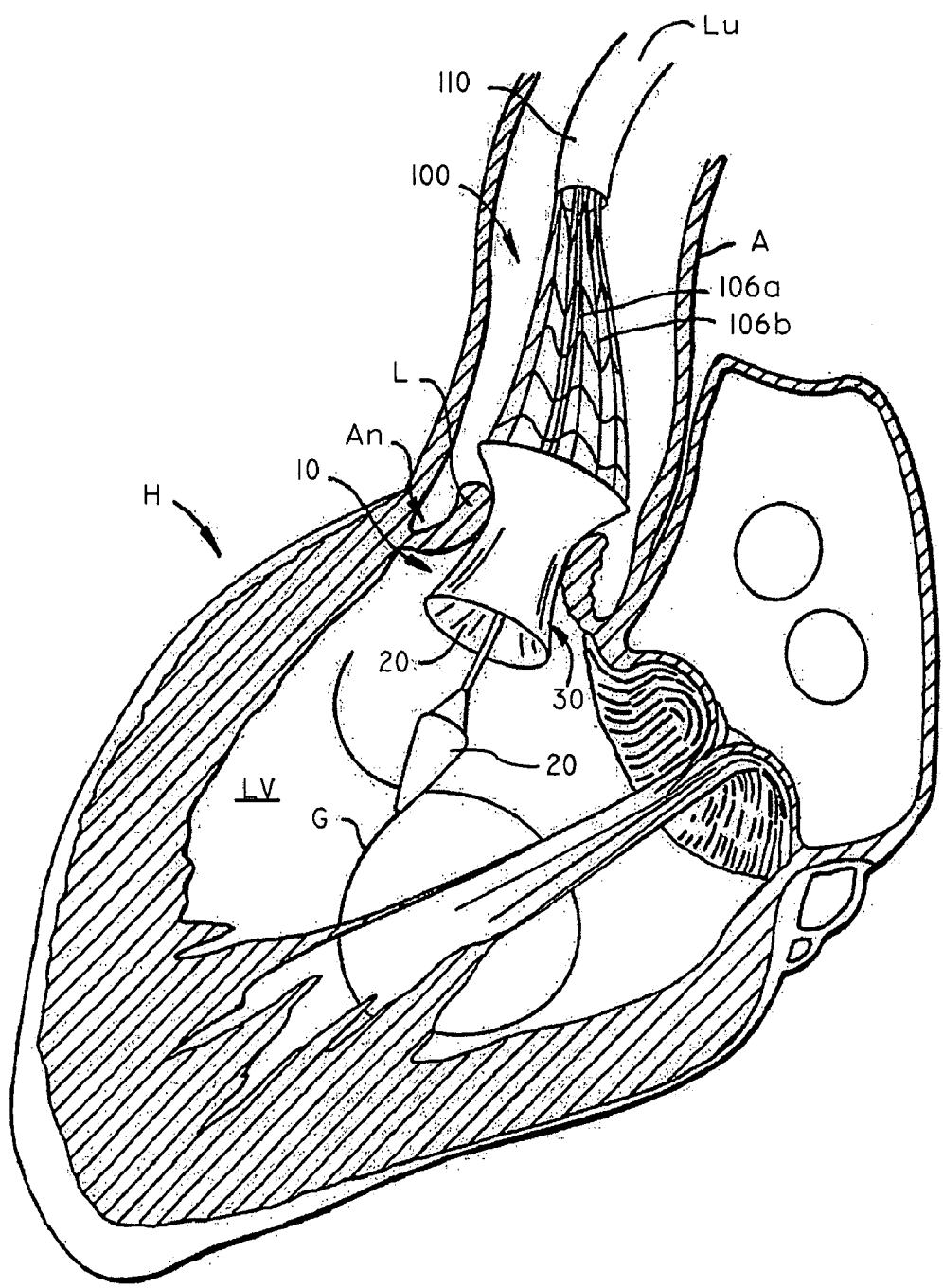

Once properly aligned, actuators 106b are proximally retracted relative to actuators 106a, e.g., via knob 126 of handle 120, to impose foreshortening upon anchor 30 and further expand apparatus 10 to the fully deployed configuration, as in FIG. 3D. Foreshortening increases the radial strength of anchor 30 to ensure prolonged patency of valve annulus An, as well as to provide a better seal for apparatus 10 that reduces paravalvular regurgitation. Lock 40 formed by engaging post lock elements 44 of posts 32 with anchor lock elements 34 of anchor 30 maintains imposed foreshortening. Replacement valve 20 is properly seated within anchor 30, and normal blood flow between left ventricle LV and aorta A is thereafter completely regulated by apparatus 10, although valve 20 is functional during deployment as well. Deployment of apparatus 10 advantageously is fully reversible until the locks have been actuated. Releasable lock prevention mechanisms may be provided to ensure that the locks are not actuated prematurely. Furthermore, the locks may be reversible, such that apparatus 10 may be retrieved or repositioned even after actuation of the locks.

Figure 3E:
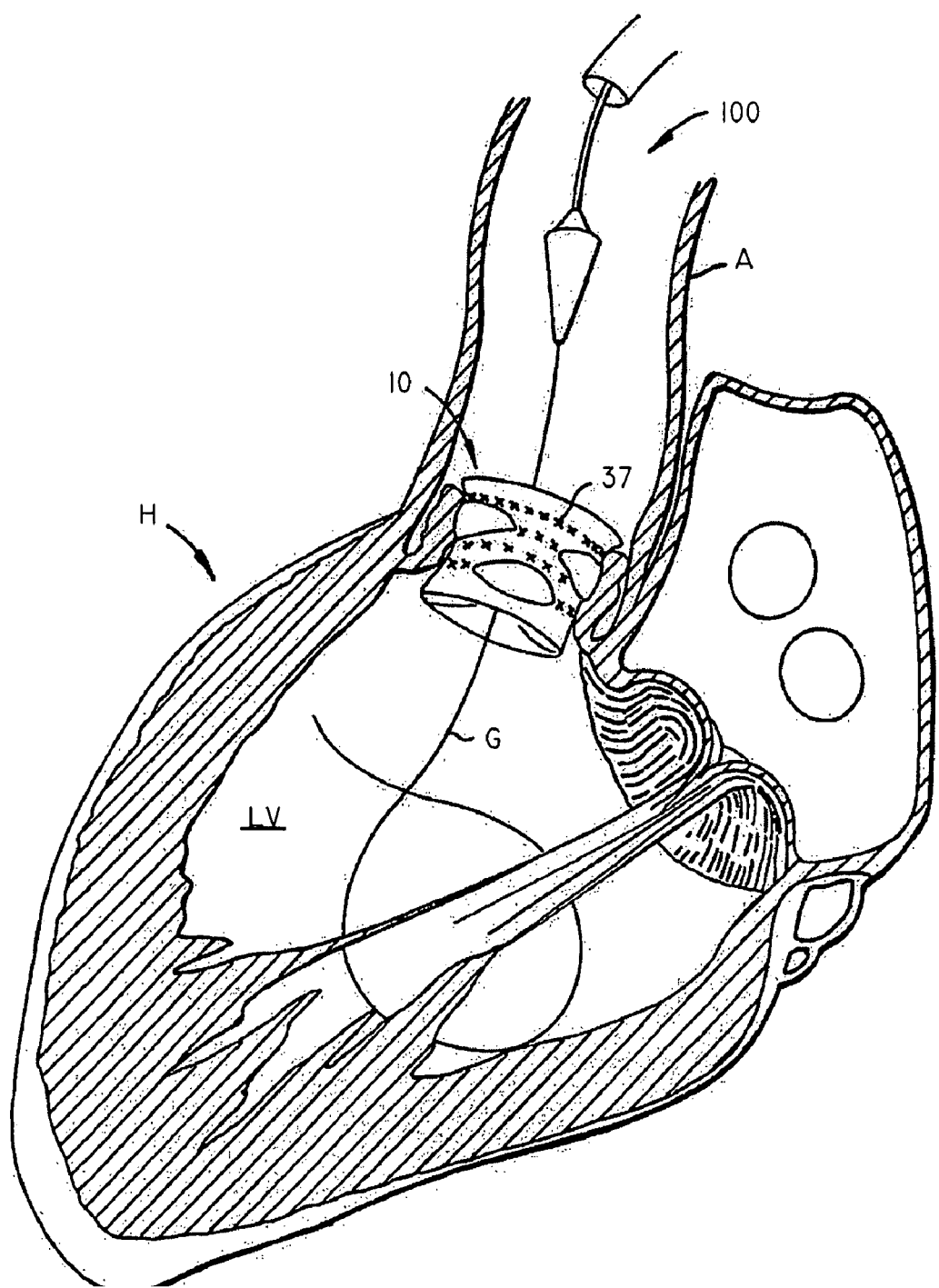

Once apparatus 10 is fully expanded and locked in the expanded configuration, actuators 106a are decoupled from anchor 30 by actuating releasable attachment mechanisms, e.g., by retracting release actuators 112 relative to the actuators 106a via knob 122 of handle 120. Likewise, actuators 106b are decoupled from posts 32 by actuating releasable attachment mechanisms, e.g., by retracting release actuators 112 relative to the actuators 106b via knob 124 of handle 120. As seen in FIG. 3E, delivery system 100 then may be removed from the patient, thereby completing deployment of apparatus 10. Optional barb elements 37 engage the patient's native valve leaflets, e.g. to preclude migration of the apparatus and/or to reduce paravalvular regurgitation.

Figure 4A:
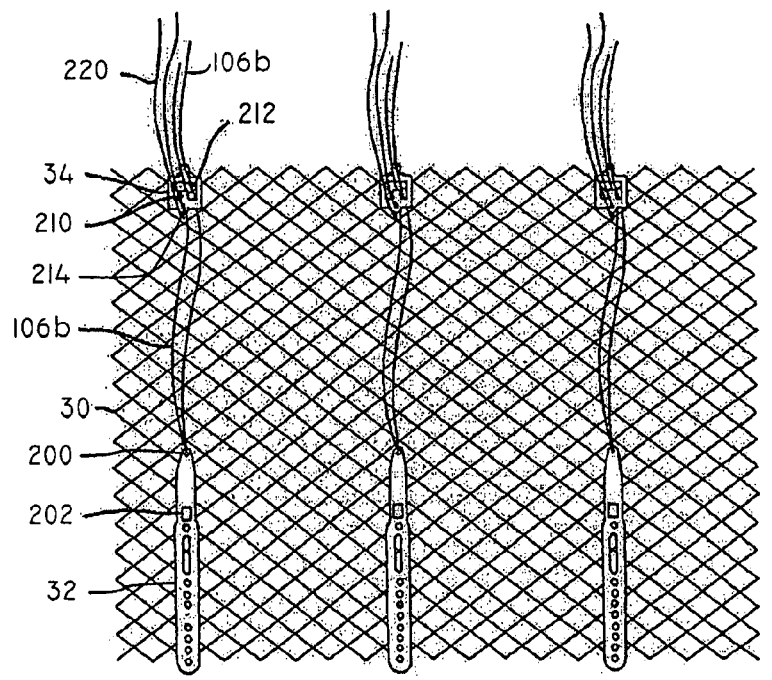
FIGS. 4A and 4B show an alternative anchor lock embodiment in an unlocked configuration.
Figure 4B:
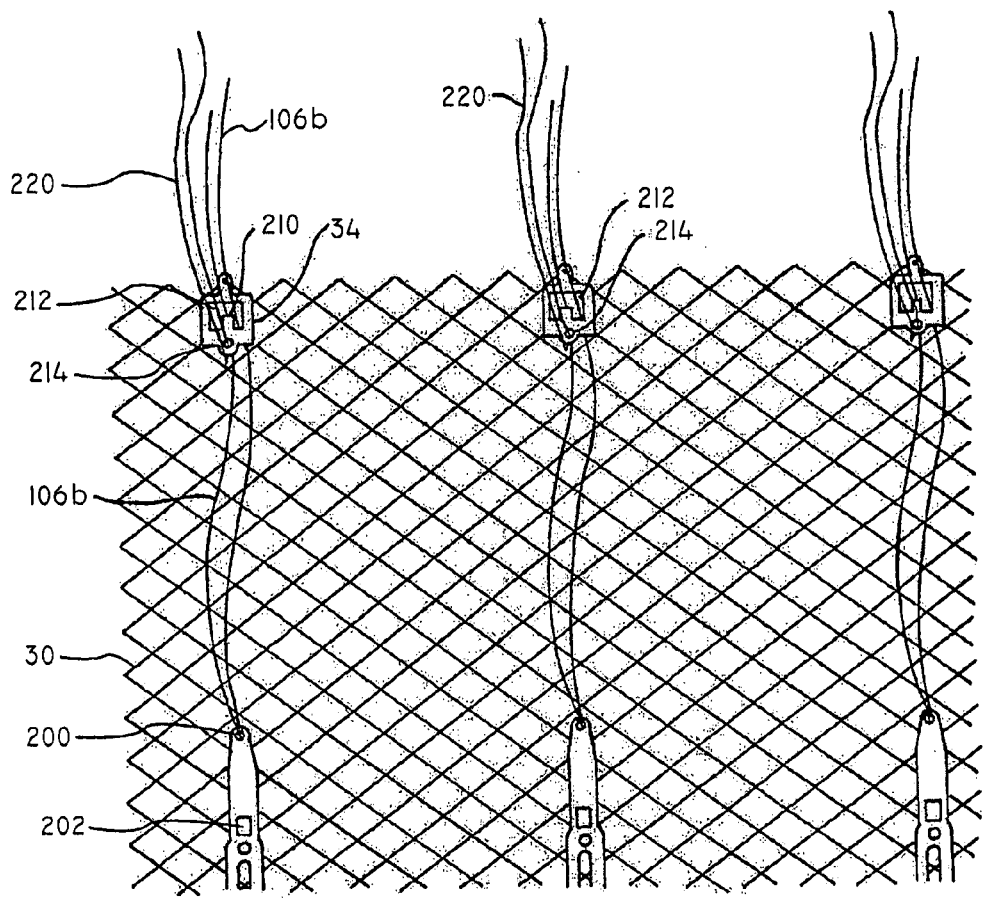
Figure 5A:
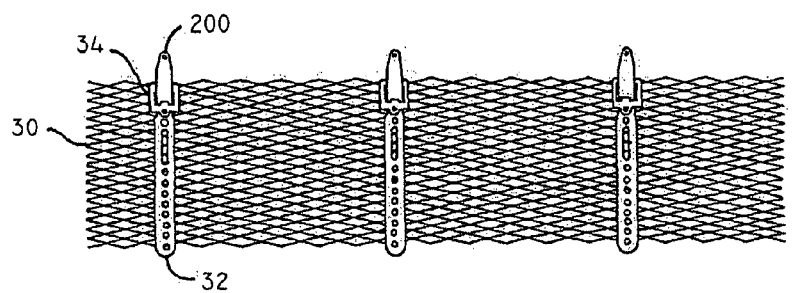
FIGS. 5A and 5B show the anchor lock of FIG. 4 in a locked configuration.
Figure 5B:
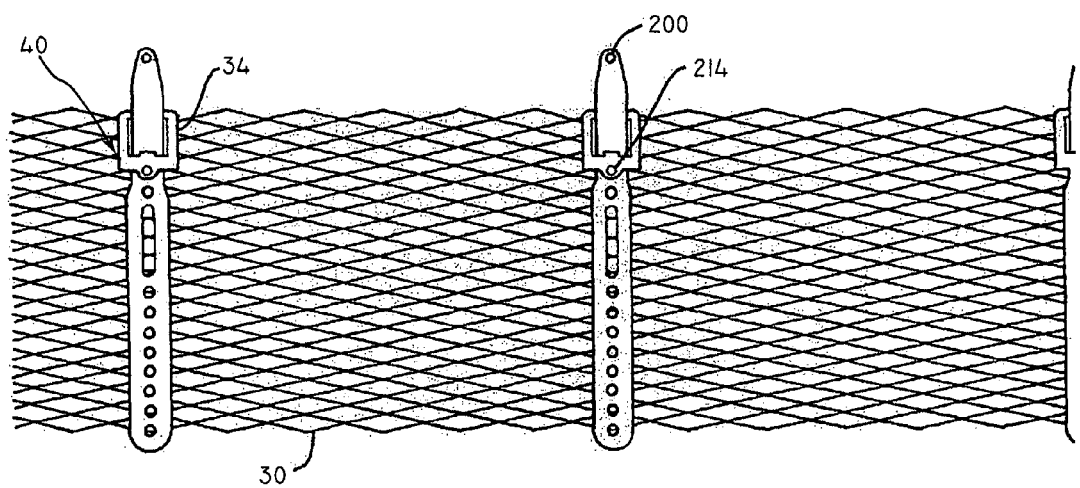

FIGS. 4 and 5 illustrate anchor lock mechanisms depicted in FIG. 4 in the locked configuration. FIGS. 4 and 5 should be viewed as if cylindrical anchor 30 has been cut open and laid flat. Posts 32 coupled to anchor 30 illustratively comprise actuator attachment elements 200 and lock elements 202, e.g., eyelets or holes formed through the posts. Anchor 30 comprises anchor lock elements 34, illustratively buckles, which are configured to mate with lock elements 202 of the posts. Posts 32 and buckles 34 may, for example, be connected to braided anchor 30 by inter-weaving the posts and the buckles into the braid of the anchor. Alternatively, the posts and/or buckles may be sutured, soldered, welded, connected with adhesive, etc., to the anchor. The commissures of previously described replacement valve 20 may be connected to posts 32 along all or a portion of their lengths.

Lock elements 202 of posts 32 mate with tabs 210 extending into holes 212 in anchor lock elements 34. To lock, actuators 106b, which releasably pass through actuator attachment elements 200 of posts 32 and holes 212 of anchor lock elements 34, are pulled proximally by anchor actuators 106b (illustratively control wires) with respect to the proximal end of braided anchor 30 to draw posts 32 through holes 212 so that tabs 210 engage lock elements 202 of posts 32. Also shown are unlocking actuators 220, illustratively control wires, which pass through anchor lock eyelets 214 in anchor lock elements 34. If needed, during the procedure, the user may pull on unlocking actuators 220, thereby reversing orientation of tabs 210, releasing the anchor and allowing for repositioning of the device or its removal from the patient. Only when final positioning as desired by the operating physician is achieved, would unlocking actuators 220, as well as actuators 106b, be removed from apparatus 10 and the patient.

Figure 6:
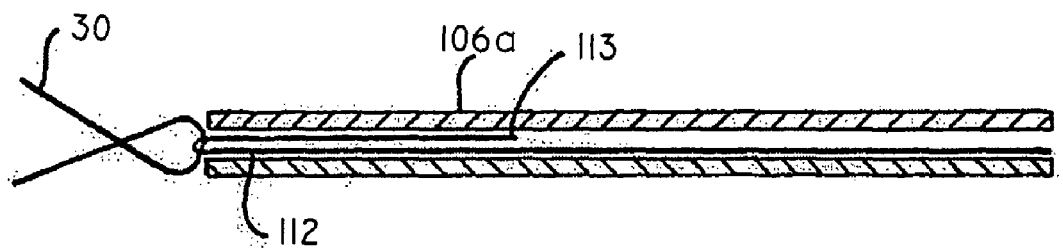
FIG. 6 shows an alternative anchor deployment tool attachment and release mechanism for use with the invention.
Figure 7:
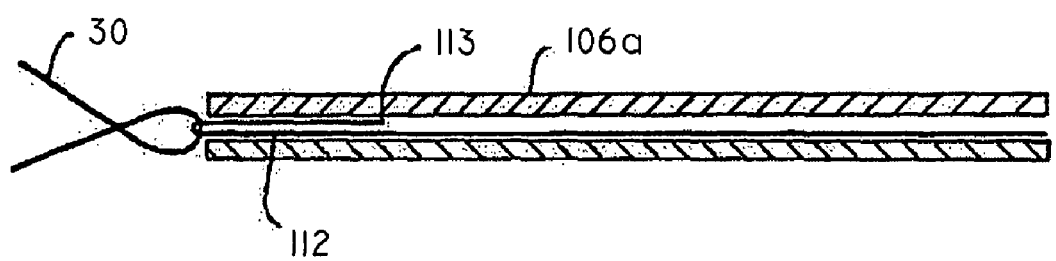
FIG. 7 shows the attachment and release mechanism of FIG. 6 in the process of being released.
Figure 8:
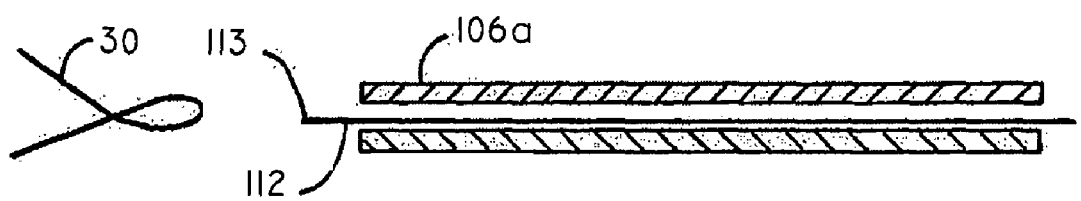
FIG. 8 shows the attachment and release mechanism of FIGS. 6 and 7 in a released condition.

Referring now to FIGS. 6-8, an alternative way of releasing the connection between the anchor (or post, etc.) and the anchor actuation elements is described. In FIG. 6, release actuator 112, illustratively a control wire, extends through actuator 106a from outside the patient, loops through the proximal region of braided anchor 30 and extends partially back into actuator 106a. The doubled up portion of release actuator 112 creates a force fit within actuator 106a that maintains the release actuator's position with respect to the actuator 106a when all release actuators 112 within actuators 106a are pulled proximally, e.g., when applying a proximally directed force on anchor 30. When a single release actuator 112 is pulled proximally, however, the frictional fit between that release actuator and the actuator 106a in which it is disposed is overcome, enabling the end 113 of release actuator 112 to pull free of actuator 106a, as shown in FIGS. 7 and 8, thereby releasing anchor 30. In an alternative embodiment, the doubled up portion of release actuator 112 may extend proximally to, e.g., control handle 120. In such an embodiment, expansion of anchor 30 may be achieved by proximally retracting both ends of the doubled up release actuator 112 via the control handle, while release of actuator 106a may be achieved by pulling on one end of release actuator 112.

Figure 9:
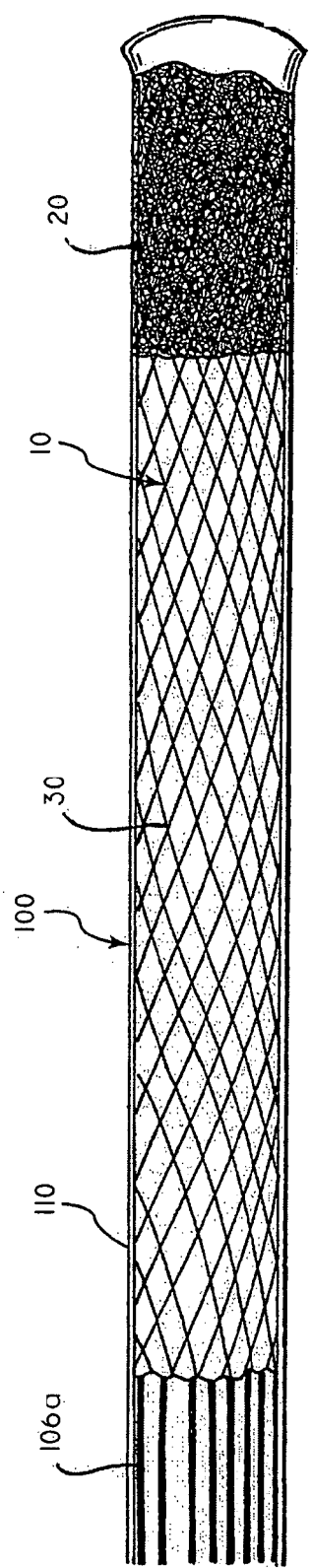
FIG. 9 shows an alternative embodiment of a replacement heart valve and anchor and a deployment tool according to the invention in an un-deployed configuration.
Figure 10:
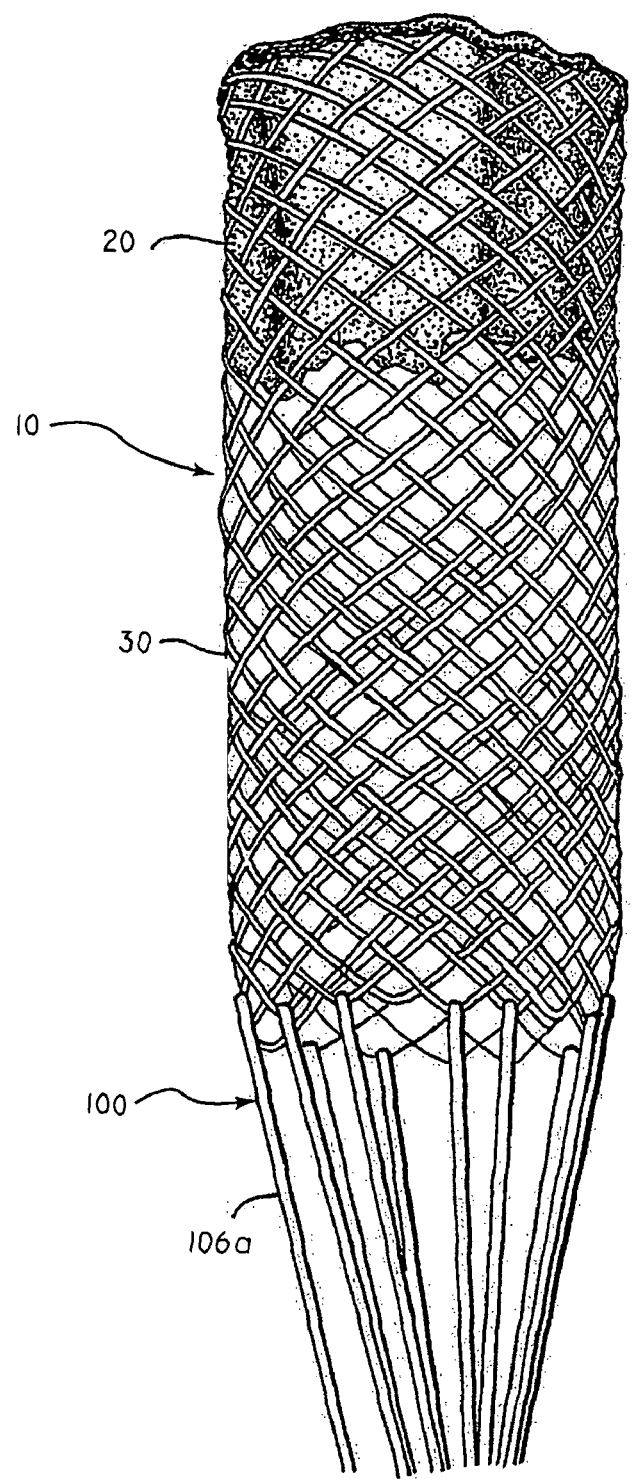
FIG. 10 shows the replacement heart valve and anchor of FIG. 9 in a partially deployed configuration.
Figure 11:
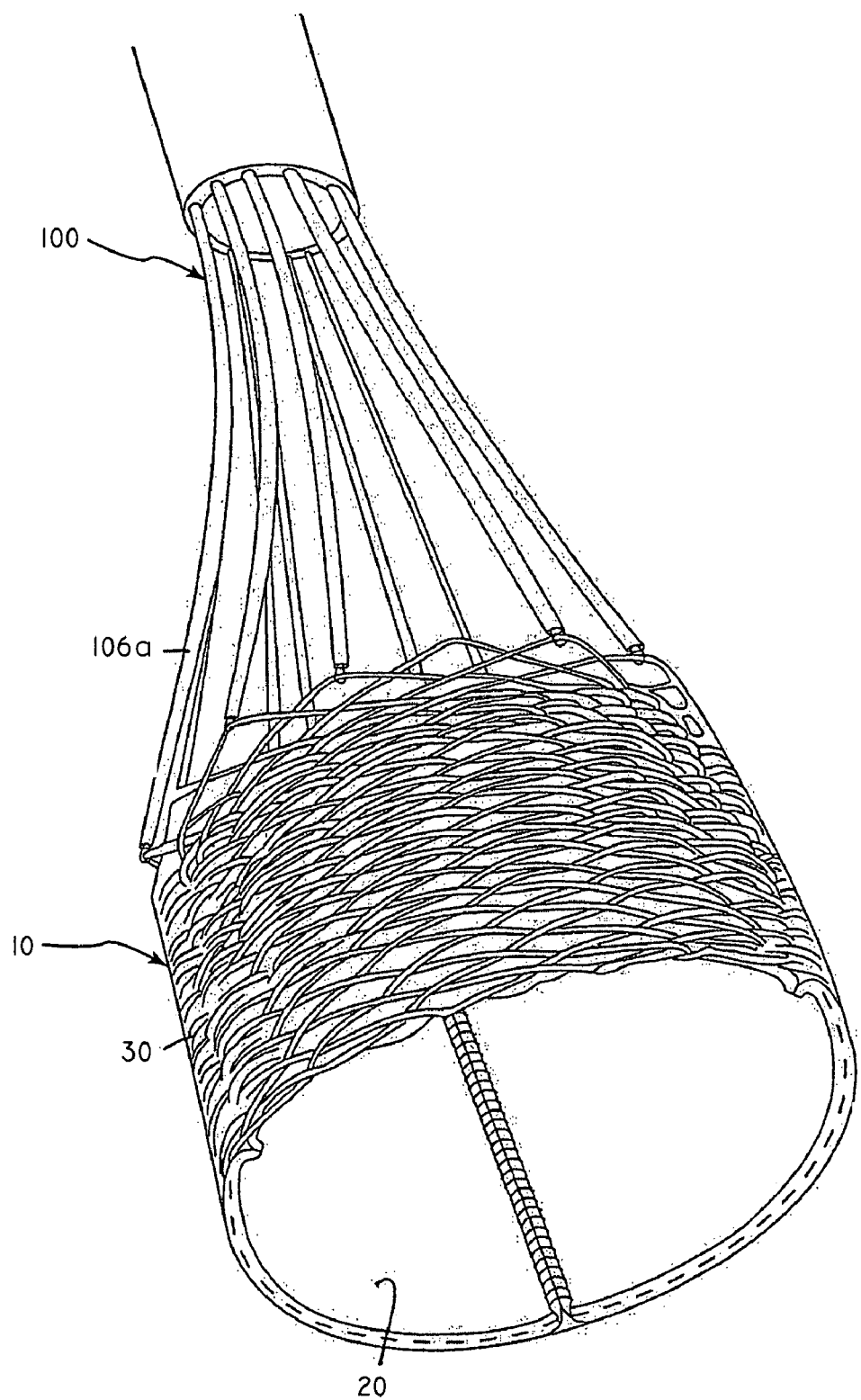
FIG. 11 shows the replacement heart valve and anchor of FIGS. 9 and 10 in a more fully deployed configuration but with the deployment tool still attached.

FIGS. 9-11 show additional views of apparatus 10. Anchor 30 is made of a metal braid, such as Nitinol or stainless steel. Replacement valve 20 is disposed within anchor 30. Anchor 30 is actuated in substantially the same way as described previously through the application of proximally and distally directed forces from distal anchor actuators (not shown) and actuators 106a.

Figure 12:
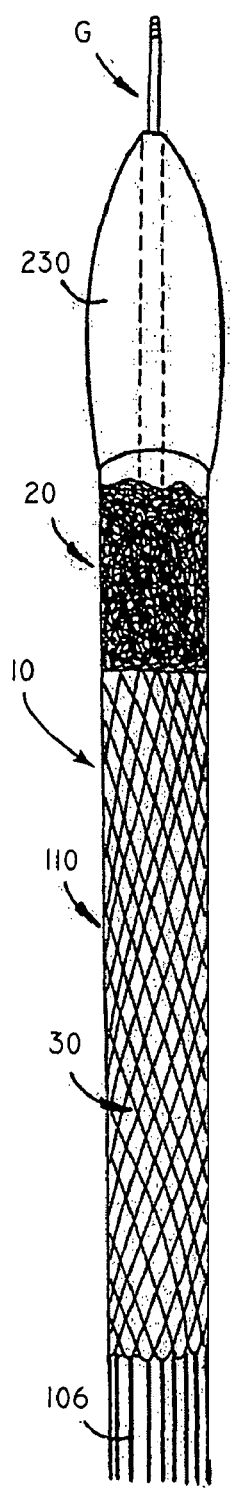
FIG. 12 shows yet another embodiment of the delivery and deployment apparatus of the invention in use with a replacement heart valve and anchor.
Figure 13:
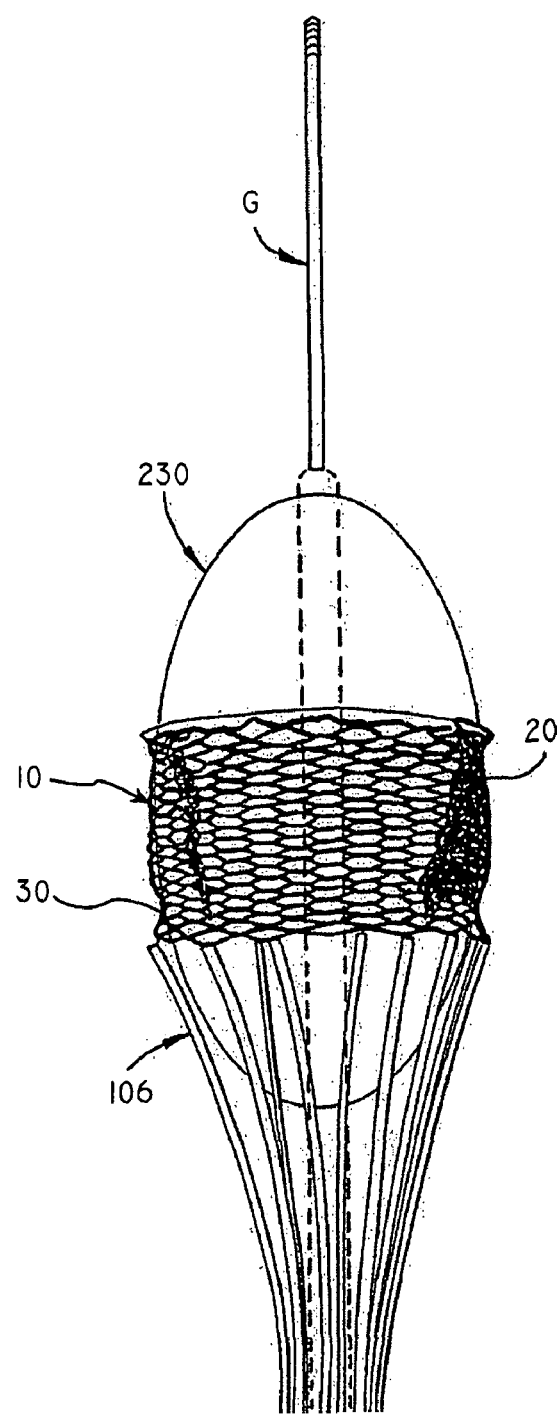
FIG. 13 shows the delivery and deployment apparatus of FIG. 12 in the process of deploying a replacement heart valve and anchor.

FIGS. 12 and 13 show another embodiment of the delivery and deployment apparatus of the invention. In this embodiment, the nosecone (e.g., element 102 of FIGS. 1A and 3) is replaced by angioplasty balloon catheter 230. Thus, angioplasty balloon catheter 230 precedes sheath 110 on guidewire G. When anchor 30 and valve 20 are expanded through the operation of anchor actuation elements 106 as described above, balloon catheter 230 is retracted proximally within the expanded anchor and valve and may be inflated to further expand the apparatus 10, as desired. Optionally, a separate balloon catheter or valvuloplasty catheter may be advanced within apparatus 10 after expansion thereof to achieve additional expansion of the apparatus.

Figure 14:
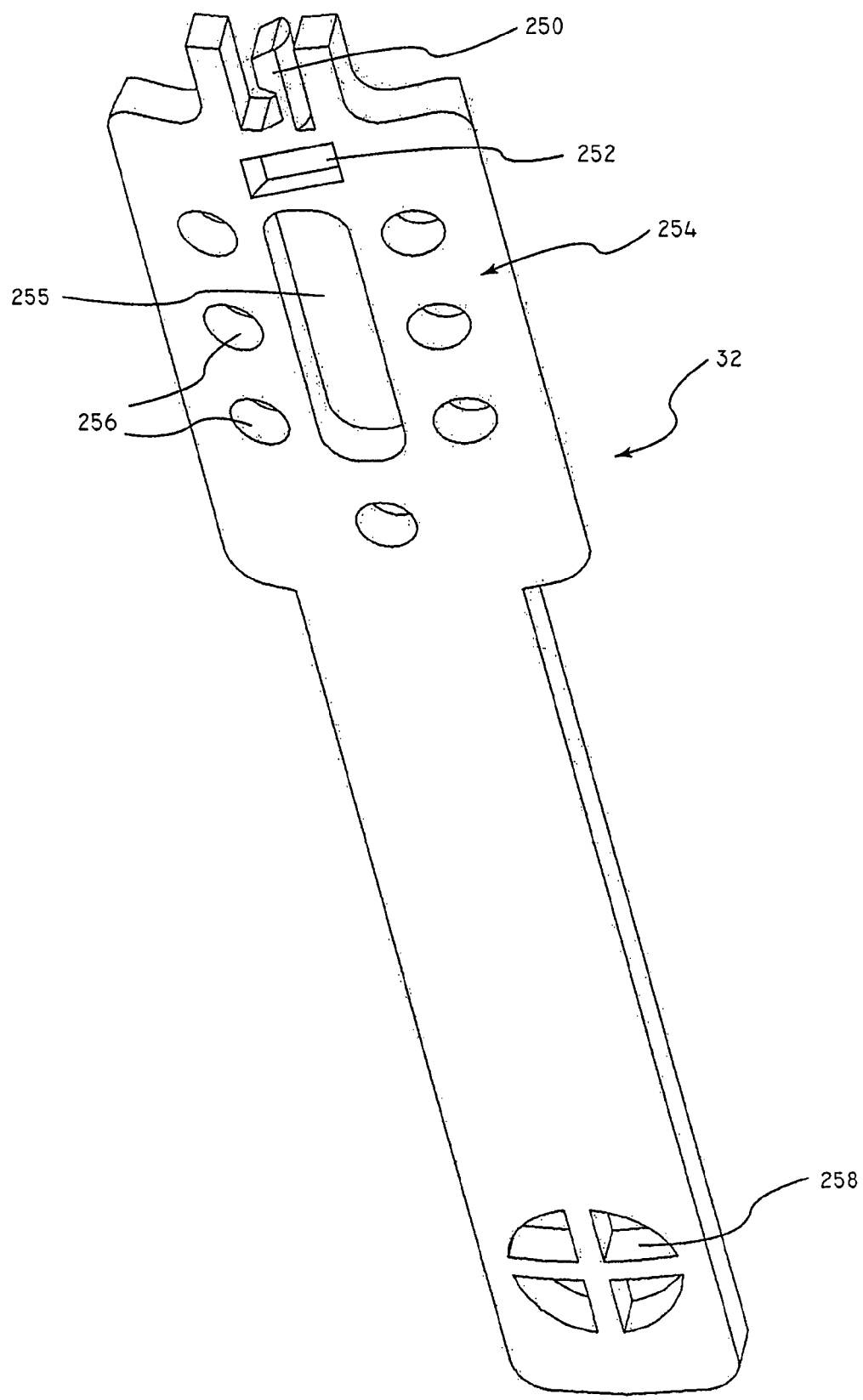
FIG. 14 shows a detail view of a variation of an anchor post.

Referring now to FIG. 14, a detail view of a variation of post 32 is described. In FIG. 14, post 32 illustratively comprises actuator attachment element 250 for attaching the post to an actuator 106b; post lock element 252, illustratively a slot, for interlocking post 32 with an anchor lock element 34; valve attachment structure 254, comprising slot 255 and a plurality of holes 256, for attaching replacement valve 20 to the post (a tab of the valve may be passed through slot 255, then sewn to the back of the post through holes 256); and braid attachment element 258 for attaching the post to a distal region of anchor 30. The braid of anchor 30 may, for example, be interwoven through braid attachment element 258. Post 32 may be fabricated from a variety of materials, e.g., metallic materials such as stainless steel, and may be laser cut, die cast, etc. In this variation of post 32, valve 20 is disposed distal of lock element 252. In alternative variations, the valve may be attached to the post proximal of the lock element or inline with the lock element (i.e., neither proximal nor distal to the lock).

Figures 15A, 15B, 16A, 16B:
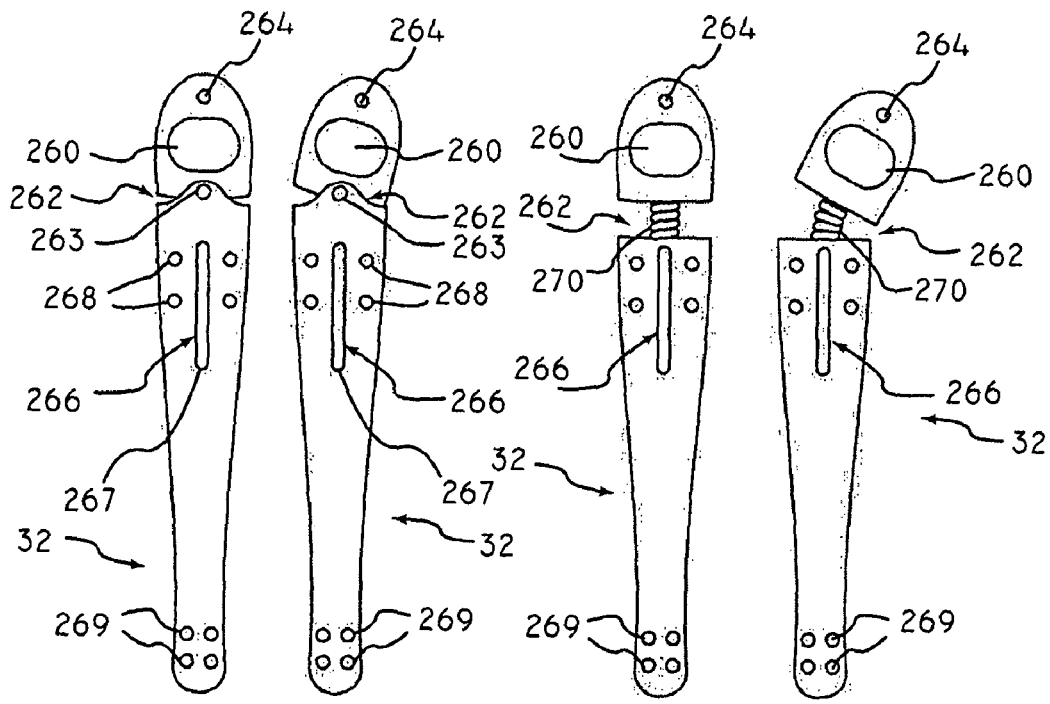
FIGS. 15A and 15B show an alternative variation of the post having a lock alignment feature.
FIGS. 16A and 16B show a variation of the post having an alternative lock alignment feature.

FIG. 15 provide an alternative variation of post 32. In FIG. 15, post 32 comprises lock element 260 having lock alignment feature 262, illustratively hinge 263. Hinge 263 allows lock element 260 to rotate from a position in line with post 32, as in FIG. 15A, to a position out of alignment with the post, as in FIG. 15B, thereby facilitating alignment with an anchor lock element 34. As shown, post 32 further comprises actuator attachment element 264, illustratively an eyelet, valve support structure 266 having slot 267 and a plurality of holes 268, and braid attachment element 269.

FIG. 16 illustrate an alternative variation of lock alignment feature 262 comprising spring 270. As with hinge 263, spring 270 facilitates alignment of post lock element 260 with an anchor lock element 34 by allowing the post lock element to rotate from a position in line with post 32, as in FIG. 16A, to a position out of alignment with the post, as in FIG. 16B. Spring 270 also applies a restoring force that urges post lock element 260 back into alignment with post 32. Furthermore, spring 270 may facilitate dynamic elongation of post 32 in response to axial tension. This elongation may facilitate axial lengthening of anchor 30 in response to radially inward compression applied to the anchor.

Figures 17, 18:
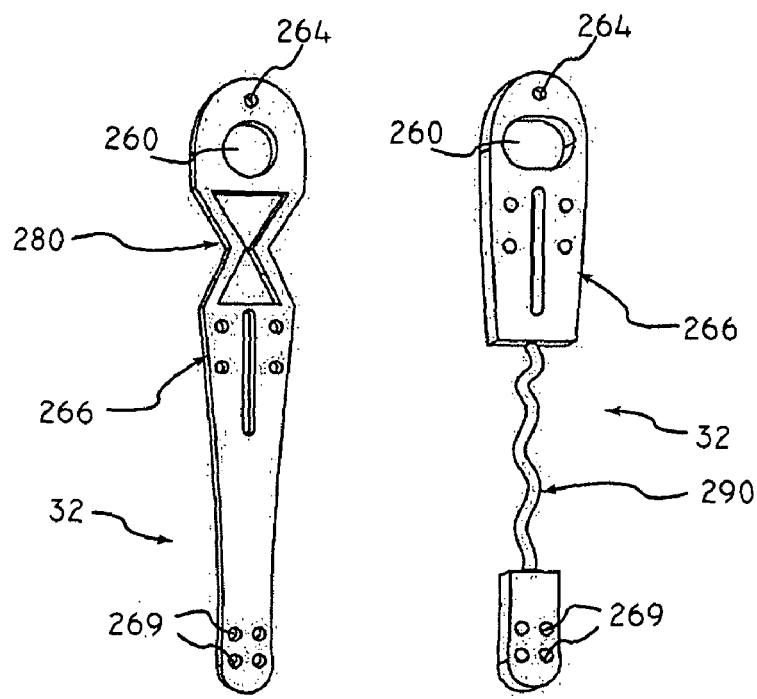
FIG. 17 shows a variation of the post having an expansile element.
FIG. 18 shows a variation of the post with an alternative expansile element.

With reference to FIG. 17, another variation of post 32 is provided comprising expansion zone 280, which may, for example, comprise a laser cut feature along post 32. Expansion zone 280 facilitates dynamic elongation of post 32 in response to axial tension applied to the post, which facilitates axial lengthening of anchor 30 in response to radially inward compression applied to the anchor. FIG. 18 illustrates an alternative expansile element 290 comprising a curved wire or rod that may be elongated and straightened through application of axial tension to facilitate axial lengthening of the anchor in response to radially inward compression applied to the anchor (and thereby axial tension applied to post 32 via interaction between post lock element 260 and an anchor lock element 34).

Element 290 additionally or alternatively may serve as a lock alignment feature. In such a configuration, element 290 optionally may not be expansile. More generally, post 32 may comprise proximal and distal ends connected by a tensile member.

Figures 19A, 19B, 19C:
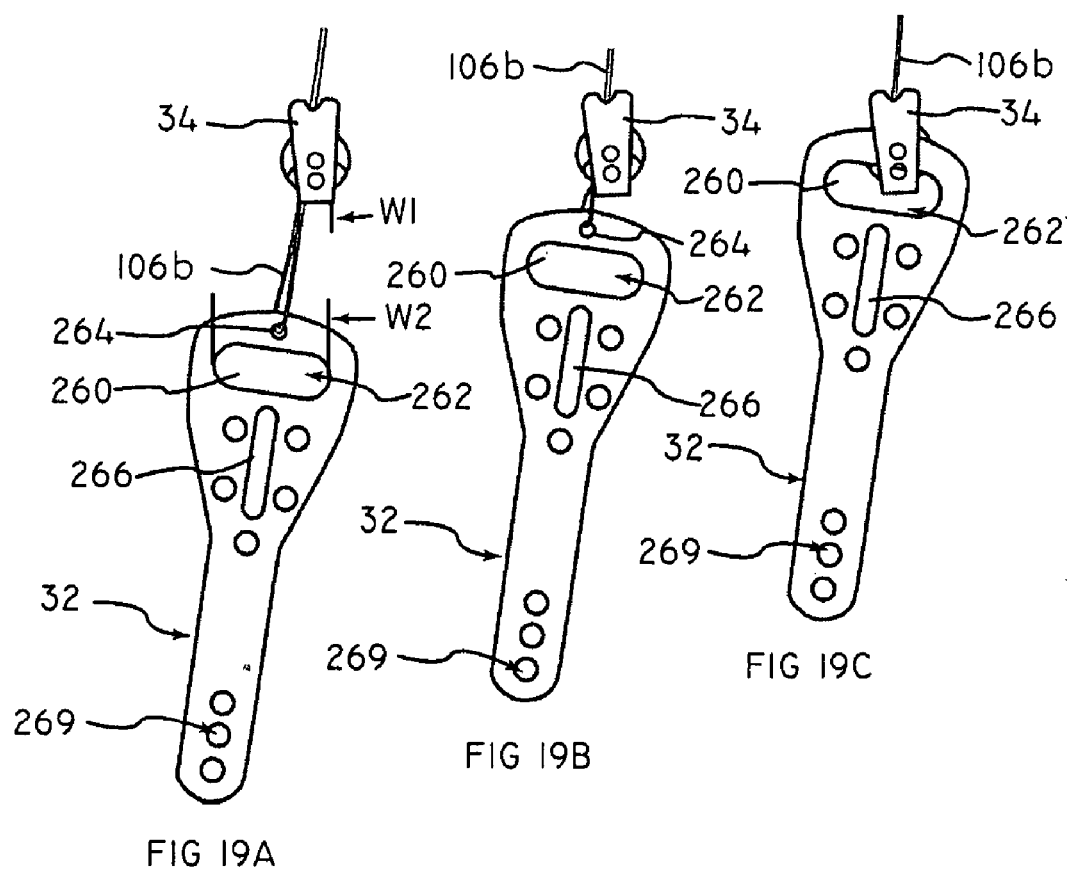
FIGS. 19A-19C show a variation of the post having an alternative lock alignment feature.

FIG. 19 illustrate another variation of post 32 having another alternative lock alignment feature 262. In FIG. 19, actuator 106b applies a proximally-directed force which brings post lock element 260 and anchor lock element 34 proximate to one another allowing the system to lock. Anchor lock element 34 defines a lock width $W_1$. In this embodiment, lock alignment feature 262 comprises post lock element lock area or width $W_2$ that is substantially wider than the lock width $W_1$, for example, at least about twice as wide. This increased width enhances the probability of interlocking the post and anchor lock elements, even at sharply misaligned angles. In FIG. 19, post 32 and anchor lock element 34 are disposed at an illustrative misalignment angle of about 10°.

Figure 20:
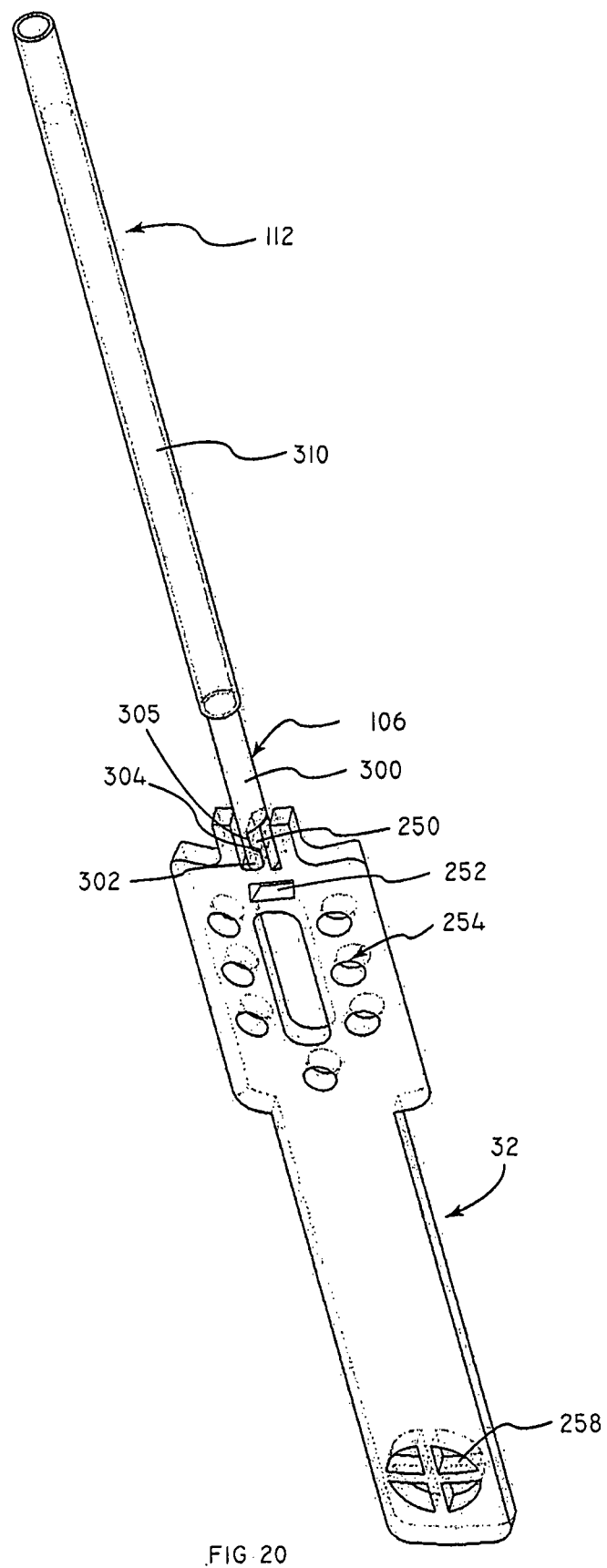
FIG. 20 shows the post variation of FIG. 14 in combination with an illustrative actuator and release actuator.

Referring now to FIG. 20, the variation of post 32 of FIG. 14 is shown in combination with an illustrative actuator 106b and release actuator 112. In FIG. 20, actuator 106b illustratively comprises rod 300 having post attachment element 302 that mates with actuator attachment element 250 of post 32. Angled camming surfaces 304 and 305 of post attachment element 302 and actuator attachment element 250, respectively, form an interface between post attachment element 302 and actuator attachment element 250. Proximal movement of actuator 106b with respect to post 32 is translated by the camming surfaces into a lateral force between the two elements that acts to separate and release post 32 from actuator 106b. Release actuator 112, illustratively tube 310, may be advanced over actuator 300 to cover the camming surface interface of the post and the actuator 106b, thereby forming a releasable attachment mechanism for securing the post to the actuator even during application of axial tension to the actuator. To separate post 32 from actuator 106b, e.g., after expansion and locking of anchor 30, release actuator 112 may be retracted relative to actuator 106b to the position shown in FIG. 20, thereby removing a constraint from camming surfaces 304 and 305 and allowing the post and actuator to be pulled apart. Release actuator 112 preferably is retracted less than about 1 inch relative to the actuator 106b in order to actuate the releasable attachment mechanism, e.g., to remove constraint from camming surfaces 304 and 305.

Referring now to FIG. 21, an alternative releasable attachment mechanism for attaching a variation of post 32 to a variation of actuator 106b is described. In FIGS. 21A and 21B, post 32 having actuator attachment element 320, illustratively an enlarged proximal opening within the post, is interference fit with post attachment element 330 of actuator 106b, illustratively an enlarged bulb, knob or other distal protrusion of the actuator. The slope of element 330 provides a camming surface that interfaces with an inside surface of opening 320. The angle of the camming interface between element 330 and opening 320 translates proximal movement of actuator 106b with respect to post 32 into a lateral movement between actuator 106b and post 32, thereby separating these elements. Release actuator 112, illustratively tube 310, covers the interference fit releasable attachment mechanism to preclude lateral movement of the post attachment element relative to the actuator attachment element, thereby releasably attaching the post to the actuator 106b. In FIG. 21C, tube 310 is retracted relative to the post and actuator, which permits lateral movement between the post and actuator attachment elements, thereby separating actuator 106b from post 32. If tube 310 has not been retracted, of course, proximal movement of actuator 106b moves post 32 and the distal portion of the anchor proximally.

Figures 22A, 22B, 22C:
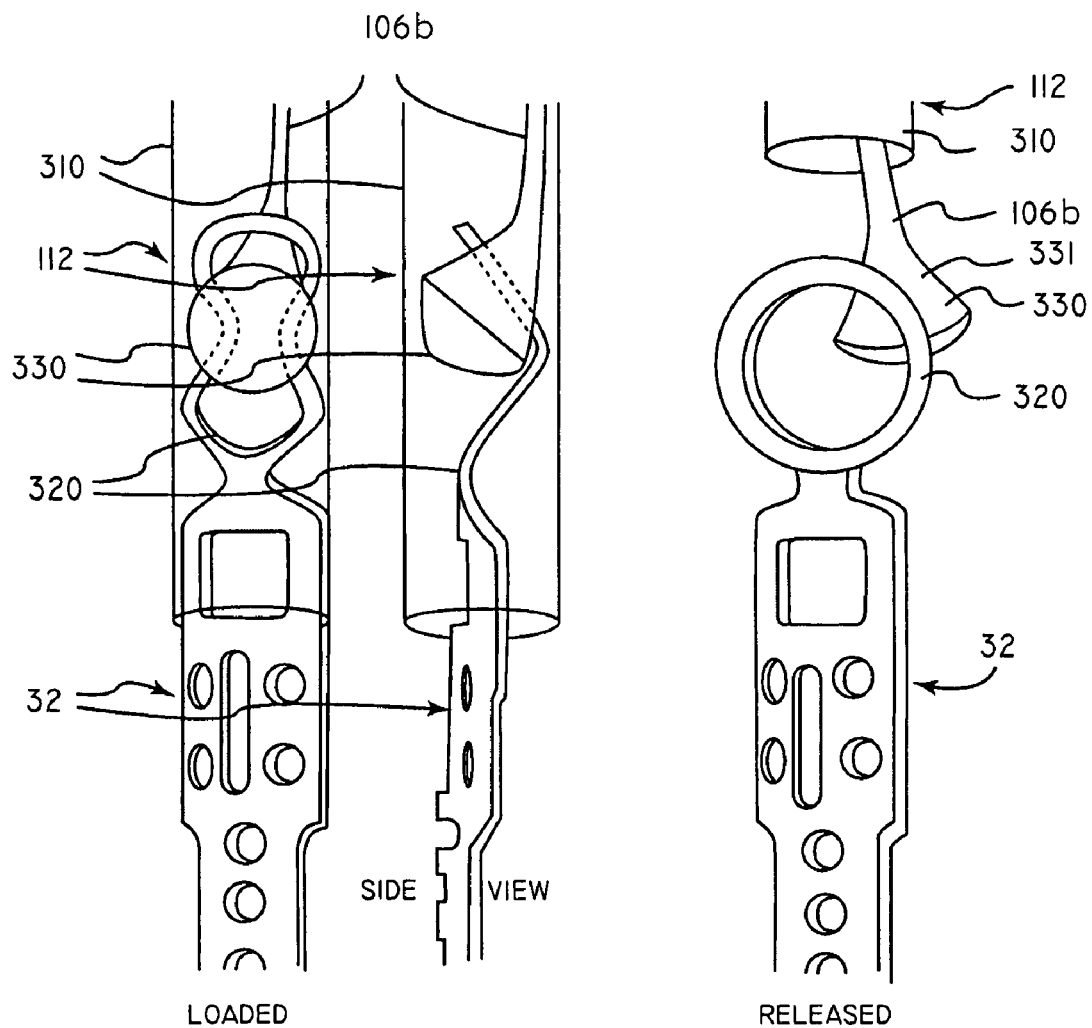
FIGS. 22A-22C show another variation of the releasable attachment mechanism.

FIG. 22 illustrate a variation of the releasable attachment mechanism of FIG. 21. In the variation of FIG. 22, actuator attachment element 320 of post 32 is deformable from a substantially round profile to an oval or "figure eight" profile by advancement of release actuator 112 over the attachment element. This forms a releasable attachment mechanism. In the deformed profile of FIGS. 22A and 22B, post attachment element 330 of actuator 106b is interference fit with the deformed actuator attachment element of post 32. In FIG. 22C, retraction of release actuator 112 relative to the post and actuator allows actuator attachment element 320 to resiliently resume its un-deformed or at-rest configuration, thereby permitting separation of post 32 from actuator 106b. Actuator attachment element 320 may, for example, be fabricated from a shape memory material, such as Nitinol. A camming surface 331 on post attachment element 330 and a corresponding surface on the inner portion of element 320 translate proximal movement of actuator 106b with respect to post 32 into lateral movement of element 330 with respect to element 320 when release actuator 112 has been retracted.

In the variation of FIG. 23, post attachment element 330 is deformable (as in FIGS. 23A and 23B), and anchor attachment element 320 may be interference fit with the post attachment element. FIG. 23C shows the post attachment element 330 in its at-rest configuration after tube 310 has been retracted, thereby releasing anchor attachment element 320. As will be apparent, for many or all of the two-part locking or attachment element elements described herein, the position of the elements may be reversed.

Figures 24A, 24B:
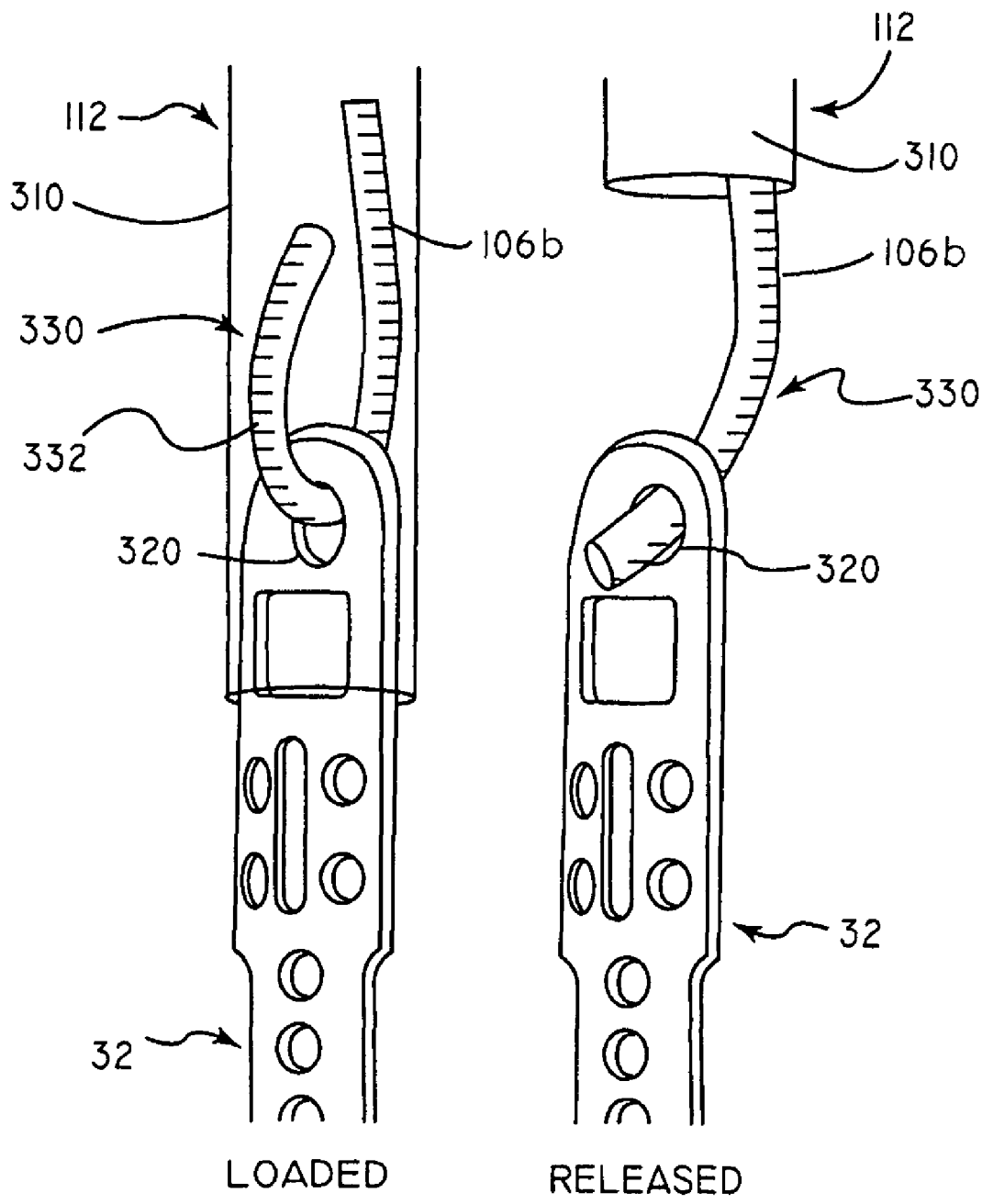
FIGS. 24A and 24B show still another variation of the releasable attachment element.

In FIG. 24, post attachment element 330 comprises wrap portion 332 that may be inserted through anchor attachment element 320, illustratively an eyelet, wrapped backwards, then covered with release actuator tube 310 to constrain the wrap portion 332 in the wrapped configuration, as in FIG. 24A. Release actuator tube 310 may be retracted relative to the wrap portion to resiliently or dynamically (e.g., by retracting actuator 106b relative to post 32) reshape the wrap portion to a substantially straight configuration for releasing the attachment between the post and the actuator, as in FIG. 24B. Wrap portion 332 preferably is fabricated from a shape memory material, such as Nitinol, or a resilient material, such as spring steel.

Figure 25:
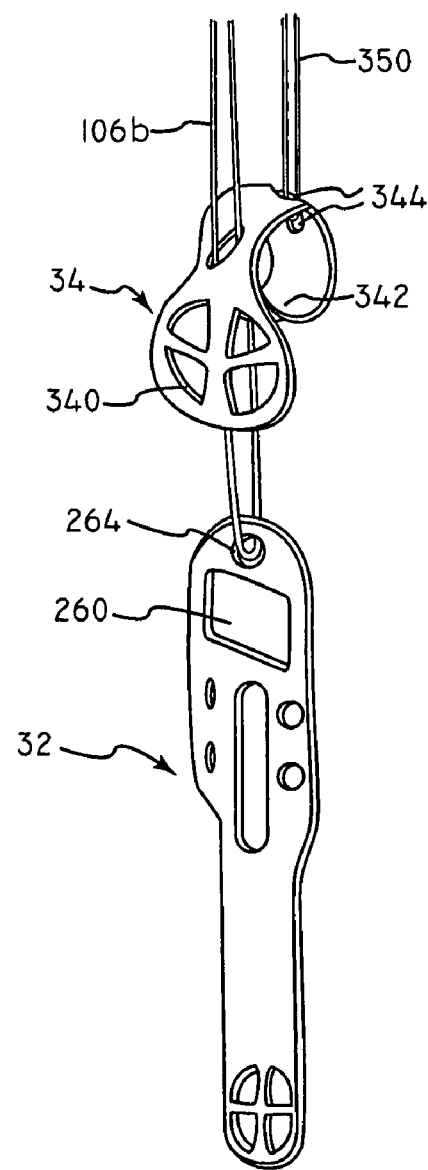
FIG. 25 shows a variation of the post, actuator and anchor lock element having a reversible lock.

FIG. 25 shows another variation of the post, actuator and anchor lock element. In FIG. 25, post 32 comprises post lock element 260 and actuator attachment element 264, illustratively an eyelet, through which actuator 106b is reversibly disposed. Anchor lock element 34 illustratively comprises a buckle, which may, for example, be formed from a cut tube or a bent resilient material. Anchor lock element 34 comprises anchor or braid attachment element 340 for attaching the buckle to anchor 30, and tab 342 for interlocking the buckle with post lock element 260, which illustratively is a slot formed through post 32. Actuator 106b therefore actuates the post (and therefore the distal end of the anchor to which the post is attached) as well as the anchor lock. Actuator 106b may be released from the post (and therefore from the anchor) by pulling one end of the control wire proximally to draw the control wire through and out of opening 264.

Anchor lock element 34 also comprises optional unlock actuator attachment 344, illustratively a pair of eyelets, through which unlock actuator 350 is releasably coupled to anchor lock element 34. Unlock actuator 350 illustratively comprises a control wire. Upon locking of tab 342 of buckle 34 within slot 260 of post 32, a proximally-directed force applied to unlock actuator 350 may remove the tab from the slot, thereby unlocking buckle 34 and post 32 and permitting the anchor to contract and elongate. Unlocking may be utilized, for example, to reposition or retrieve the anchor and valve apparatus even after the apparatus has been locked in the fully deployed configuration, as described previously with respect to FIG. 3.

FIG. 26 show another variation of the actuator, the lock actuator and the release actuator. As with other anchor lock elements, anchor lock element 34 in this embodiment is attached to a proximal end of the anchor, and the distal end of post 32 is attached to a distal end of the anchor. The anchor is not shown in FIG. 26 for ease of illustration. For the purposes of illustration, the unlock actuator also is not shown in FIG. 26.

As shown, actuator 106b actuates both post 32 (and therefore the distal end of the anchor to which the post is attached) and the lock formed between post lock element 260 and anchor lock element 34. In FIG. 26A, release actuator 112 passes through actuator 106b to actuate the releasable attachment mechanism between post 32 and actuator 106b. FIG. 26B provides a detail view of the releasable attachment mechanism. Actuator 106b comprises wrap portion 360 that passes through actuator attachment element 264 and wraps around the end of post 32. Wrap portion 360 may comprise a shape memory material, such as Nitinol, or a deformable material, e.g., a resiliently deformable material.

Wrap portion 360 further comprises first opening 362 for engaging release actuator 112, illustratively a wire or rod that passes through lumen Lu of actuator 106b. The walls of the lumen act a linear bearing and/or motion guide during advancement and retraction of the release actuator relative to the actuator. Actuator 106b also comprises second opening 364, which may be aligned with first opening 362 to engage release actuator 112, as shown. As seen in the cross-sectional view of FIG. 26C, wrap portion 360, and especially the curved portion 361 of the wrap portion, acts as a spring element that urges the first opening out of alignment with the second opening. In this manner, release actuator 112 may be interference or friction fit through first opening 362 and second opening 364. Retraction of the release actuator proximal of the first and second openings may actuate the releasable attachment mechanism to resiliently or dynamically unwrap portion 360 and release actuator 106b from post 32. Wrap and/or curved portion 360/361 of actuator 106b illustratively is disposed at a distal end of the actuator.

As will be apparent to those of skill in the art, the releasable attachment mechanism of FIG. 26 may also be utilized to attach a actuator 106a to a braided anchor 30. More generally, wrap portion 360 provides an illustrative first shape on an anchor actuation element 106 that is adapted to mate with a second shape on a post or anchor actuator attachment element (such as element 264 in FIG. 26, or a wire of the braid of anchor 30) to substantially prevent relative distal or proximal movement between the anchor actuation element and the anchor. The apparatus further comprises a release actuator adapted to actuate the releasable attachment mechanism. The release actuator is adapted to be moved to permit relative movement between the first shape and the second shape. This relative movement may change the first shape and/or the second shape to a third shape that permits relative distal or proximal movement between the anchor actuation element and the anchor or post. Furthermore, this relative movement may separate the anchor actuation element from the anchor or actuator attachment element.

Figure 27:
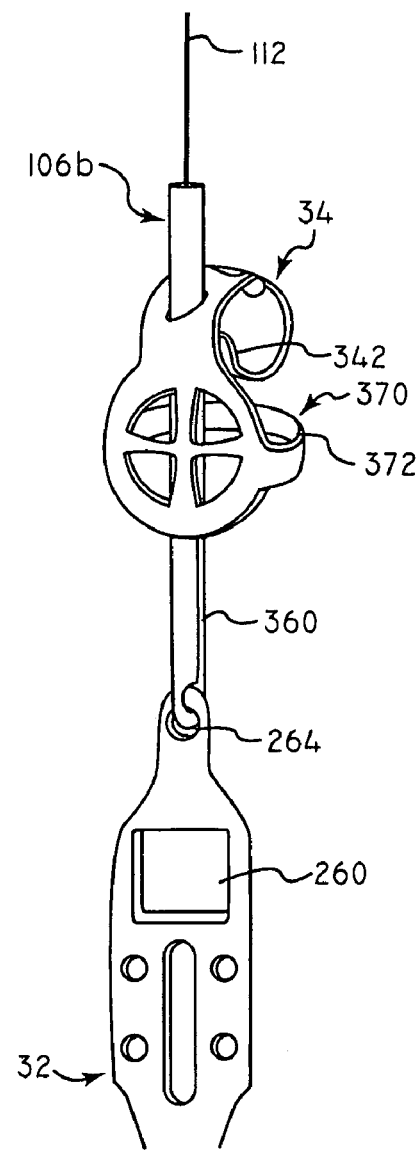
FIG. 27 shows a variation of the anchor lock element having a lock alignment feature.

FIG. 27 illustrates a variation of the anchor lock element of FIG. 26. In FIG. 27, anchor lock element 34 comprises lock alignment feature 370. Feature 370 comprises engagement portion 372, illustratively a loop, that is adapted to engage post 32 before engagement of anchor lock element 34 (i.e., before engagement of tab 342 of the anchor lock element) with post lock element 260. Feature 370 ensures alignment of the post and buckle prior to locking. Furthermore, feature 370 adds additional strength to anchor lock element 34 and opposes inwardly-directed forces applied to element 34 when valve 20 of apparatus 10 closes during diastole.

Figures 28A, 28B, 29:
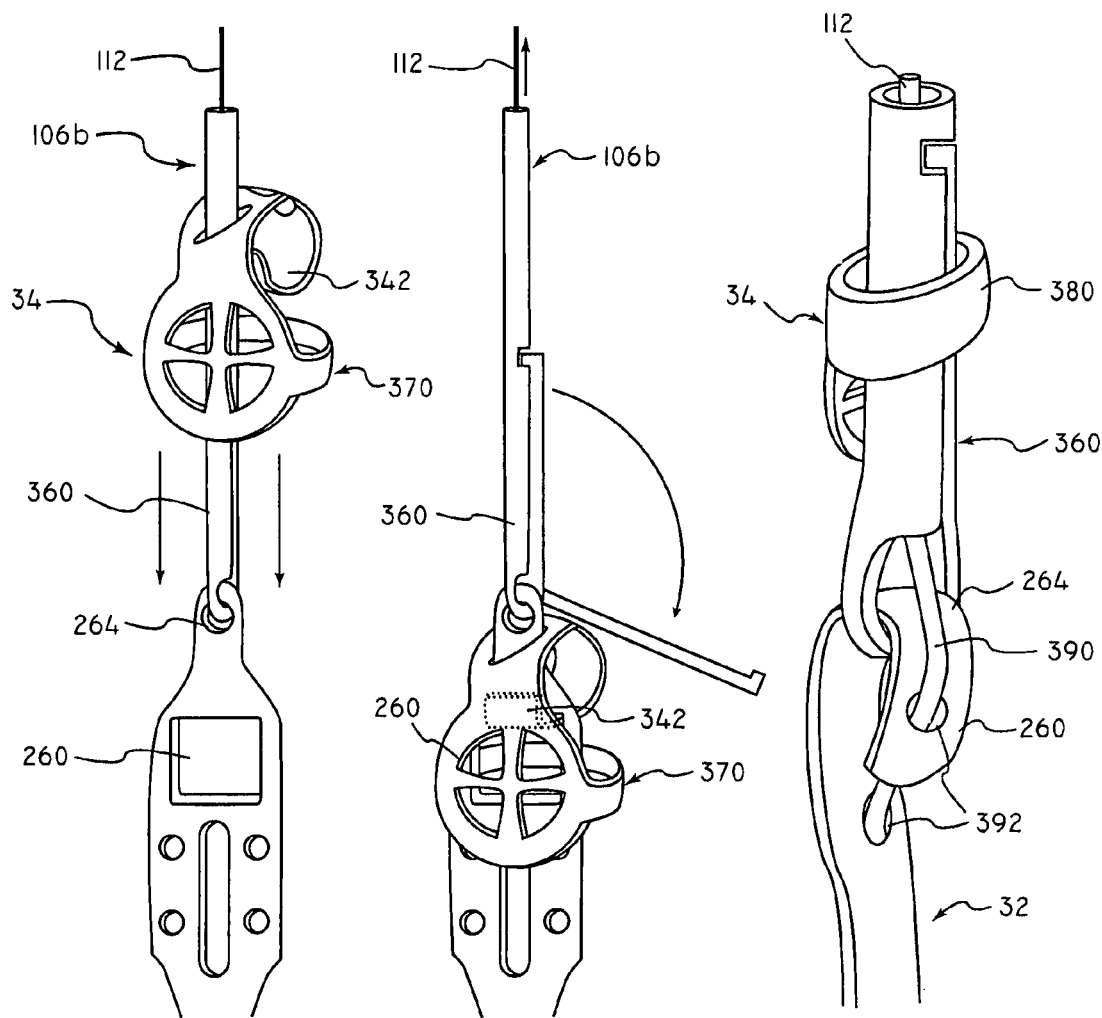
FIGS. 28A and 28B show expansion, locking and actuation of the releasable attachment mechanism of the apparatus of FIG. 27.
FIG. 29 shows another variation of the apparatus having an actuable lock prevention mechanism.

Referring now to FIG. 28, actuation of the apparatus of FIG. 27 is described. As seen in FIG. 28A, anchor lock element 34 is advanced distally relative to post 32, for example, by applying a distally-directed force to the anchor via anchor actuator 106a to move the proximal portion of the anchor distally while maintaining the position of post 32 via actuator 106b. Alternatively or additionally, a proximally-directed force may be applied to post 32 via actuator 106b while maintaining the position of the proximal end of the anchor to move the distal portion of the anchor proximally. Lock alignment feature 370 engages the proximal end of the post prior to interlocking of tab 342 of anchor lock element 34 with post lock element 260, thereby ensuring proper alignment. Continued retraction of post 32 relative to buckle 34 locks the post into the buckle, as shown in FIG. 28B. This also expands apparatus 10 to the fully deployed configuration of, e.g., FIGS. 1B and 2C. Next, release actuator 112 is retracted proximally relative to actuator 106b, which causes wrap portion 360 of the actuator to resiliently or dynamically swing outwards, thereby bringing first opening 362 and second opening 364 out of alignment. Proximal retraction of actuator 106b relative to post 32 removes wrap portion 360 from actuator attachment element 264 of post 32.

FIG. 29 shows a variation of the apparatus of FIGS. 27 and 28. In FIG. 29, anchor lock element 34 comprises locking hoop 380, while post lock element 260 comprises a wrapped or curved proximal end of post 32. The curved proximal end also forms actuator attachment element 264. Wrap portion 360 of actuator 106b is wrapped about the curved end of post 32. Release actuator 112, passing through first opening 362 and second opening 364 of actuator 106b, releasably secures this attachment. The release actuator further comprises kink 390 that facilitates passage of the actuator through release actuator attachment elements 392 of post 32, illustratively eyelets. When disposed through elements 392, release actuator 112 further acts as a lock prevention mechanism that precludes locking of the curved proximal end of post 32 with hoop 380 of anchor lock element 34.

In use, the proximal end of post 32 may be retracted through hoop 380 of anchor lock element 34. Release actuator 112 then may be retracted relative to anchor actuator 106b and post 32, such that the release actuator is disposed proximal of attachment elements 392 of the post. Next, post 32 may be allowed to distally advance until its curved proximal end catches and locks against hoop 380 of element 34. Continued retraction of release actuator 112 relative to actuator 106b facilitates separation of the actuator from the post, as described previously.

Referring now to FIG. 30, an embodiment of post 32 is described that is configured to lock against the braid of anchor 30, as opposed to a separate anchor lock element 34. Post lock element 260 illustratively comprises bent tab 400 that catches against the anchor braid to lock the anchor in a deployed configuration.

Figures 31A, 31B, 31C:
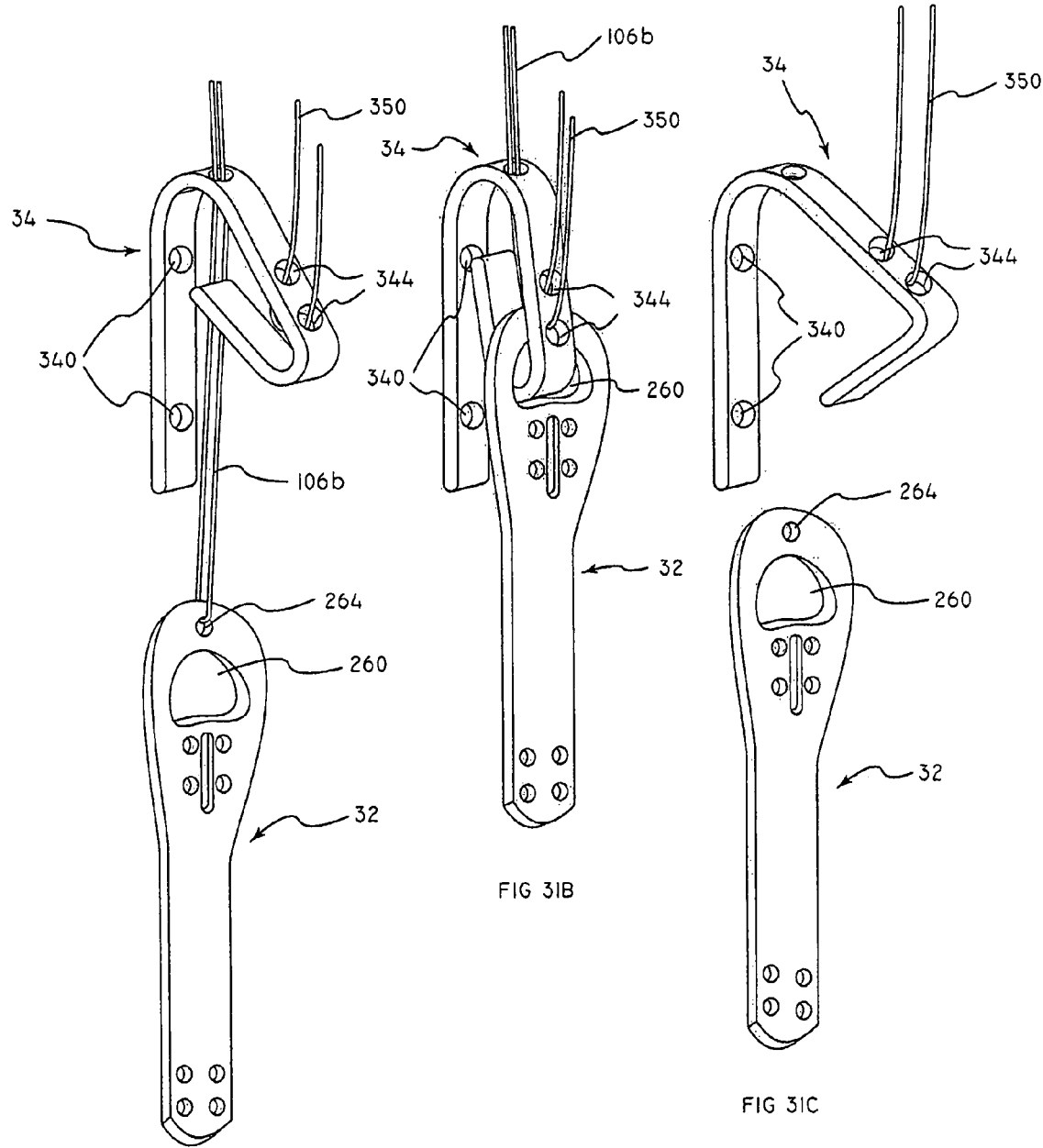
FIGS. 31A-31C show actuation and release of a variation of the anchor lock element.

FIG. 31 illustrate locking and unlocking of a variation of anchor lock element 34. Anchor lock element 34 of FIG. 31 is similar to the buckle variation of element 34 described previously with respect to FIGS. 25 and 26. However, the variation of FIG. 31 is fabricated from a strip of material that is bent to form a wrapped or curved portion. FIG. 31A illustrates the apparatus prior to locking, FIG. 31B illustrates the locked configuration, and FIG. 31C illustrates unlocking through application of a proximally-directed unlocking force to unlock actuator 350.

Figures 32A, 32B:
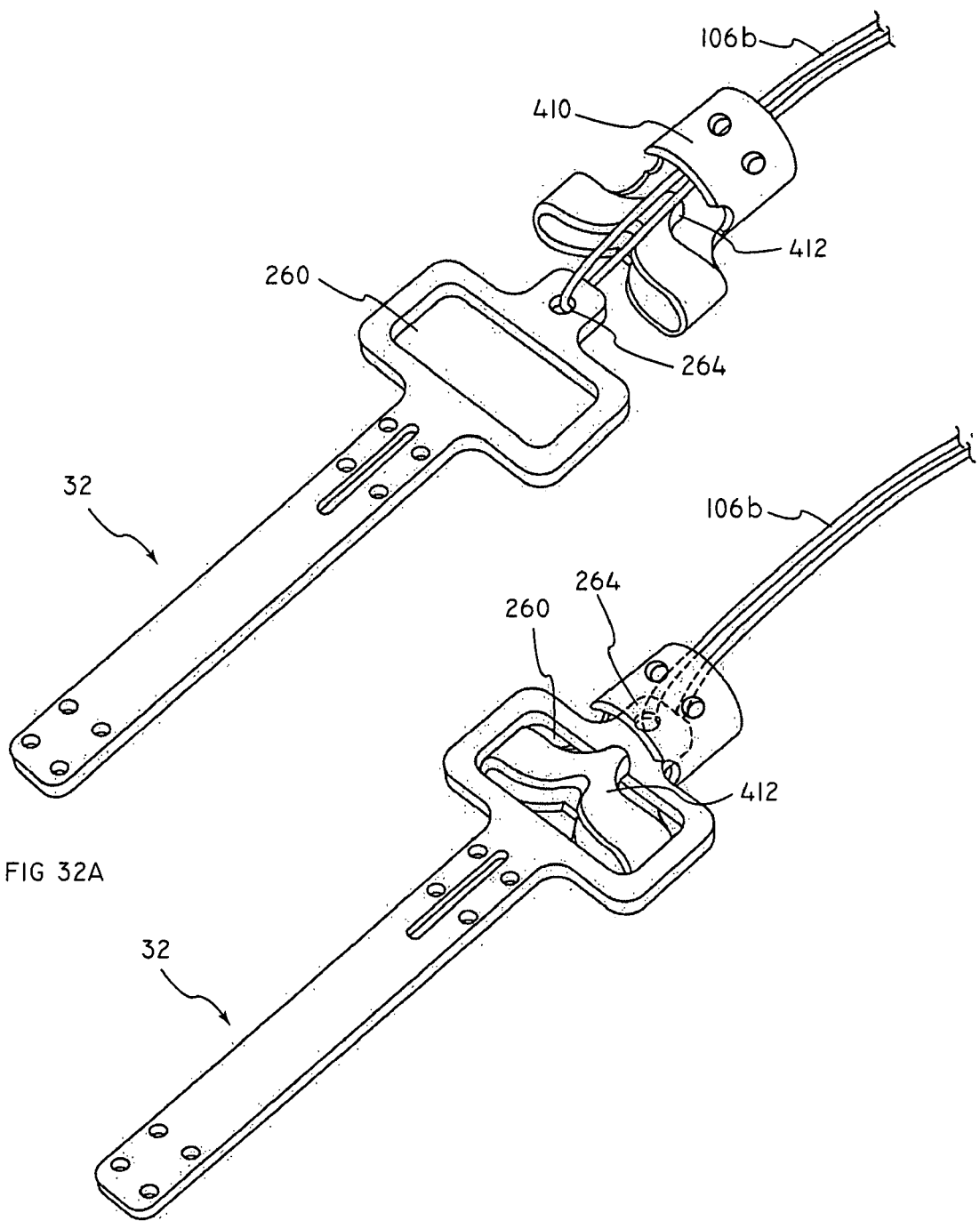
FIGS. 32A and 32B show another variation of a releasable actuation mechanism having a lock alignment mechanism which can be cut from a tube.

FIG. 32 show yet another embodiment of a releasable actuation mechanism. Anchor lock element 34 comprises lock alignment mechanism 410 disposed proximal of locking tab 412. As shown, lock alignment mechanism 410 engages the distal end of post 32 to align the post and the anchor lock element prior to locking of post lock element 260 with tab 412 of anchor lock element 34. Lock alignment mechanism 410 adds additional strength to anchor lock element 34 and opposes inwardly-directed forces applied to element 34 when valve 20 of apparatus 10 closes during diastole. Advantageously, the inwardly-directed forces act to maintain apparatus 10 in the locked configuration. Mechanism 410 optionally may be formed from a cut tube.

FIG. 33 illustrate a variation of anchor lock element 34 that may be formed from a cut tube. As seen in FIGS. 33A and 33B, element 34 comprises tabs 420 for engaging the curved proximal end of post 32 that forms post locking element 260. In order to lock the post to element 34, the curved distal end of the post is retracted proximally of tabs 420 by the action of proximal tension on post 32 by actuator 106b while element 34 is held stationary, as described above. As it enters anchor lock element 34, the curved end of the post is cammed inward by the engagement of the distal edge of element 34 with the outer surface of the curved end. Once proximal of tabs 420, the curved end of the post moves outward, thereby locking the apparatus and preventing subsequent distal movement of post 32 with respect to element 34. To unlock the apparatus, the curved portion of the post is drawn further proximally by actuator 106b until the tip of the curved portion moves into an opening 422 formed in element 34. As seen in FIGS. 33C and 33D, resilient distal advancement of the post relative to element 34, e.g., via resilient expansion of the braid of anchor 30, deforms and straightens the curved proximal end of post 32 through a camming engagement of the underside of the curved portion of the post with the inner surface of opening 422, thereby allowing actuator 106b to slide off of post 32, unlocking apparatus 10. The curved portion of post 32 optionally may be formed from a shape memory material, such that the post resumes its curved profile for subsequent relocking after unlocking.

Figures 34A, 34B, 34C, 34D, 34E, 34F:
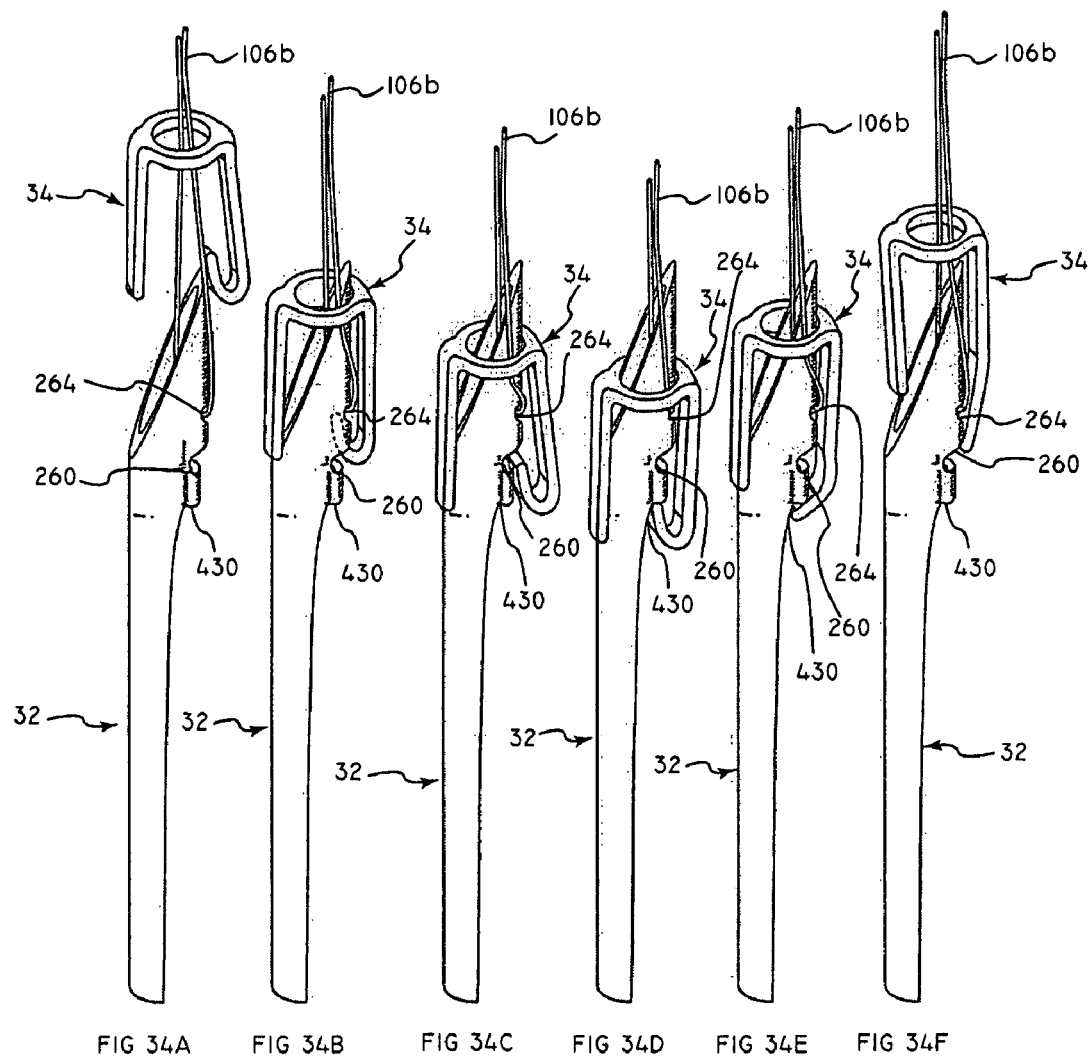
FIGS. 34A-34F show a variation of the post having an unlock actuator.

FIG. 34 illustrate a variation of post 32 and anchor lock element 32. Anchor lock element 34 illustratively comprises a curved portion 35 that engages and enters the slot of post lock element 260 to lock the anchor as post 32 is drawn proximally into element 34 by actuator 106*b*. After locking, continued proximal retraction of post 32 by actuator 106*b* engages the distal end of the curved portion of element 34 with a camming surface 430 of post 32. Resilient distal advancement of post 32 (such as by the resilient contraction and elongation of the anchor to its at-rest configuration) then deforms and straightens the wrapped end of element 34, thereby permitting anchor lock element 34 to separate from post 32, unlocking the apparatus.

Figures 35A, 35B:
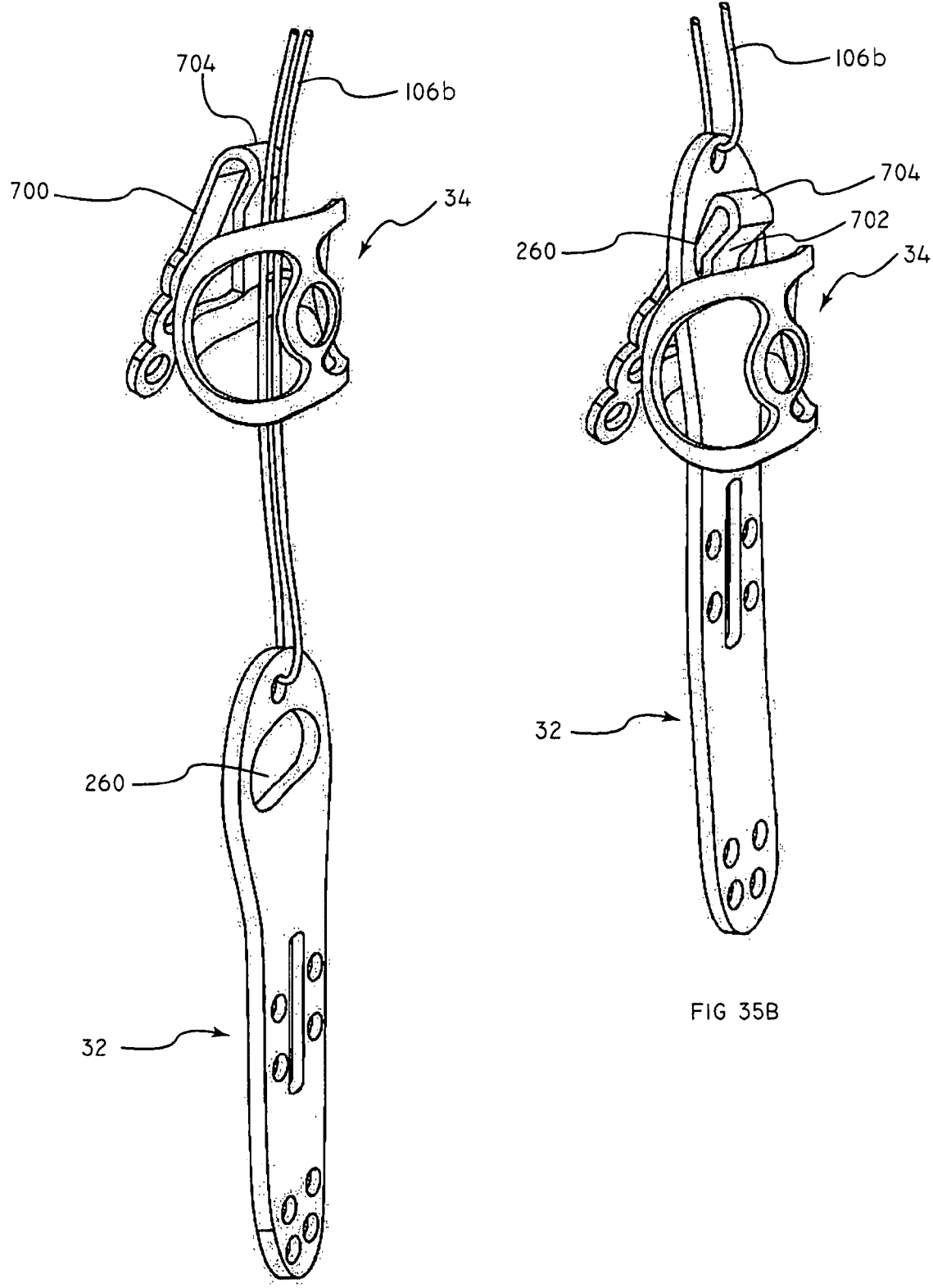
FIGS. 35A and 35B show another buckle variation of the anchor lock element.
Figure 36:
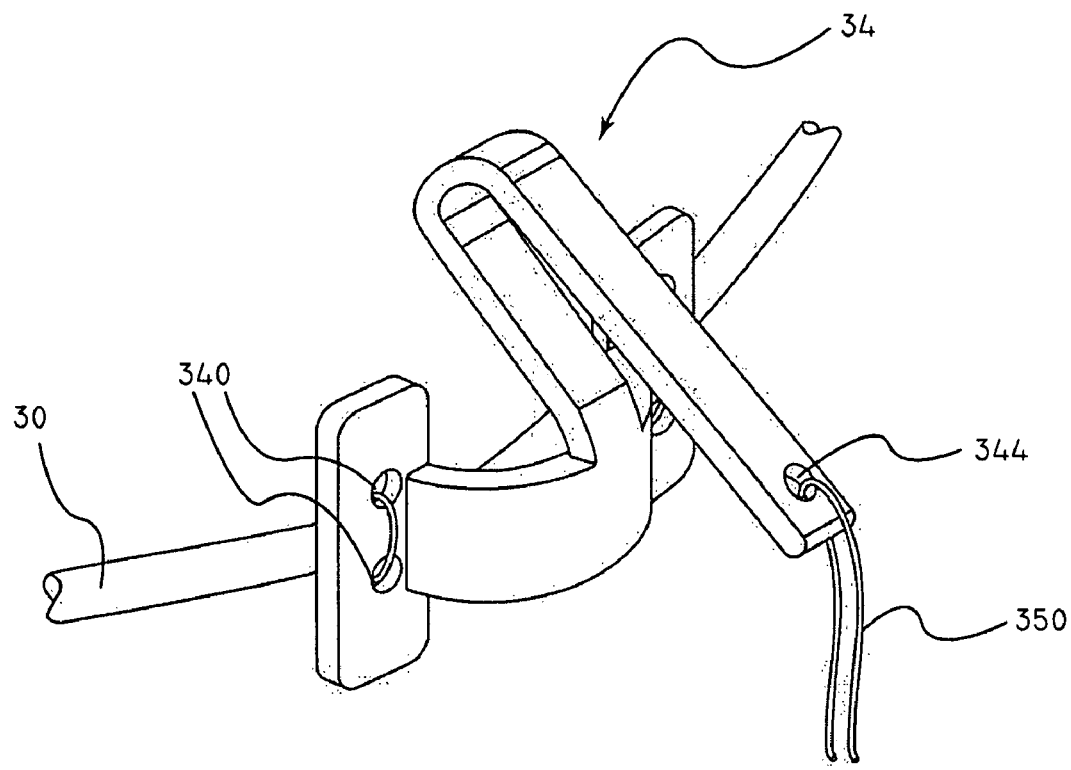
FIG. 36 shows attachment of a variation of the anchor lock element to the anchor.

FIGS. 35 and 36 illustrate additional buckle variations of anchor lock element 34. Proximal movement of post 32 into anchor lock element 34 (by, e.g., actuator 106*b*) engages a bottom surface 702 of a curved portion 700 of element 34 with the proximal end of post 32. Further proximal movement of post 32 with respect to element 34 cams curved portion 700 forward until the curved end 704 of curved portion 700 meets and resiliently moves into opening 260 in post 32, locking the apparatus. The variation of FIG. 36 illustrates attachment to the braid of anchor 30 via sutures or the like passed through openings 340 in element 34. The lock is unlockable via unlock actuator 350.

Figures 37, 38A, 38B:
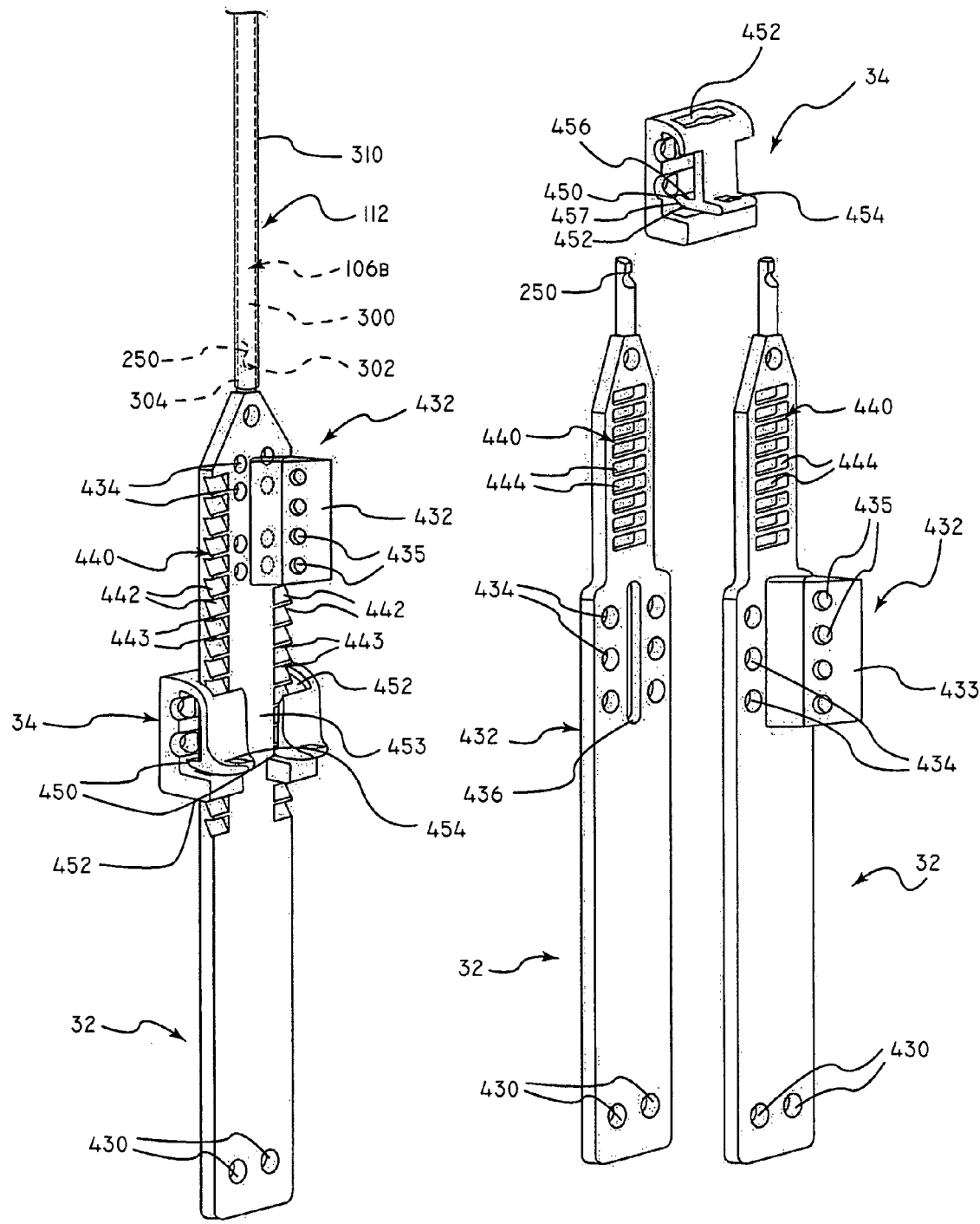
FIG. 37 shows a variation of the post and anchor lock element having a ratcheting lock.
FIGS. 38A and 38B show variations of the ratcheting lock.

Referring now to FIG. 37, an embodiment of a post 32 and anchor lock element 34 with a ratcheting lock is described. Post 32 comprises previously described actuator attachment element 250 that is releasably secured to post attachment element 302 of actuator 106*b*. (Other releasable attachment mechanisms may alternatively be used.) Post 32 also comprises braid attachment element 430 and valve attachment structure 432. In the variation of FIG. 37, valve attachment structure 432 comprises tab 433 that extends from post 32, as well as a plurality of holes 434 through post 32 and a plurality of holes 435 through tab 433. Replacement valve 20 may be attached to post 32 by sewing the valve to the valve attachment structure through holes 434 and/or 435.

Post 32 further comprises ratcheting locking element 440 having a plurality of inclined planes with camming surfaces 442 and friction surfaces 443. The inclined planes are disposed along either side of tab 433 for ratcheting and locking against ratcheting anchor lock element 34. Anchor lock element 34 comprises ratchet teeth 450 on either side of the valve attachment elements that cam against surface 442 and lock against friction surfaces 443 of element 440 of post 32, as post 32 is proximally retracted through element 34. Advantageously, providing multiple rows of inclined plane ratchets along post 32 facilitates interlocking of the post and the element at multiple discrete locations.

Element 34 comprises proximal and distal slots 452 that receive post 32, as well as central longitudinal slot 453 that facilitate passage of tab 433 (and thereby valve 20) therethrough. Actuator 106*b* may be disposed through slots 452 prior to approximation and locking of the post to anchor lock element 34 in order to facilitate alignment of the post and the anchor lock element. Element 34 may be ratcheted to any position along ratchet lock element 440 to achieve any desired locking configuration and degree of expansion of apparatus 10. Valve attachment structure 432, and thereby replacement valve 20, may be positioned proximal of the ratchet lock post-deployment or in line with the ratchet lock (i.e., neither proximal nor distal to the ratchet lock). Element 34 further comprises unlock actuator attachment(s) 454 for coupling the element to an unlock actuator, e.g., previously described unlock actuator 350, to unlock element 34 by applying a proximally-directed unlocking force that displaces ratchet teeth 450 from friction surfaces 443.

FIG. 38 illustrate variations of the apparatus of FIG. 37. Ratchet lock elements 440 of posts 32 in FIG. 38 comprise a plurality of ratchet slots 444 in which ratchet tooth 450 of anchor lock element 34 may be locked. Ratchet tooth 450 comprises proximal friction surface 456 and distal camming surface 457 to facilitate proximal retraction of a post 32 through slot 452 for ratcheting of camming surface 457 through ratchet slots 444, but to preclude distal advancement of the post once ratchet tooth 450 is engaged within ratchet slots 444 by locking a ratchet slot against friction surface 456. As with the variation of FIG. 37, anchor lock element 34 is unlockable and comprises unlock actuator attachment 454. In contrast to the variation of FIG. 37, the ratchet lock is disposed proximally of valve attachment structure 432, and thereby proximally of replacement valve 20. In FIG. 38A, valve attachment structure 432 comprises slot 436 instead of tab 433.

FIG. 39 illustrate another variation of the ratchet lock of FIG. 37. In FIG. 39, ratchet lock elements 440 of post 32 extend along only one edge of the post. Thus, anchor lock element 34 comprises unitary ratchet tooth 450 for camming against surfaces 442 and locking against friction surfaces 443 of elements 440 of post 32, as post 32 is proximally retracted through element 34.

The apparatus of FIG. 39 also comprises unlock or adjustment actuator 500 that is releasably attached to anchor lock element 34 along unlock actuator attachment 454. Actuator 500 comprises two independently or concurrently actuable elements: adjustment element 510 and release element 520. Adjustment element 510 comprises elongated member 512 having protrusion 514 with lumen 515, as well as distal extension 516 with notch 518 having optional camming surface 519. Release element 520 comprises elongated member 521, which may, for example, comprise a mandrel, that is configured for passage through lumen 515 of protrusion 514 of adjustment element 510. Elongated members 512 and 521 of actuator 500 preferably extend through delivery system 100 to the exterior of the patient for independent or concurrent advancement and/or retraction by a medical practitioner.

Figures 39A, 39B, 39C:
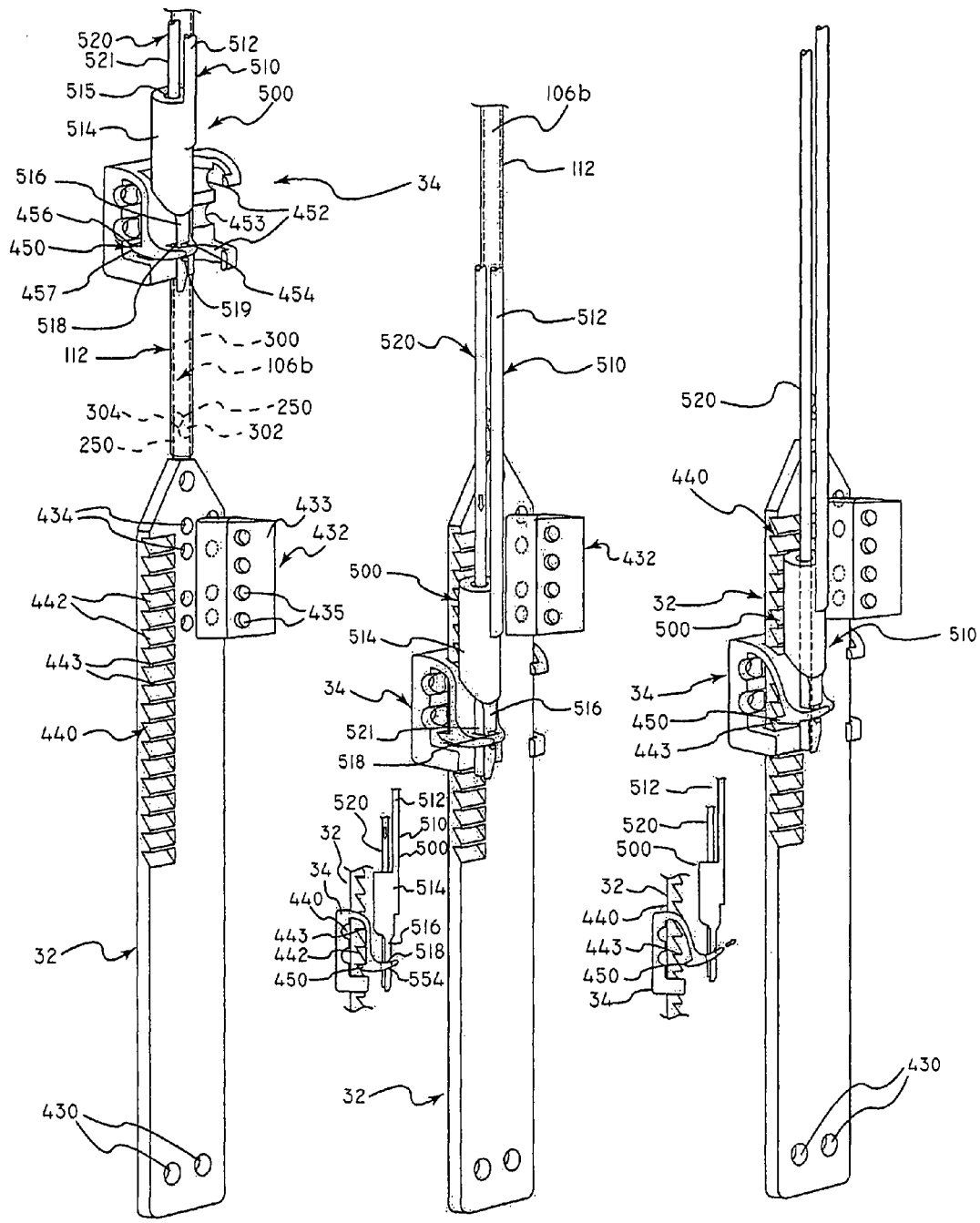
FIGS. 39A-39H show actuation of another variation of the ratcheting lock.

As seen in FIG. 39A, notch 518 of adjustment element 510 of actuator 500 may be positioned within unlock actuator attachment 454 of anchor lock element 34 during deployment of apparatus 10. As seen in FIG. 39B, anchor lock element 34 is locked within ratcheting lock elements 440 of post 32 by proximally retracting actuator 106*b* relative to anchor lock element 34. Release element 520 then may be advanced relative to adjustment element 510 to position elongated member 521 within unlock actuator attachment 454 adjacent distal extension 516 of adjustment element 510. This serves to friction lock or interference fit actuator 500 within attachment 454 along notch 518 of adjustment element 510. Thus, concurrent advancement and/or retraction of the adjustment and release elements of actuator 500 by a medical practitioner causes anchor lock element 34 to move in unison with actuator 500. As will be apparent, actuator 500 alternatively may be friction locked with anchor lock element 34 prior to full deployment of apparatus 10. Furthermore, actuator(s) 500 may assist, or be used in place of, actuators 106*a* to deploy apparatus 10.

Figures 39D, 39E, 39F:
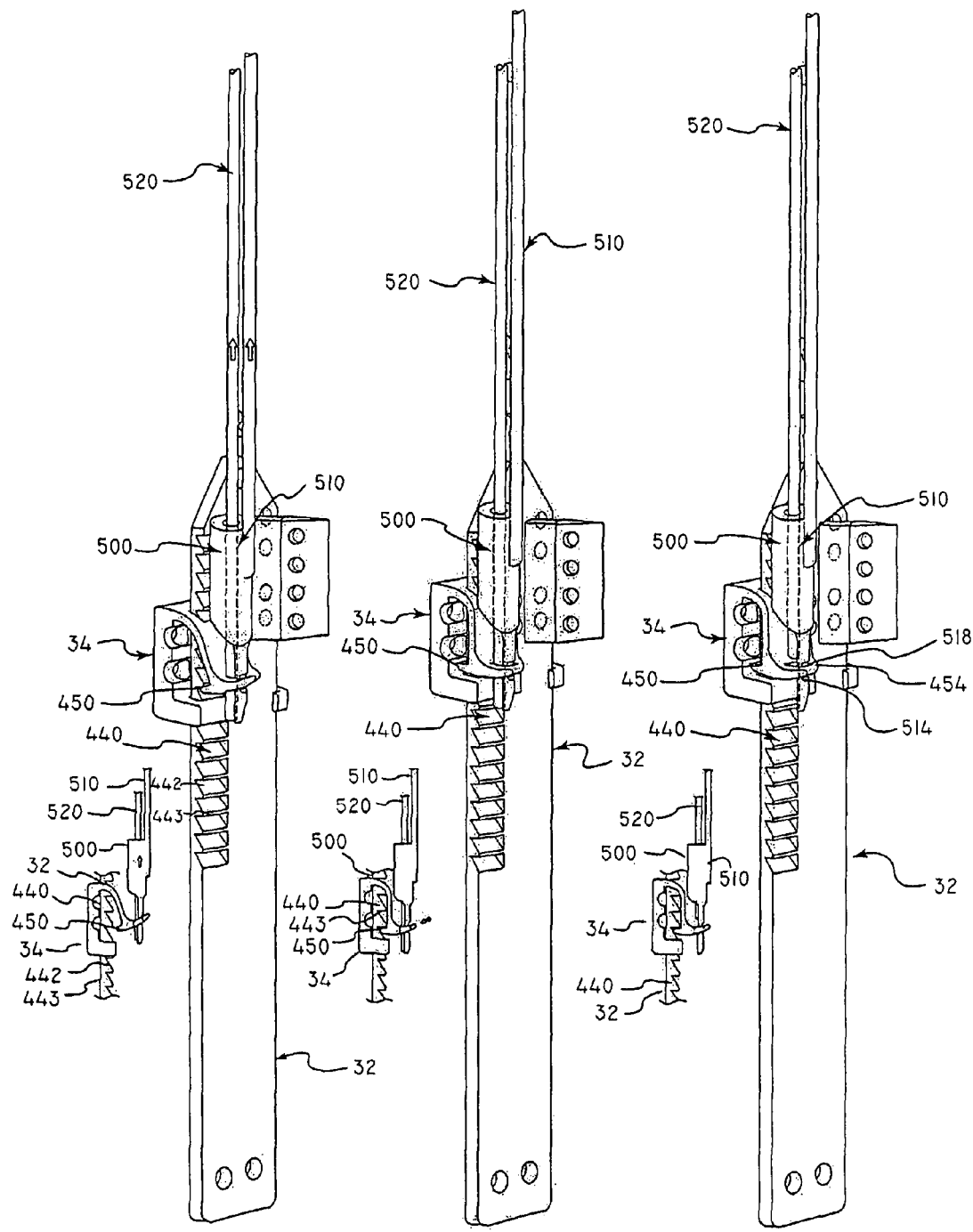

As seen in FIG. 39C, the lock formed between anchor lock element 34 and post 32 may be unlocked or adjusted, as desired, by applying a lateral unlocking force to ratchet tooth 450 via actuator 500 that pulls the ratchet tooth away from a friction surface 443 of ratcheting lock elements 440. Actuator 500 then may be distally advanced or, as seen in FIG. 39D, proximally retracted relative to ratcheting lock elements 440 and post 32 to further expand or partially collapse anchor 30, respectively (further expansion alternatively may be achieved by further ratcheting ratchet tooth 450 along camming surface 442 of ratcheting lock elements 440, e.g., by further proximally retracting actuator 106b, which is not shown in FIGS. 39C-39F for the sake of clarity). Anchor actuation elements 106 may assist such controlled expansion or collapse anchor 30.

Figures 39G, 39H:
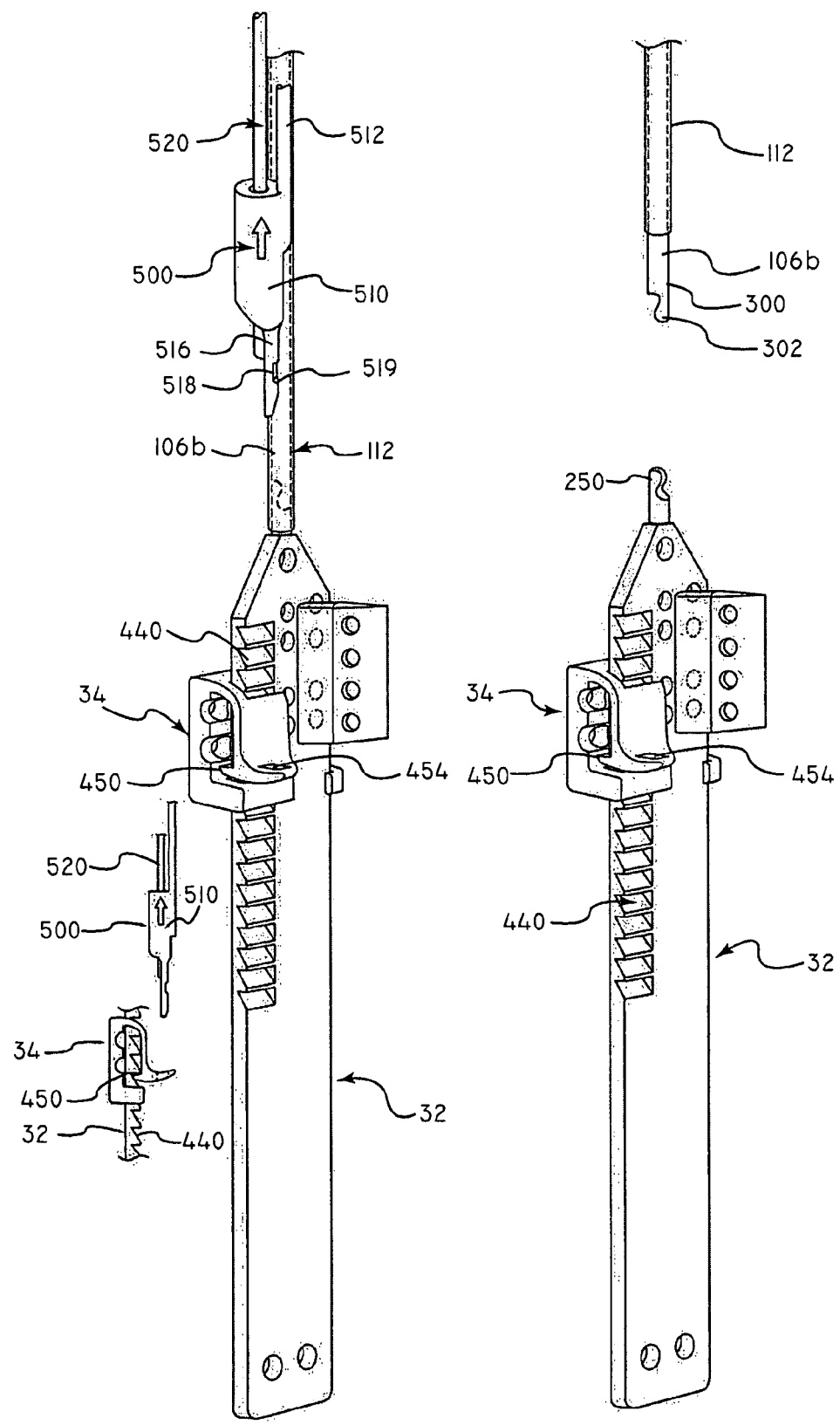

When (re-)positioned at a desired location and/or when a desired degree of locking has been achieved, the lateral unlocking force may be removed from ratchet tooth 450 to again lock anchor lock element 34 to post 32 along ratcheting lock elements 440, as in FIG. 39E. To complete deployment of apparatus 10, adjustment actuator 500 and actuator 106b, as well as actuator 106a (not shown), may be separated from the apparatus. In FIG. 39F, release element 520 of actuator 500 is proximally retracted relative to adjustment element 510, thereby removing elongated member 521 of release element 520 from unlock actuator attachment 454 of anchor lock element 34. This removes the interference fit between notch 518 and attachment 454. Proximal retraction of actuator 500 relative to anchor lock element 34 detaches adjustment element 510 of actuator 500 from attachment 454 of anchor lock element 34, as in FIG. 39G. Optional camming surface 519 along notch 518 may facilitate such detachment. In FIG. 39H, actuator 106b is detached from post 32 by retracting release actuator 112 relative to the actuator, as described previously.

Referring now to FIG. 40, another variation of an adjustable ratcheting lock element is described. As seen in FIG. 40A, post 32 comprises tube 470 having lumen 471 and ratcheting lock element 472, illustratively a plurality of slots that communicate with lumen 471. Post 32 also comprises valve support structure or attachment element 474 and braid attachment element 476.

Anchor lock element 34, which may be fabricated from a cut tube, comprises a substantially cylindrical structure having braid attachment element 480, lumen 482 and tabs 484. As seen in the top view of FIG. 40B, tabs 484 of anchor lock element 34 are configured for locking within the slots of ratcheting lock element 472 of post 32. As seen in the top view of FIG. 40C, adjustment actuator 490, illustratively mandrel M having tapered distal end 494 that acts as a camming surface, may be advanced through lumen 481 of anchor lock element 34 and lumen 471 of tube 470 of post 32, to displace tabs 484 from the locking slots of post 32, thereby unlocking the post from the anchor lock element. This facilitates, for example, readjustment of a degree of locking/expansion of apparatus 10, repositioning of apparatus 10, retrieval of apparatus 10, etc.

FIG. 41 illustrate a variation of anchor lock element 34 wherein tabs 484 are positioned along a different axis. This may provide a more secure lock between post 32 and anchor lock element 34. FIG. 42 illustrate a variation of post 32 configured for use with the variation of anchor lock element 34. In FIG. 32, post 32 comprises groove 478 that connects the slots of ratcheting lock element 472. Groove 478 does not communicate with lumen 471 of tube 470 of post 32. Rather, the groove may act as a lock alignment mechanism that guides tabs 484 of anchor lock element 34 along post 32 and ratcheting lock element 472, as seen in the top view of FIG. 42B.

Referring now to FIG. 43, a method of actuating the variation of FIG. 41 is described. As seen in FIG. 43A, adjustment actuator 490 is initially disposed through lumen 482 of anchor lock element 34 and within lumen 471 of post 32. Post 32 then may be proximally retracted relative to anchor lock element 34, e.g., via actuator 106b (not shown). In FIG. 43B, actuator 490 serves as a lock prevention mechanism that precludes locking of tabs 484 within ratcheting lock element 472. In FIG. 43C, actuator 490 is retracted relative to post 32 and anchor lock element 34, which opens up lumen 471 of tube 470 and allows tabs 484 to pass through the slots of ratcheting lock element 472, thereby locking the post to the anchor lock element. In FIG. 43D, actuator 490 is re-advanced within lumen 471, such that tapered distal end 494 of mandrel M serves as a camming surface that urges tabs 484 out of lumen 471 as the actuator is advanced. This unlocks the post from the anchor lock element to facilitate adjustment, repositioning or retrieval of apparatus 10. In FIG. 43E, a degree of locking/expansion of the apparatus is adjusted by repositioning anchor lock element 34 relative to post 32, and thereby tabs 484 relative to ratcheting lock element 472. When properly adjusted, actuator 490 may be removed from lumen 471 of tube 470 of post 32, as in FIG. 43F. Tabs 484 resiliently return to the locked configuration within the slots of ratcheting lock element 472.

Figures 44A, 44B:
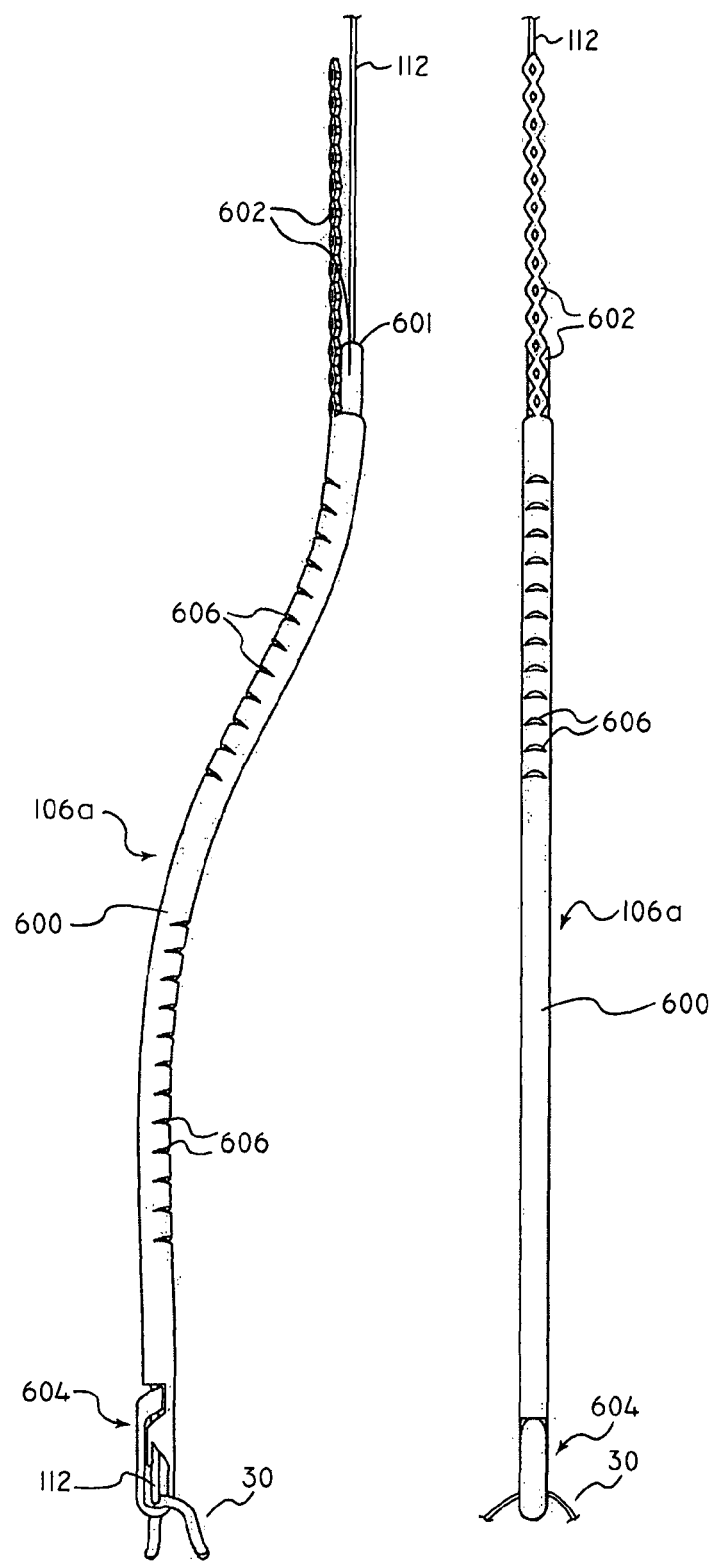
FIGS. 44A and 44B show a variation of an anchor/actuator.

Referring now to FIG. 44, an embodiment of anchor/actuator 106a is described. Actuator 106a comprises elongated member 600 having proximal extension 602 that may be attached, for example, to previously described multi-lumen shaft or catheter 108 of delivery system/deployment tool 100 (see FIG. 1), e.g., via epoxy, UV curing, etc. Lumen 601 extends through elongated member 600 from proximal extension 602 to releasable attachment mechanism 604. Releasable attachment mechanism 604 releasably attached actuator 106a to the braid of anchor 30. The mechanism comprises release actuator 112 and illustratively is similar to the previously described releasable attachment mechanism of FIGS. 26-28. Release actuator 112, illustratively a mandrel, passes through a lumen Lu of multi-lumen shaft 108 and then through lumen 601 of actuator 106a to mechanism 604.

Actuator 106a further comprises shaping features 606 that affect a shape of the anchor actuator when an anchor actuation force is applied to anchor 30. These features may comprise, for example, reduced diameter portions of the actuator, reduced wall thickness portions of the actuator and/or slits formed in the anchor actuator. Application of an anchor actuation force may, for example, provide actuator 106a with the profile seen in FIG. 44A. This profile may facilitate expansion of anchor 30/apparatus 10. As will be apparent, shaping features may be provided with any anchor actuation elements 106, including any of the previously described variations of actuators 106b.

As seen in FIG. 45, releasable attachment mechanism 604 comprises wrap portion 610 that may, for example, pass through the braid of anchor 30 and wrap around the proximal end of the anchor. Wrap portion 610 may comprise a shape memory material, such as Nitinol, or a deformable material, e.g., a resiliently deformable material. The wrap portion comprises first opening 612 for engaging release actuator 112. The walls of lumen 601 of elongated member 600 may act as a linear bearing and/or motion guide during advancement and retraction of the release actuator relative to the actuator. Actuator 106a also comprises second opening 614, which may be aligned with first opening 612 to engage release actuator 112, as shown. Wrap portion 610, and especially curved portion 611 of the wrap portion, acts as a spring element that urges the first opening out of alignment with the second opening to engage and hold release actuator 112 in place.

As seen in FIG. 45C, when the release actuator is retracted proximally relative to the actuator, wrap portion 610 resiliently or dynamically swings outwards. Thereafter, proximal retraction of anchor actuator 106a relative to anchor 30 detaches wrap portion 610, and thereby actuator 106a, from the anchor. Surface 616 of wrap portion 610 may act as a camming surface as the inner surface of wrap portion 610 slides along the anchor braid 30 to facilitate such detachment.

In this manner, release actuator 112 may be interference or friction fit through first opening 612 and second opening 614. Retraction of the release actuator proximal of the first and second openings actuates releasable attachment mechanism 604 to resiliently or dynamically unwrap portion 610 and release actuator 106a from anchor 30. Wrap portion 610 of actuator 106a illustratively is disposed at a distal end of the actuator.

Figures 46A, 46B, 46C:
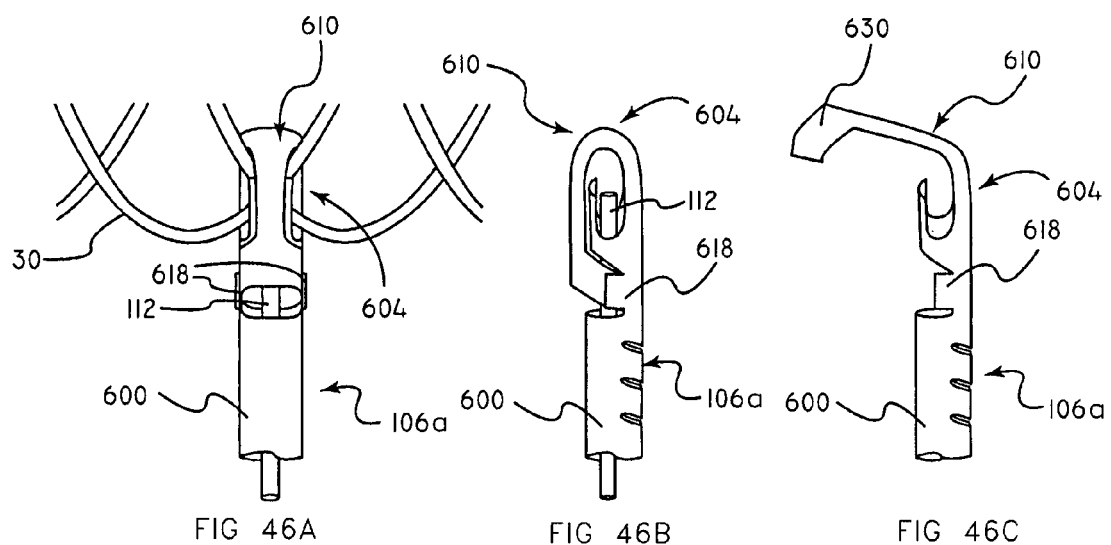
FIGS. 46A-46C show a variation of the releasable attachment mechanism of FIG. 45.

With reference to FIG. 46, a variation of releasable attachment mechanism 604 is described. In FIG. 46, wrap portion 610 illustratively comprises tabs 618 that act as an alignment mechanism for aligning the wrap portion of mechanism 604 with elongated member 600. This may facilitate advancement of release actuator 112 through mechanism 604. FIG. 47 illustrate a variation of tabs 618 wherein the tabs are rounded. This may reduce friction, provide an atraumatic surface, etc. Additional shapes for tabs 618 will be apparent. Alternatively, tabs 618 may act as spring elements which are loaded when element 630 is seated, as shown in FIG. 47B. In this configuration tabs 618 apply a force directed towards element 630 such that 630 will be ejected when element 112 is retracted. In this way tabs 618 apply a restraining force on element 112 which reduces the risk of an early release.

Figures 48A, 48B, 48C:
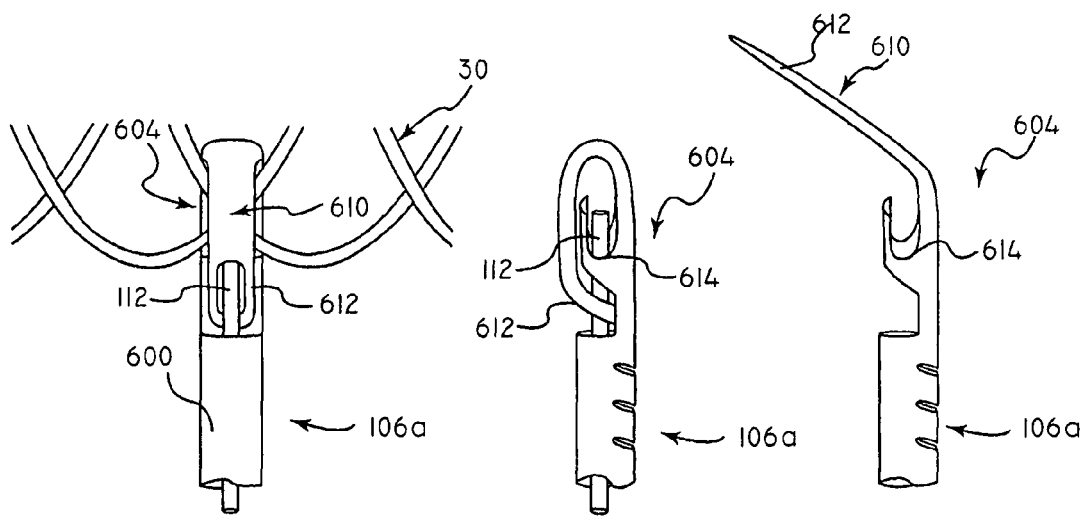
FIGS. 48A-48C show yet another variation of the releasable attachment mechanism.

FIG. 48 illustrate a variation of wrap portion 610 that comprises a substantially straight distal region in an at-rest configuration, as seen in FIG. 48C. It is expected that providing a substantially straight distal region along wrap portion 610 may facilitate detachment of actuator 106a from anchor 30, i.e., may reduce a risk of snagging the wrap portion along the braid of the anchor. The wrap portion may be resiliently deformed for passage of release actuator 112 through first opening 612, as in FIGS. 48A and 48B.

Referring now to FIG. 49, variations of release actuator 112 for use with releasable attachment mechanism 604 are described. In FIG. 49A, the release actuator comprises a simple mandrel. In FIGS. 49B and 49C, the release actuator comprises protrusion 620 having friction surface 621. In FIG. 49D, actuator 112 comprises coil 622. In FIGS. 49E-49H, the actuator comprises kink 624, which may act as a camming surface, as shown. The kink may also provide tactile feedback to a medical practitioner. In FIGS. 49I and 49J, the release actuator comprises ball or knob 626 disposed proximal of the actuator's distal end. In FIGS. 49K and 49L, ball 626 is disposed at the distal end of actuator 112. The ball may act as a camming surface. In FIG. 49M, actuator 112 comprises protrusion 628 having proximal camming surface 629. In FIG. 49N, the actuator comprises oblong protrusion 430 having friction surface 431. Additional variations of actuator 112 will be apparent.

Figures 50A, 50B:
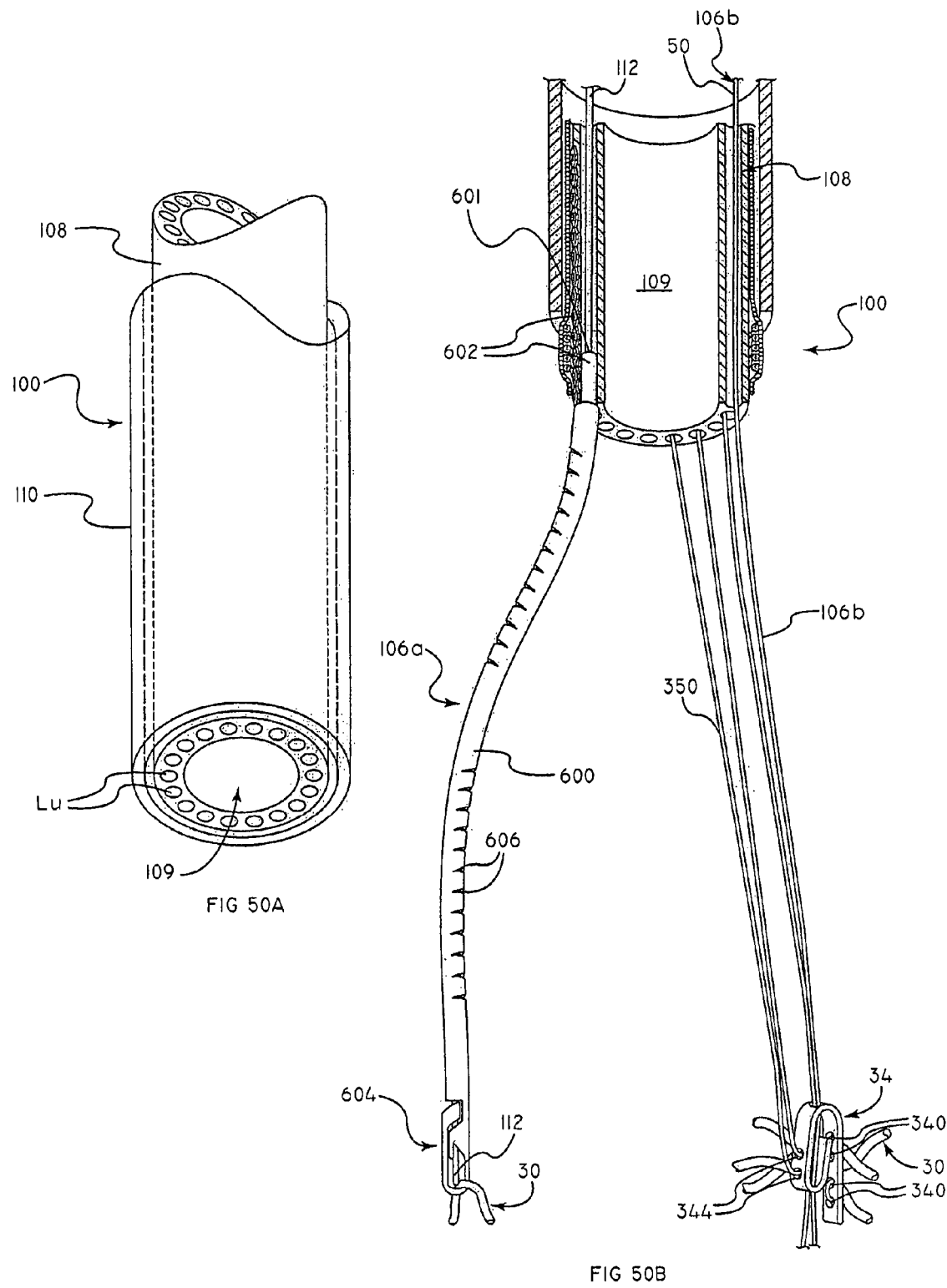
FIGS. 50A and 50B show detail views of an embodiment of the delivery system/deployment tool.

Referring now to FIG. 50, an embodiment of delivery system/deployment tool 100 is described. FIG. 50A provides a detail view of multi-lumen catheter 108 and sheath 110. As discussed previously catheter 108 comprises central lumen 109 and a plurality of circumferentially-disposed lumens Lu.

As seen in FIG. 50B, actuator 106a is coupled to catheter 108 via proximal extension 602, such that lumen 601 is coaxially disposed within a lumen Lu of the catheter. Release actuator 112 extends through lumens Lu and 601. Actuator 106a is distally attached to the braid of anchor 30 along releasable attachment mechanism 604. For the sake of clarity, a single actuator 106a is shown in FIG. 50B, but multiple such actuators preferably are provided, as in FIG. 51 described hereinafter.

FIG. 50B also illustrates actuator 106b. The actuator extends through a lumen Lu of catheter 108 and through anchor lock element 34 to post 32 (not shown). Unlock actuator 350 is also provided and extends through a lumen Lu to unlock actuator attachment 344 of anchor lock element 34. Anchor lock element 34 illustratively comprises the variation described previously with respect to FIG. 31. The element is attached to the braid of anchor 30 along anchor attachment elements 340. As with actuator 106a, a single anchor lock element 34 and actuator 106b are shown in FIG. 50B. This is only for the sake of clarity, and multiple such actuators may be provided, e.g., three actuators.

Figure 51A:
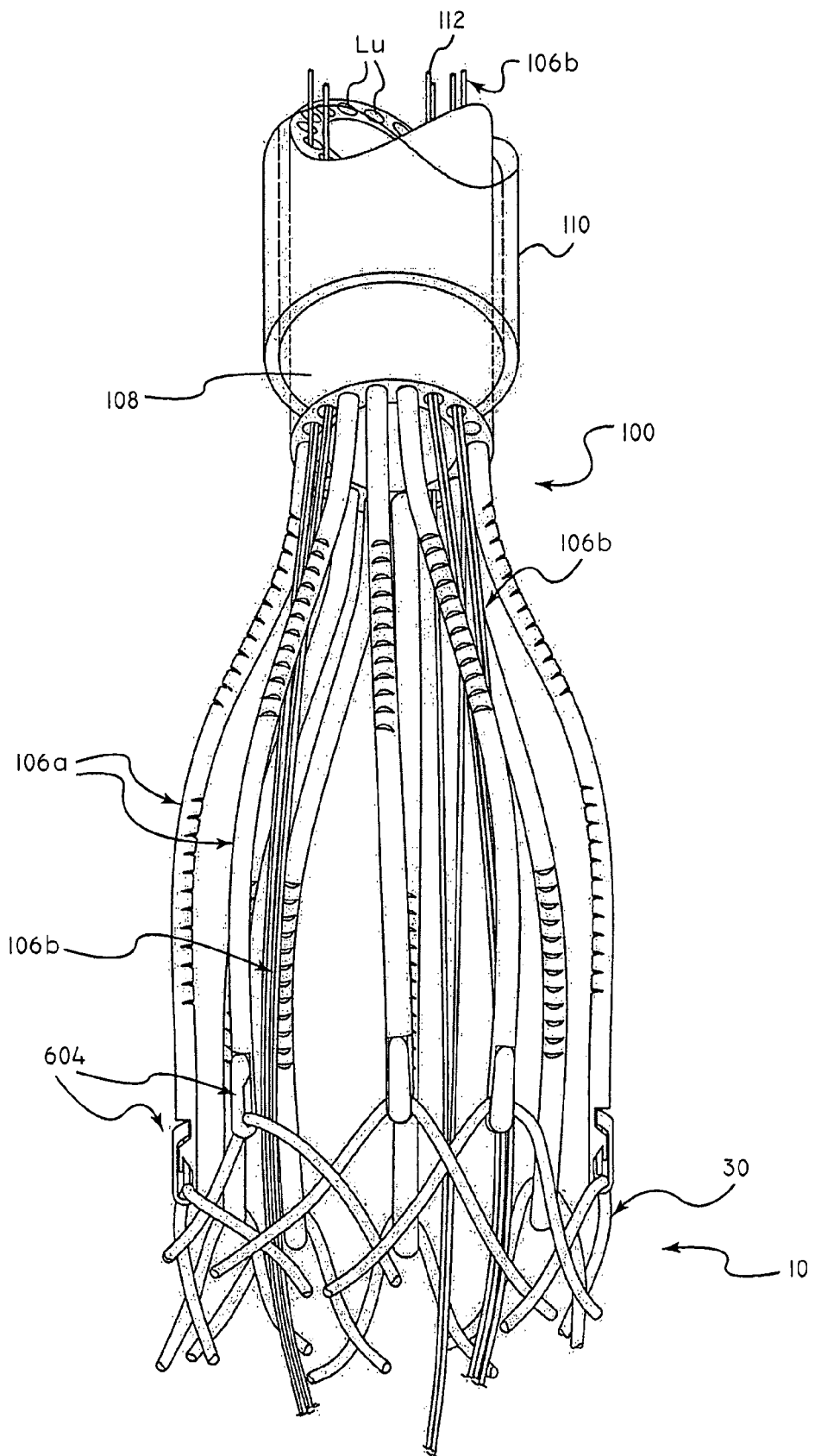
FIGS. 51A and 51B show the delivery system/deployment tool of FIG. 50 releasably attached to apparatus 10, and detached from the apparatus.
Figure 51B:
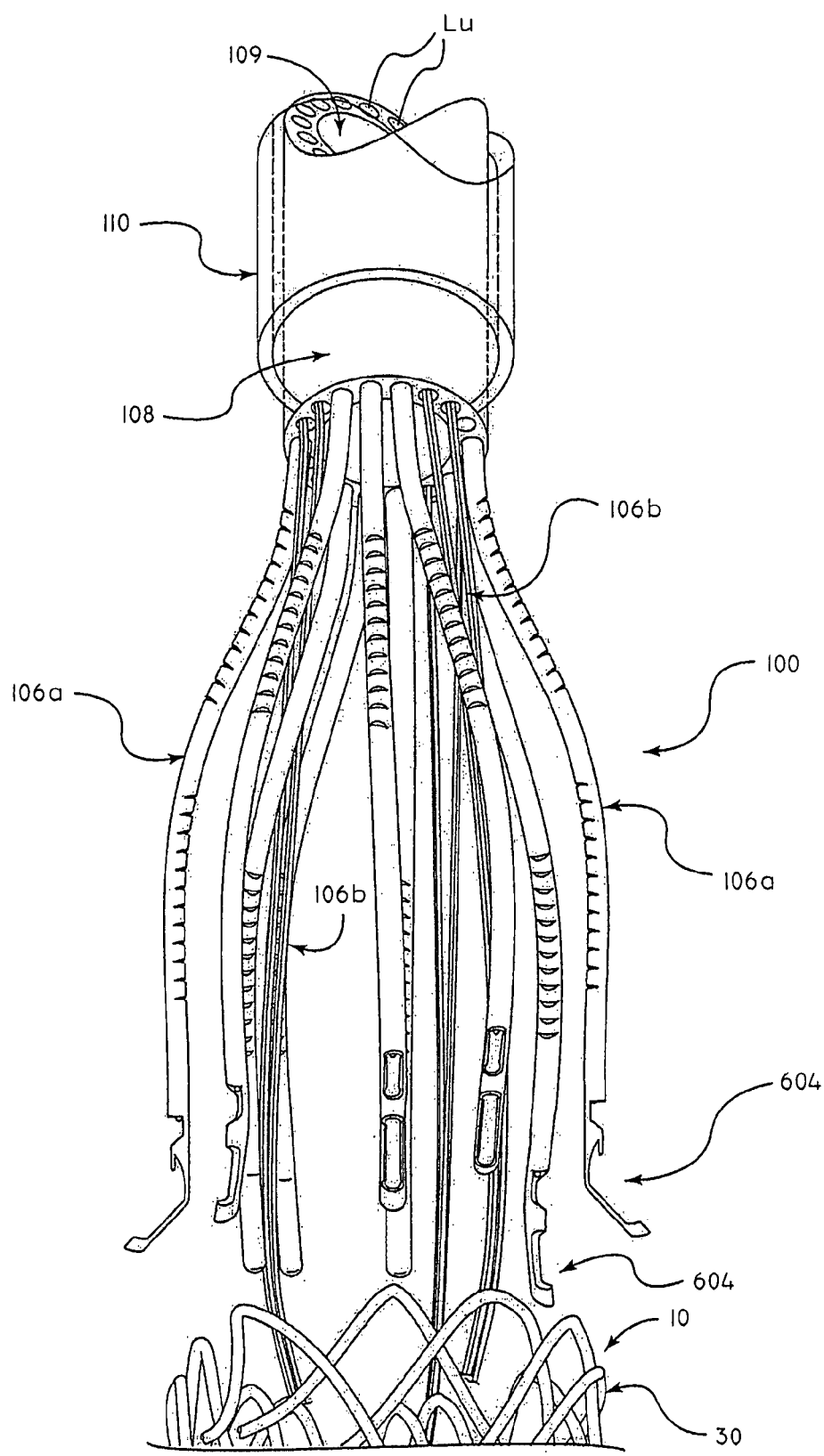

Referring now to FIG. 51, delivery system/deployment tool 100 is shown with a plurality of actuators 106a and actuators 106b for releasable attachment to anchor 30 of apparatus 10. In FIG. 51A, anchor actuation elements 106a are coupled to the anchor. In FIG. 51B, the elements are decoupled from the anchor.

Figure 52A:
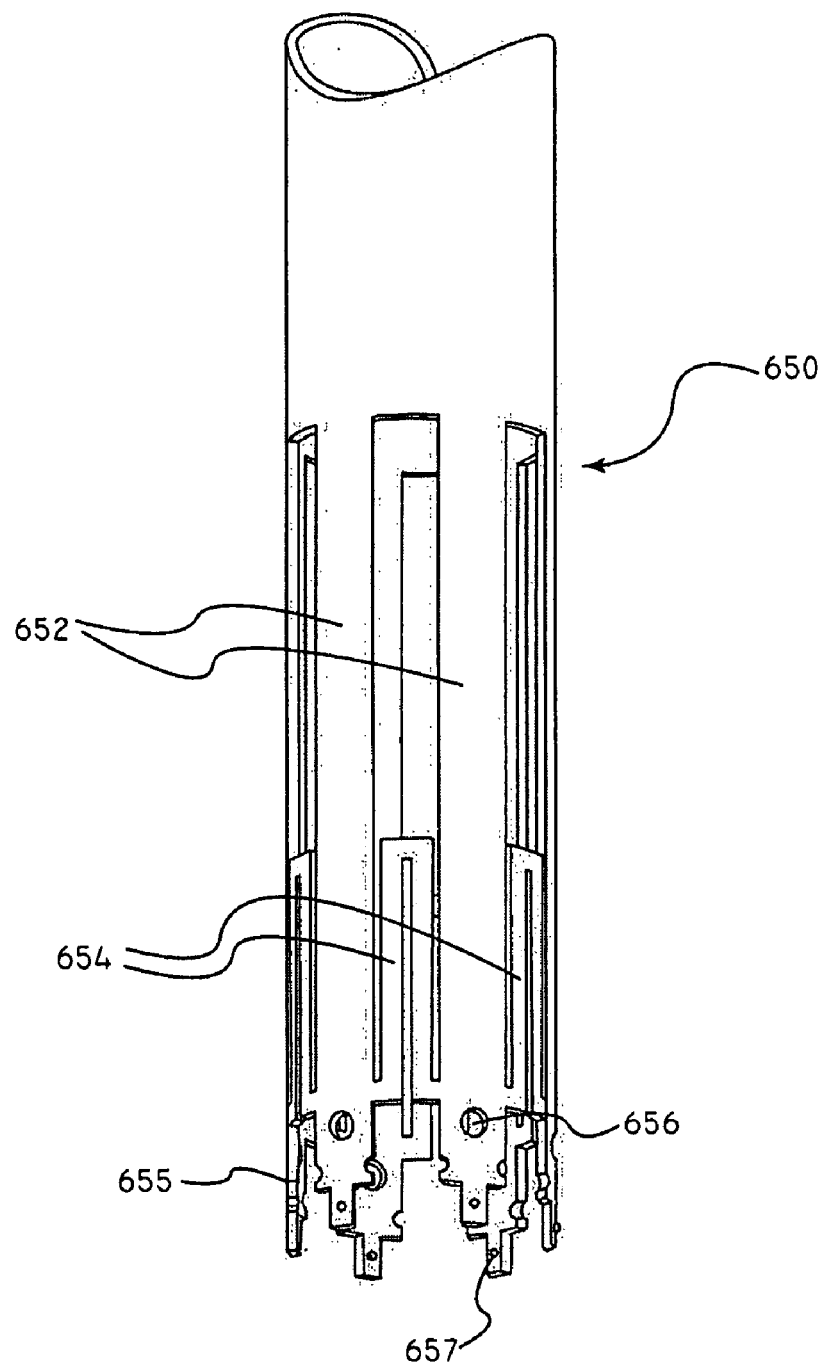
FIGS. 52A and 52B show a variation of the delivery system/deployment tool of FIGS. 50 and 51 wherein the actuators extend from a unitary structure.
Figure 52B:
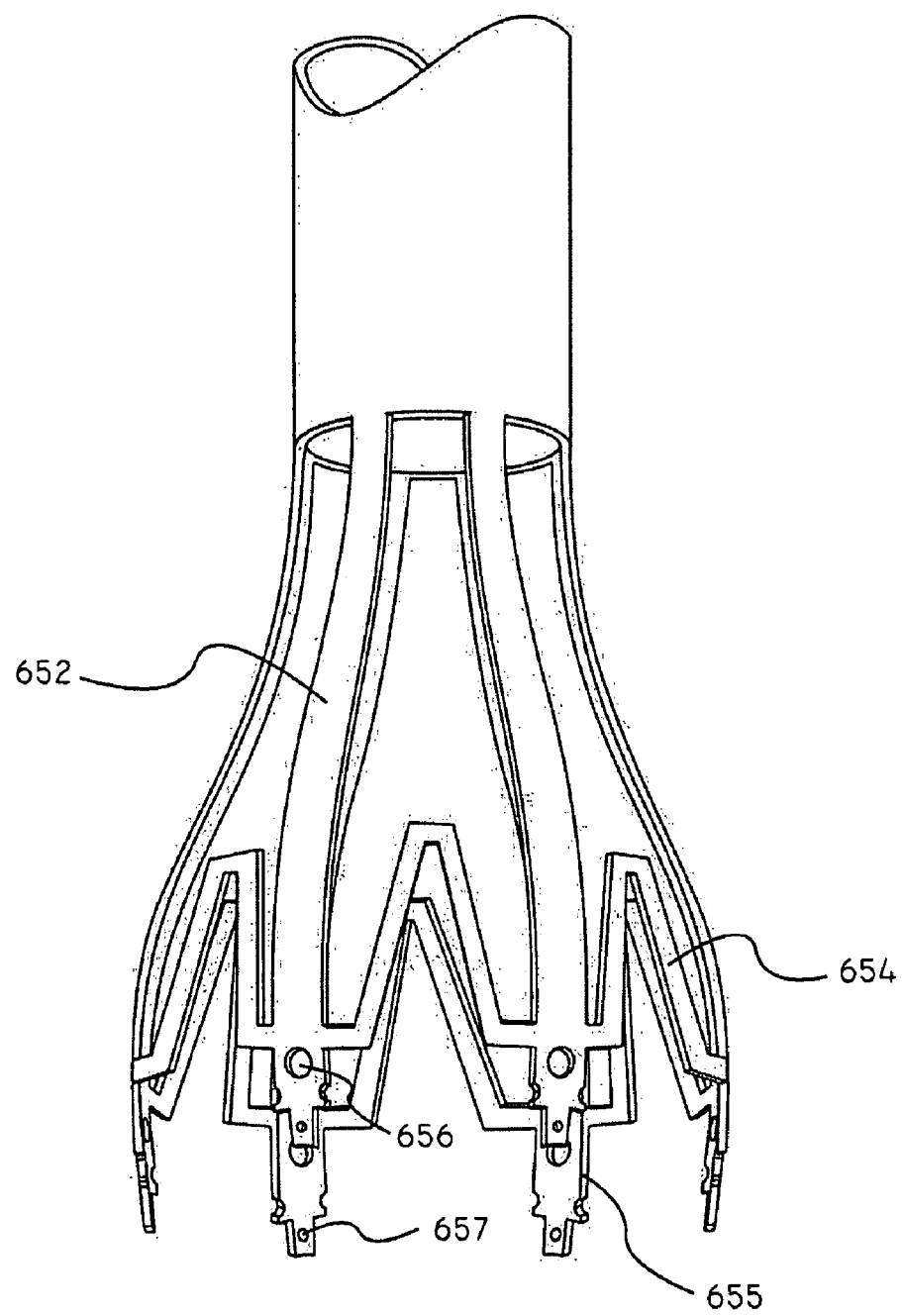

With reference now to FIG. 52, a variation of the delivery system/deployment tool of FIGS. 50 and 51 is described comprising a plurality of arms or actuators that extend from a unitary structure. Unitary structure 650, which may extend from a distal region of multi-lumen shaft 108, is preferably fabricated from a laser-cut tube. Structure 650 comprises a plurality of circumferentially disposed arms 652 that serve as actuators. Expansile elements 654 may be disposed between arms 652 and facilitate constraint of the arms radially outward or inward with respect to other arms as the anchor reshapes. FIG. 52A shows the arms in a radially collapsed configuration, and FIG. 52B shows the arms in a radially expanded configuration. Wrap portions 655 are adapted to wrap around the proximal portion of an anchor braid. Openings 656 and 657 are formed in wrap portions 655 to engage a release actuator, as described in embodiments above.

Figure 53A:
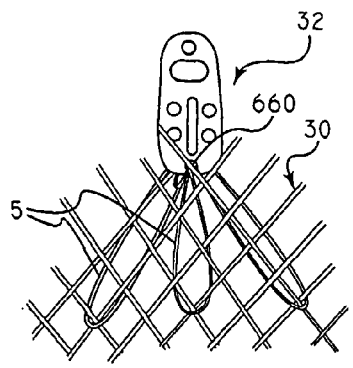
FIGS. 53A-53C show various ways to connect elements to the anchor of the replacement valve apparatus
Figure 53B:
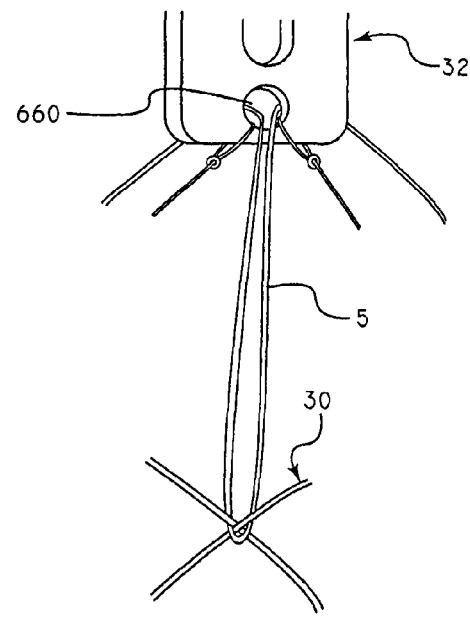
Figure 53C:
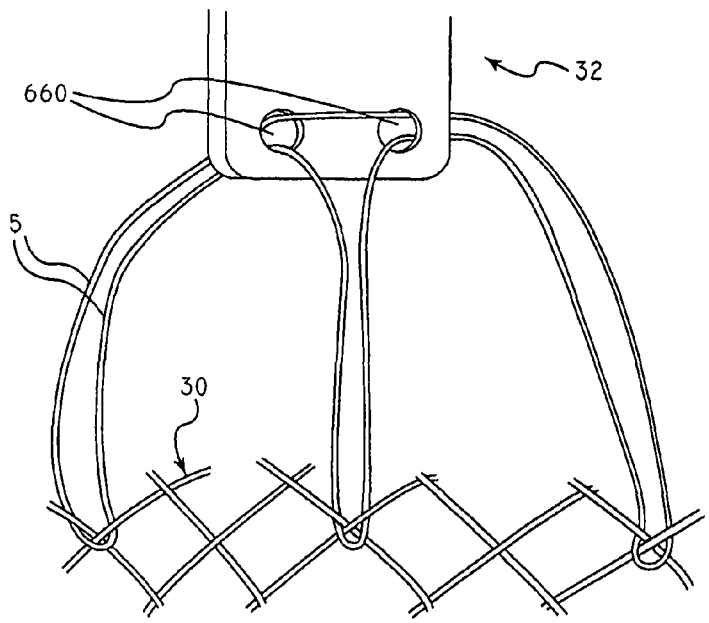

Referring now to FIG. 53, various ways to connect elements to the braid of anchor 30 of replacement valve apparatus 10 are described. In FIG. 53A, a post 32 having a single braid attachment hole 660 is attached to anchor 30 along three separate intersections of the braid via suture S. FIG. 53B provides a detail view of one exemplary technique for routing the suture between hole 660 and anchor 30. FIG. 53C illustrates a variation of the attachment, wherein post 32 comprises multiple braid attachment holes 660. As will be apparent, elements other than posts 32 may be attached to anchor 30 in the manner described, for example, anchor lock elements 34 may be attached in a similar manner.

Described below are alternatives for a releasable attachment mechanism for releasably attaching an implant, such as a braided anchor described herein, with a delivery system/deployment tool.

Figure 54:
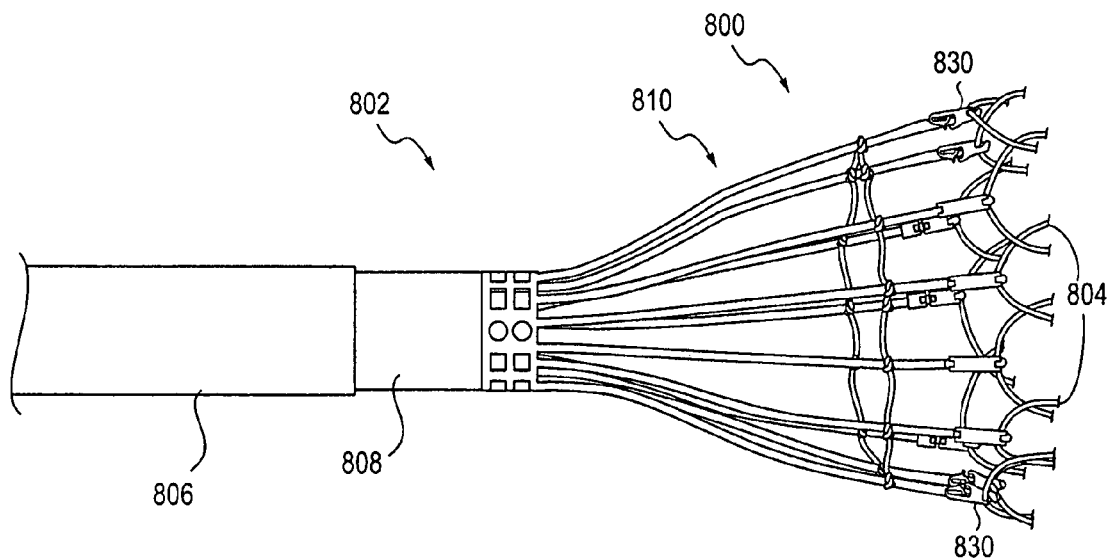
FIG. 54 shows an exemplary distal end of a delivery system capturing an exemplary medical implant.

FIG. 54 illustrates one embodiment of a distal end of a delivery system 802 comprising capturing system 800, catheter 808 (such as a multi-lumen catheter described herein), and outer sheath 806. Capturing system 800 is shown coupled to catheter 808, and is generally adapted to releasably hold, or capture, at least a portion of medical implant 804, for example, a braided anchor or other medical implant such as a stent. Capturing system 800 generally comprises a plurality of first actuatable elements 830, shown as collars, which are slidably interfaced with a plurality of second elements 810, shown as finger elements. Collars 830 are shown engaged with the finger elements 810 in a first position in which the collars 830 and the finger elements 810 interface to capture at least a portion of medical implant 804 and prevent it from being released from the delivery system 802.

Similar to the embodiments described above in, for example, FIG. 44A-FIG. 52, the first actuatable elements generally engage the second elements in a first configuration to capture the implant. The first actuatable element and the second element can, for example, create a space in which the medical implant is captured. In preferred embodiments the first actuatable element and the second element engage to define a space with a fixed shape, such as a cavity, in which a portion of the implant is disposed. A space with a fixed shape generally means a space whose perimeter is rigid or semi-rigid. The implant can be caged in the space, or situated in the space and not necessarily coupled to either the first or second elements. The implant can also snugly fit into the space, engaging either or both of the first and second elements. At least a portion of the captured implant can have a shape that is the same or substantially the same as either or both of a portion of the first and second elements. For example, a cube shaped portion of the implant may fit into a cube shaped cavity in the finger element. Or alternatively, the first and second elements may comprise shapes that together allow the implant to be captured between them. In all of these examples, which are not intended to be exhaustive, the implant would be captured.

Figure 55:
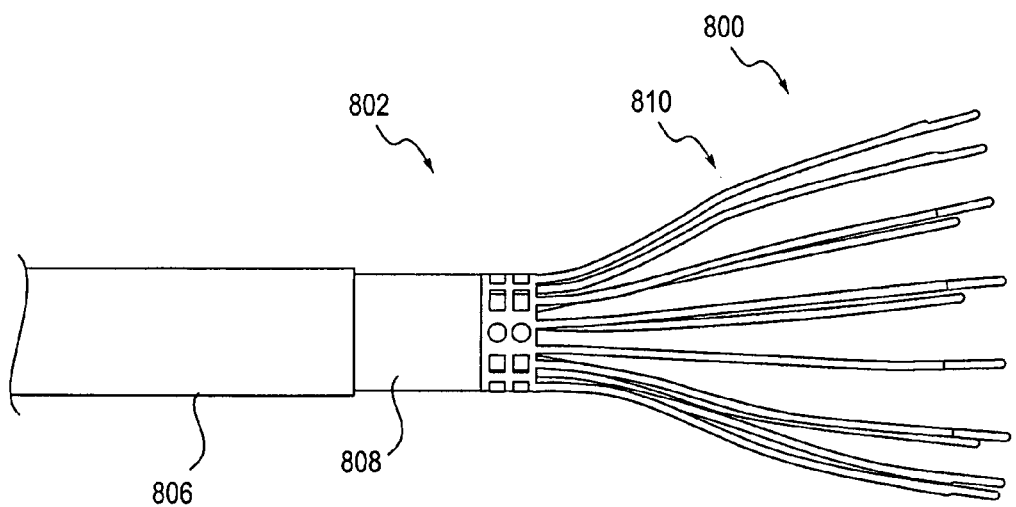
FIG. 55 shows exemplary finger elements.
Figure 56:
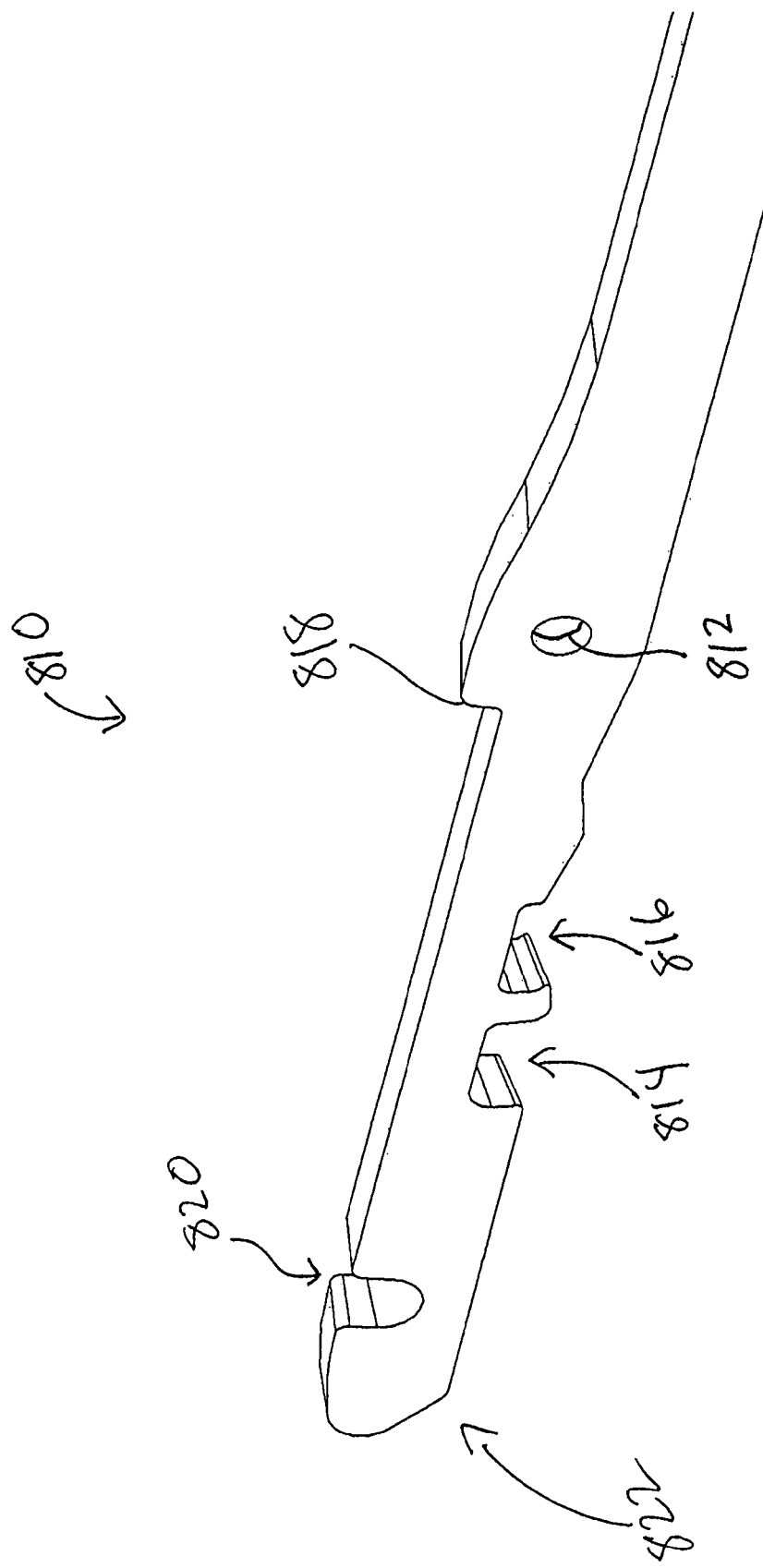
FIGS. 56 and 57 shows two embodiments of a portion of a finger element.

FIG. 55 shows an embodiment of capturing system 800 including finger elements 810 (other components not shown). FIG. 56 illustrate a section of a finger element 810 with distal end 822. Finger element 810 includes restraining element interface 812, implant interface 820, first stop element 814, second stop element 816, and end stop 818.

While the plurality of finger elements preferably include at least an implant interface, a first stop element, and an end stop, optional components includes a restraining element interface and a second stop element.

Figure 57:
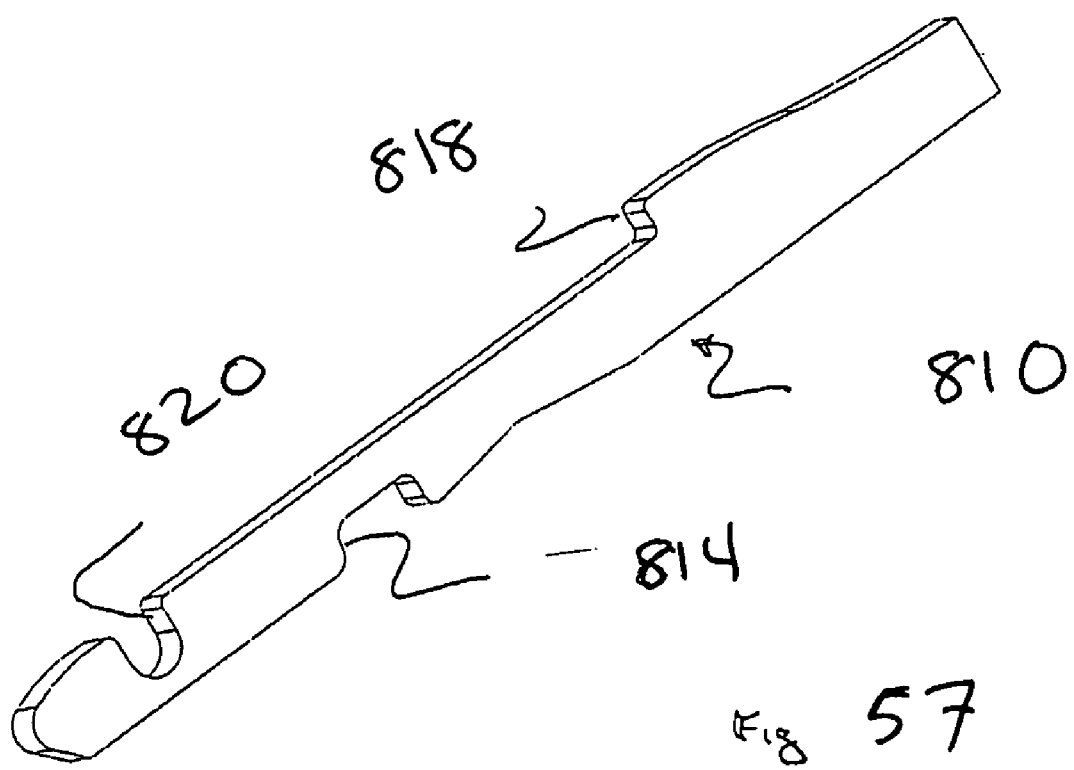

FIG. 57 shows an alternative embodiment of finger element 10 including implant interface 820, first stop element 814, and end stop 818. A collar interfacing with the finger element shown in FIG. 57 can be locked by engaging with the first stop element, but is not locked with the finger element in a second position as could a collar with the finger element shown in FIG. 56.

FIGS. 58 and 59 illustrate an embodiment of coupling system 800 in an expanded configuration, wherein the coupling system includes restraining device 882. Restraining device 882 engages with the restraining element interfaces 812 (as shown in, for example, FIG. 56) of the finger elements 810. Restraining device 882 is shown passing through the restraining element interfaces of the finger elements, thus limiting the coupling system's maximal expansion in a radial direction. The restraining device generally limits the expansion of the coupling system, and generally the finger elements, and prevents the coupling system from over expansion during delivery of the medical implant.

FIG. 58 illustrates coupling system 800 in an expanded configuration. The plurality of finger elements are fixed to coupler element 826, which incorporates hole features 828 which can facilitate bonding to the distal portion of catheter 808.

FIG. 60 shows an alternate embodiment of restraining device 882 wherein the restraining device does not pass through the plurality of finger elements but rather engages a restraining element interface on the exterior surface of the finger elements. Restraining device 882 could be adapted to expand and collapse in a controlled manner when the finger elements expand and/or collapse, using for example, a restraining device made from a shape memory material or a ratchet system.

Figure 61:
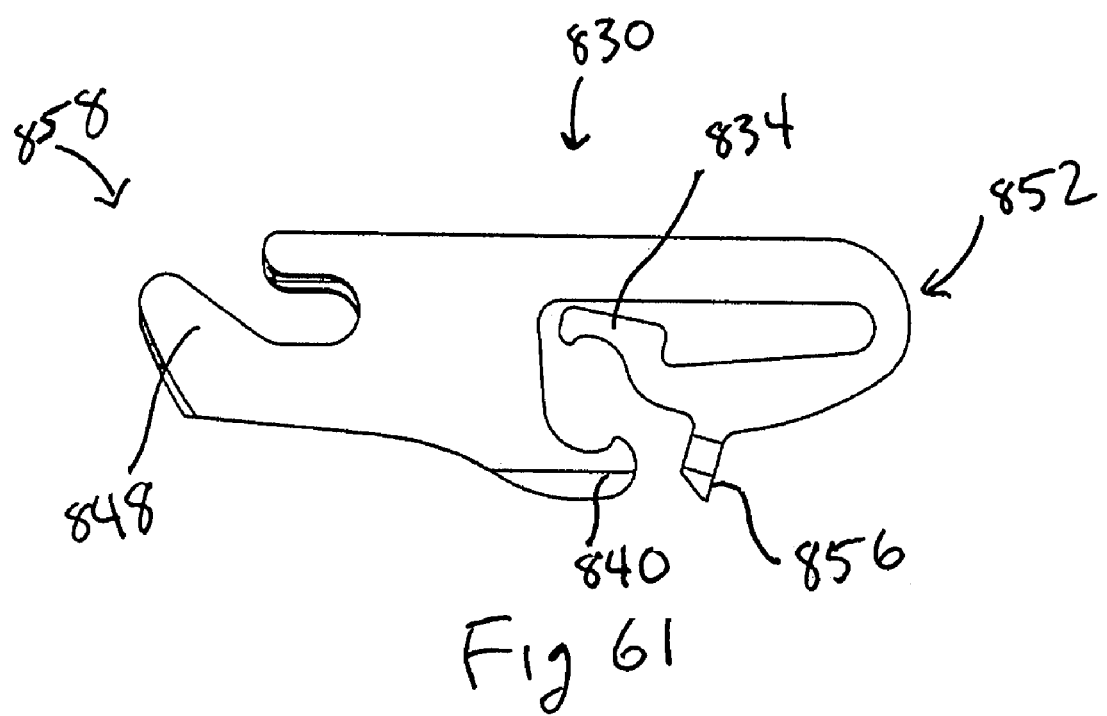
FIG. 61 shown an exemplary actuatable element of the present invention.
Figure 62:
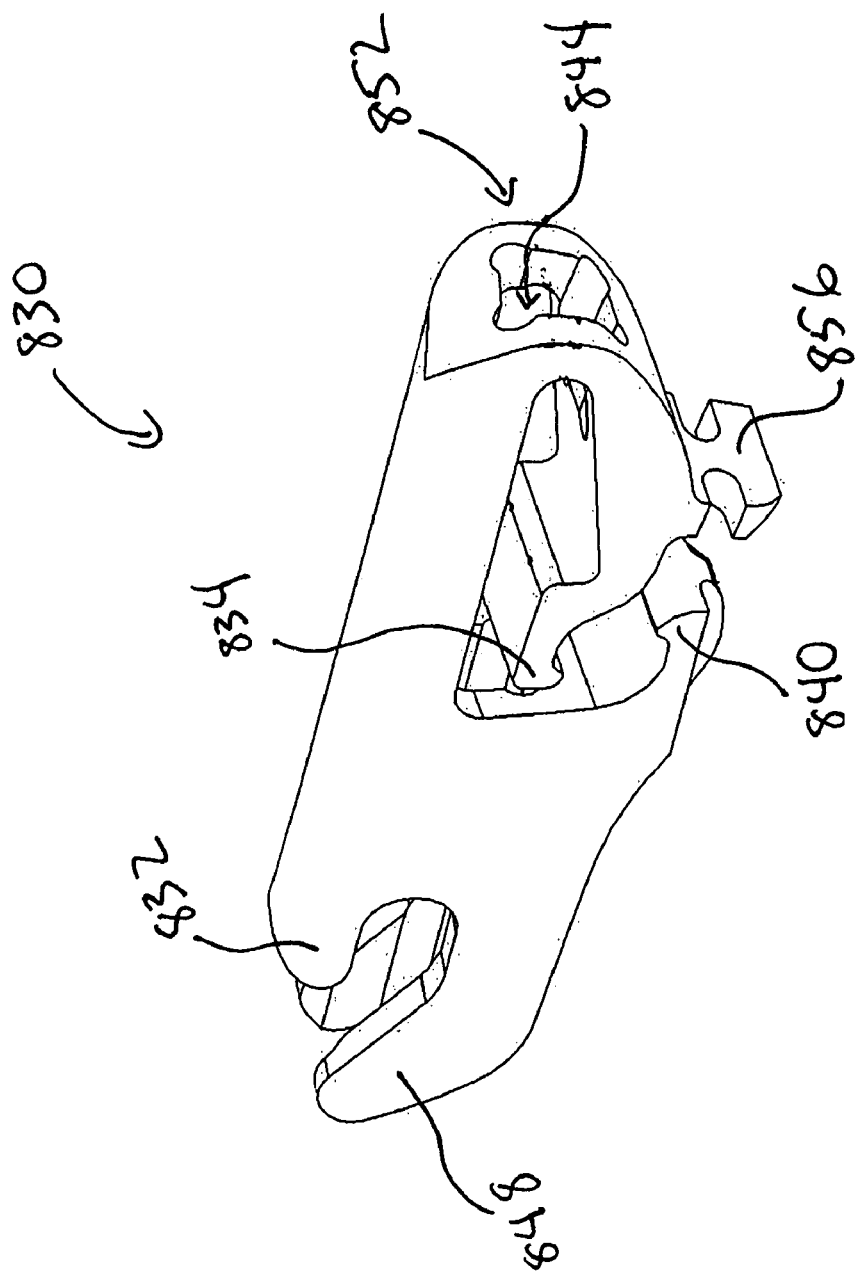
FIG. 62 is a perspective view of an exemplary actuatable element of the present invention.

FIGS. 61 and 62 show a side view and perspective view, respectively, of an exemplary collar 830 that can be used with the delivery systems and/or coupling systems described herein. Collar 830 includes a distal end 858 and includes lock element 834, lock stop element 840, hinge 852, through-hole 844, release element 856, and ejection element 848. Through-hole 844 is adapted to receive a finger element 810, which generally passes through the collar and engages with the interior surface of the collar (shown in FIGS. 10-13). The collar and finger element are adapted to slidably interface with one another.

Figure 63:
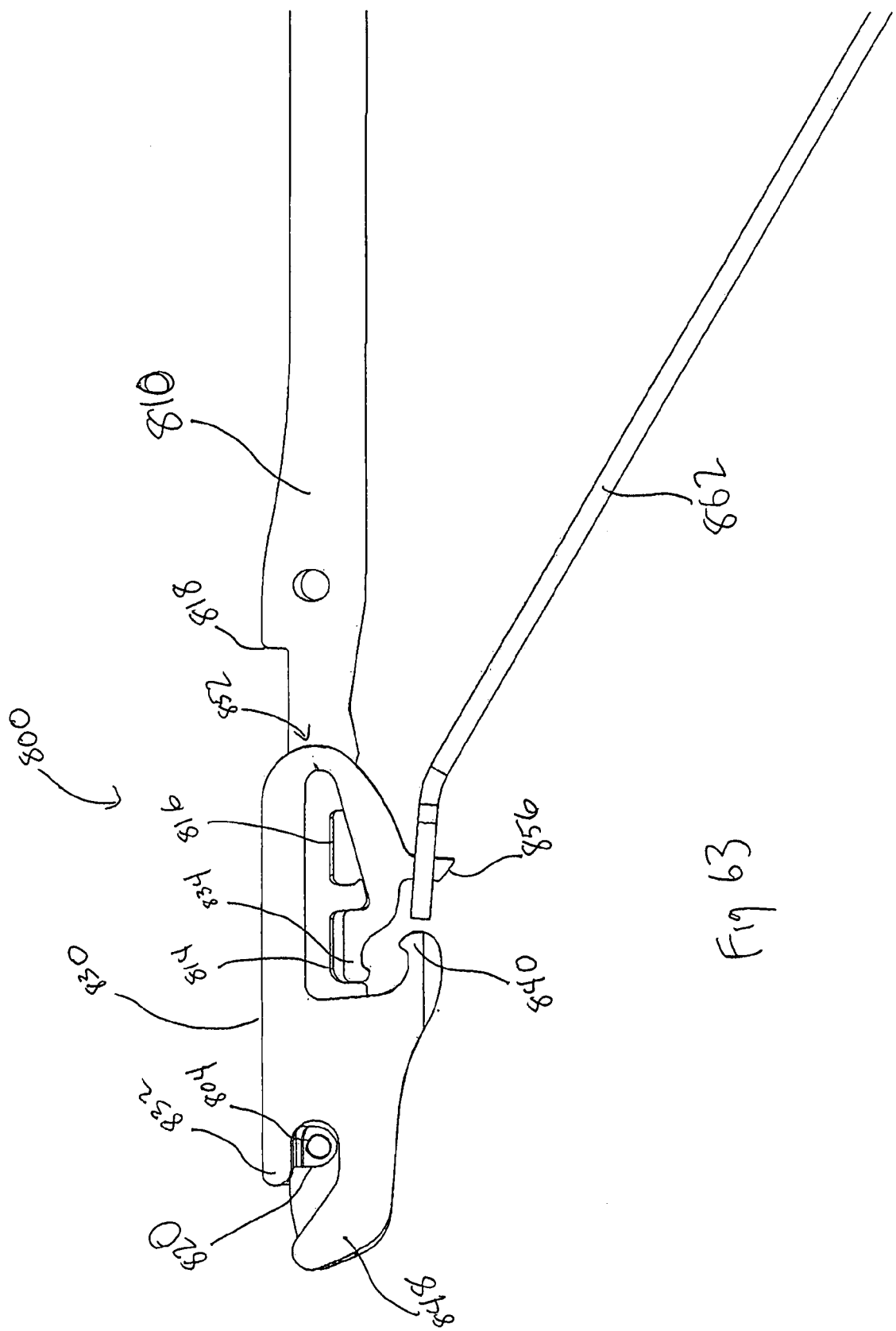
FIG. 63 is a side view of an exemplary capturing system in a first configuration with an exemplary medical implant captured within the system.

FIGS. 63-67 show one embodiment of the coupling system and an exemplary method of releasing at least a portion of a medical implant (not shown) from the coupling system. FIG. 63 shows collar 830 engaged with finger element 810 in a first position, preventing at least a portion of medical implant 804 from being released from the coupling system. Collar 830 is shown engaged with finger element 810 to prevent collar 830 from moving relative to the finger element 810. Collar 830 comprises lock element 834 adapted to engage with first stop element 814 of finger element 810, locking the collar in the first position. Locking the collar and finger element in the first position also prevents at least a portion of the implant from being released from the coupling system during delivery of the implant.

Also shown in FIGS. 63-67 is release actuator 862 adapted to engage release element 856 of collar 830. As described below, release actuator 862 is adapted to be delivered in the delivery device and can be adapted to be controlled by applying an actuating force using an actuator disposed outside of the patient, such as a control handle described herein.

Figure 64:
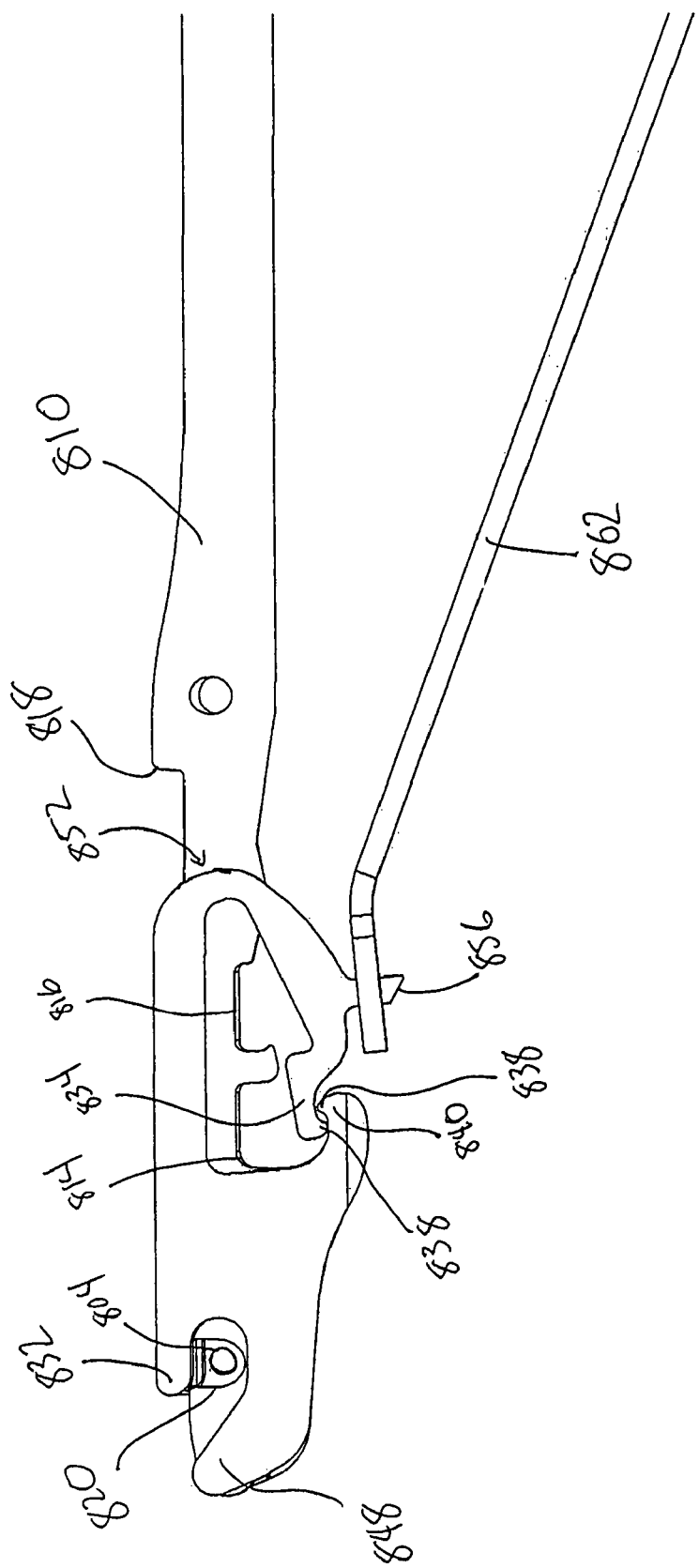
FIG. 64 shows an actuatable element unlocked from a second element.

FIG. 64 shows an embodiment of capturing system 800 wherein release actuator 862 has actuated release element 856 of collar 830 to unlock collar 830 from finger element 810. By actuating release element 856 of the collar, lock element 834 is moved from the position in FIG. 63 to an unlocked position in FIG. 64. Collar 830 also comprises lock stop element 840 which is adapted to interfere with and mate with lock element 834 to prevent further movement of lock element 834 after the lock element is moved from the locked position. Lock element 834 and lock stop element 840 each comprise a nub 838, each adapted to improve and/or enhance the engagement between lock element 834 and lock stop element 840. The nubs generally increase the force that may be applied between lock element 834 and lock stop element 840 before slipping occurs between the elements. This can assist in stabilizing the collar and preventing the lock element and lock stop element from slipping when an actuation force is applied to the collar to slide it between a first and second position. Hinge 852 of collar 830 deforms as release actuator 862 is actuated, allowing the collar to unlock from the finger element. Hinge 852 may have spring-like or memory properties such that it will have a tendency to return to the initial position.

Figure 65:
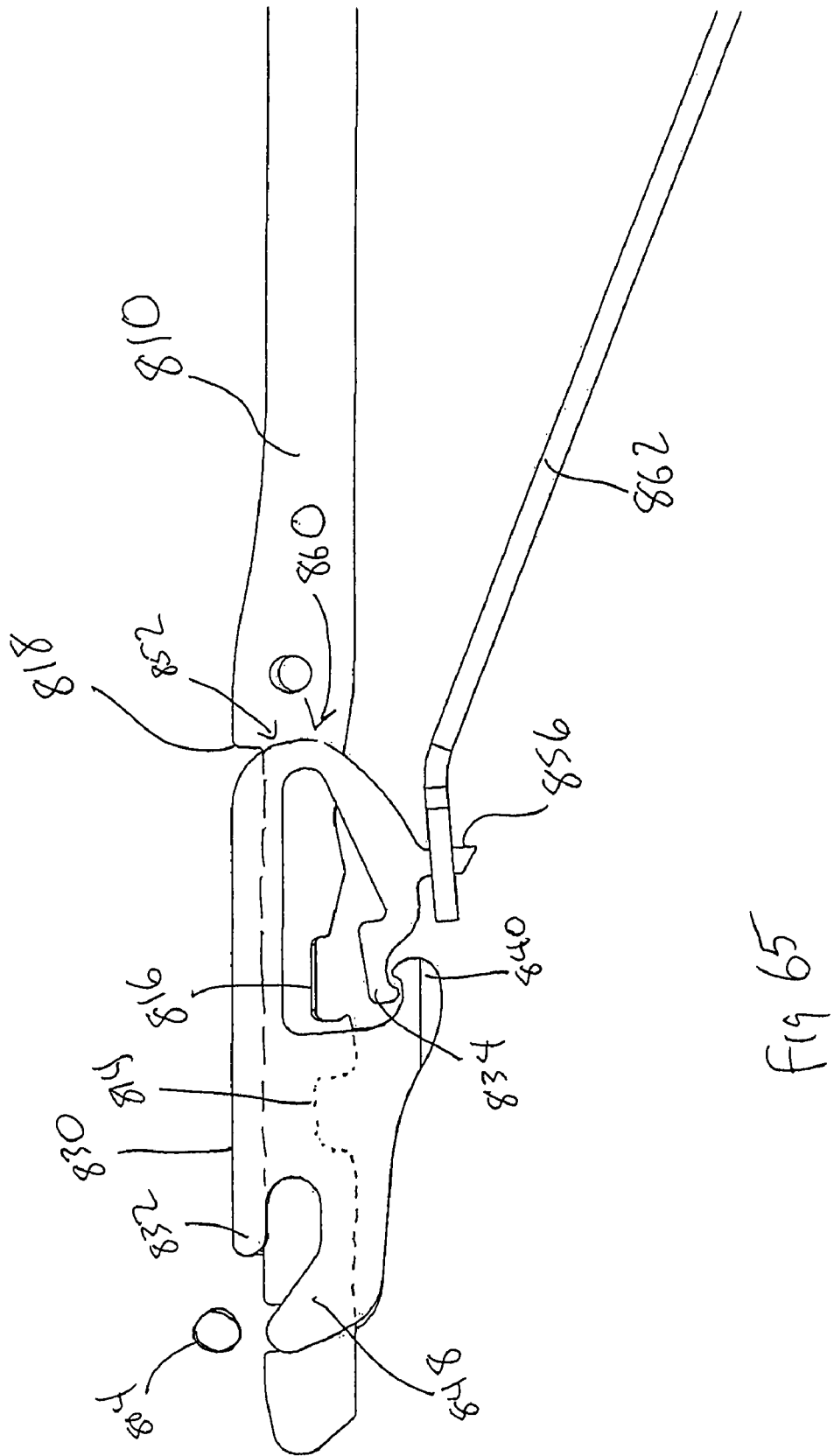
FIG. 65 shows a portion of a medical implant release from a delivery system.

After the lock element is disengaged from the collar, a proximally directed force on the actuator applies an actuation force to move the collar from the position shown in FIG. 64 to the position shown in FIG. 65. Moving the collar generally comprises sliding the collar along the finger as the interior surface of the collar engages the finger element.

The actuation force applied by the distal end of release actuator 862 to release element 856 is in a generally proximal direction, and can be applied from outside the patient using an actuator in the delivery system. The actuation force applied by the release actuator to the release element generally comprises both a proximally and radially inward force. The use of the term proximally directed force herein includes both a substantially proximally directed force and/or a radially inward force. The use of the term proximally directed also includes a proximally directed force applied from outside of the body which results in a proximally directed and/or radially inward force being applied to the actuatable elements. Based on the configuration of the engagement between the collar, finger element, and release actuator, however, the direction of the forces may vary, and may be substantially in one direction or the other.

As the collar moves through the positions shown in FIG. 64 to FIG. 65, the capture element 832, which is generally the portion of the collar preventing the medical implant from being released from the capturing system, is moved proximally, allowing medical implant 804 to be ejected from the implant interface 820. As the collar is moved to the position shown in FIG. 65, ejection element 848 engages with the medical implant 804 to eject the implant, such as a portion of a braided anchor, from the implant interface 820 of the finger element. The first actuatable elements are thus actuated to release the implant from the plurality of second elements.

The ejection element is shown with an angled surface approximately 45 degrees to the longitudinal axis of the finger element to ensure a controlled, smooth ejection and release of the implant from the coupling system. The angle shown is however, illustrative only and is not intended to be limiting, and the ejection element of the collar may be configured in other ways.

As shown in FIG. 65, end stop 818 engages with the proximal end of collar 860 to prevent the collar from further proximal movement. The end stop generally helps evenly distribute a proximally directed actuation force from outside of the patient to all of the collars in the delivery system. In general, a single proximally directed actuation force will be applied to the delivery device from outside of the patient. That force is preferably distributed to all (or, alternatively, to a select group of collars, for example, groups of collars may be actuated sequentially) of the collars as evenly as possible, such that all of the collars will move proximally to the second position (shown in FIG. 65) and eject their respective portions of the implant. Once a collar engages the end stop, the actuation force applied to that collar will generally be distributed to other collars which have not moved all the way to the end stop. This helps ensure an even distribution of force. The end stops thus help ensure the implant will be fully released from the capturing system.

Figure 66:
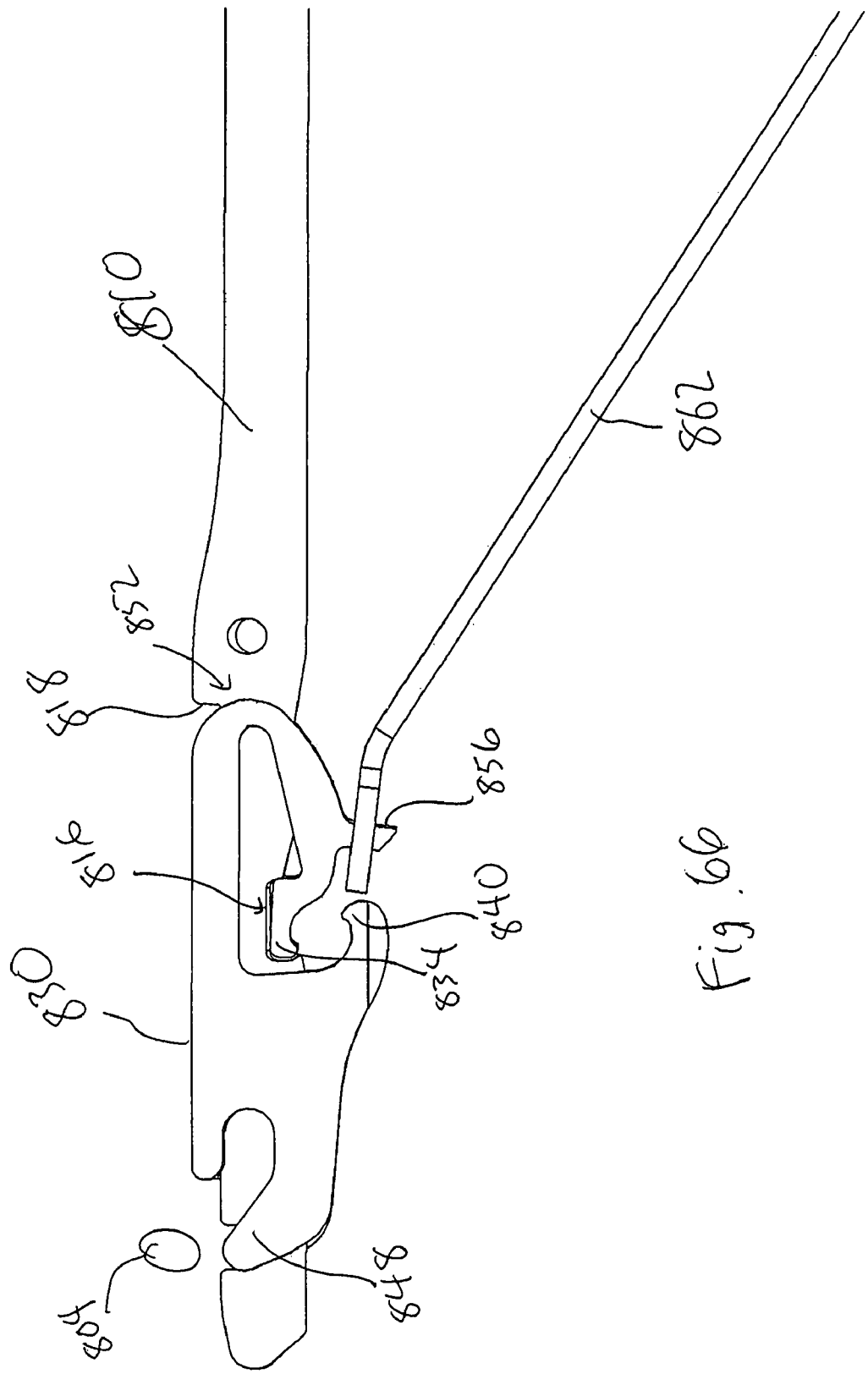
FIGS. 66 and 67 show an actuatable element in a second locked position relative to a second element.
Figure 67:
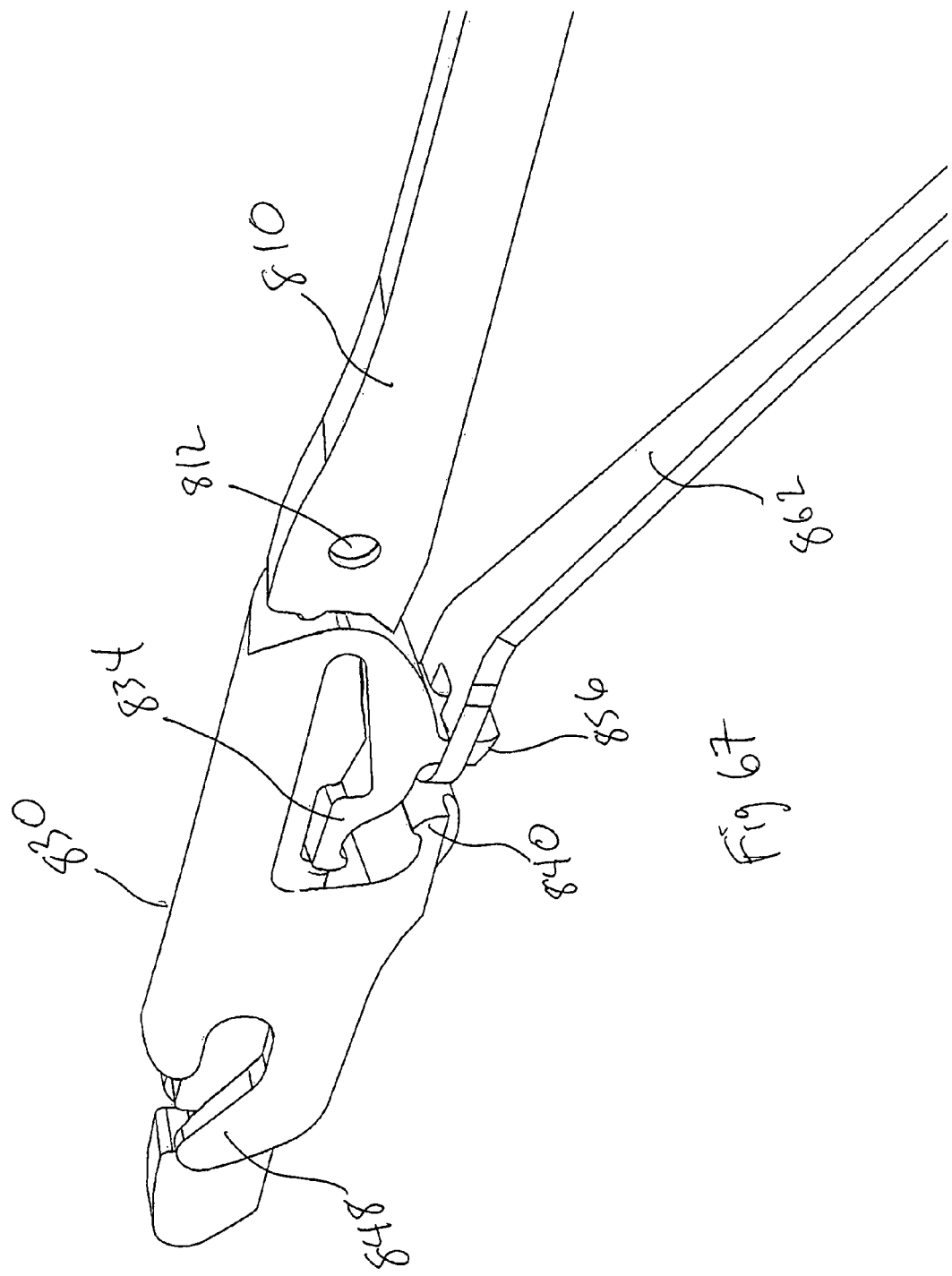

After the implant has been released from the capturing system (shown in FIG. 65), reducing, releasing, or discontinuing the proximally directed force on the release actuator causes hinge 852 to return to its initial position, causing lock element 834 to engage second stop element 816, again locking the collar with the finger element as shown in FIGS. 66 and 67. This locking step ensures that the collar does not move distally when actuation forces are no longer being applied to the release array.

Figure 68:
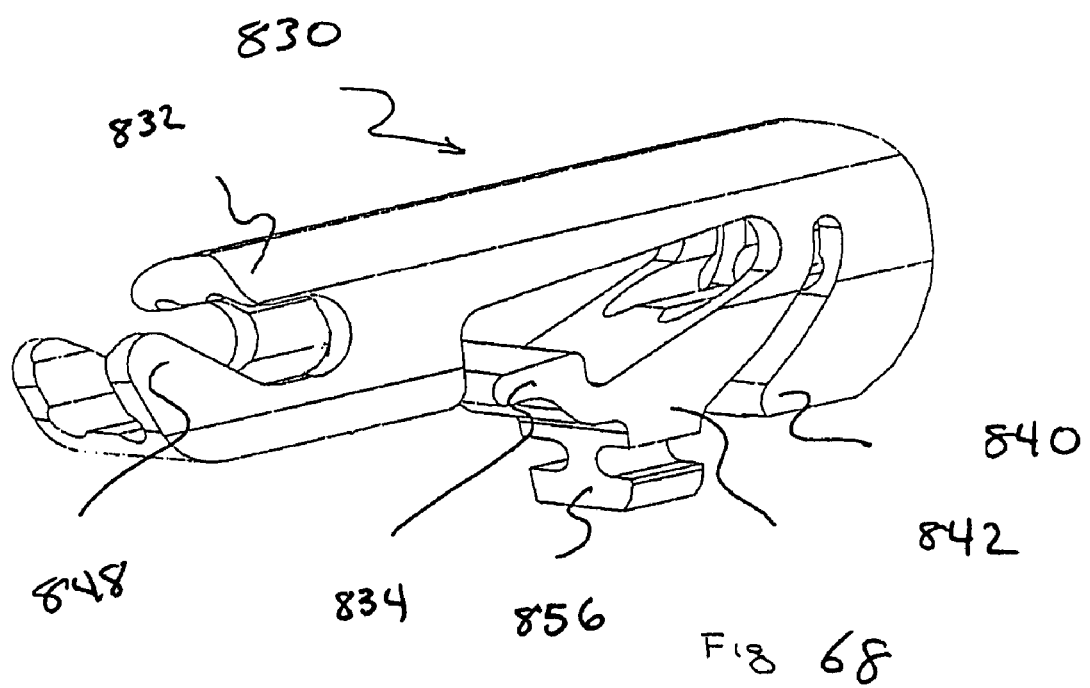
FIG. 68 is an alternate embodiment of an actuatable element.

After the collar is re-locked to the finger element, for example, as shown in FIG. 67, the capturing system can either be retracted into the outer sheath by applying a proximal force on the delivery catheter (such as the multi-lumen catheter) thereby forcing the capturing system to collapse from the expanded configuration to the collapsed configuration within the outer sheath, or the outer sheath can be moved distally over the catheter and capturing system. The delivery system can then be removed from the patient. FIG. 68 shows an alternate collar 830 incorporating an alternate implementation of the lock stop element 840 which interferes with lock element arm 842 as lock element 834 rotates away from the body of the collar when tension is applied via release element 856.

Figure 69:
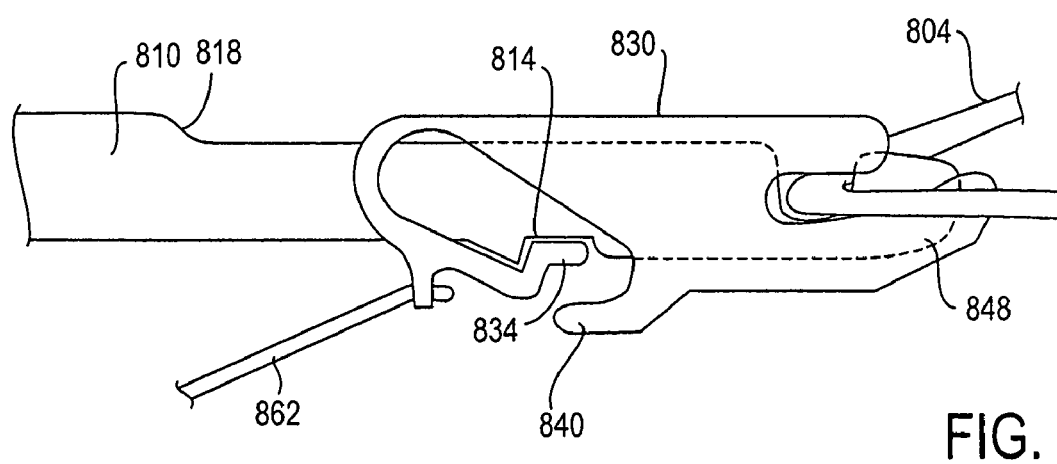
FIG. 69 shows an alternate configuration of a portion of a capturing system.

FIG. 69 shows a further alternate embodiment where lock element 834 of collar 830 is engaged with first stop element 814 of finger element 810, preventing proximal movement of the collar. When tension is applied to the release actuator, lock element 834 is released from first stop element 814, thereby allowing the collar to slide away from the distal end of the finger. Once the lock element is free, the collar is free to slide proximally thereby releasing the implant from implant retention element. As additional tension is applied to the release actuator, the lock element is constrained from over-rotation and possible failure by lock stop element 840. The collar is then retracted to end stop 818 after ejection element 848 has traversed the implant interface, ejecting the implant as is passes.

FIGS. 70 and 71 show an alternate embodiment in which the collar 830 hinge element is reconfigured as a continuous spring element. Lock element 834 is shown in FIG. 70 in a locked position engaged with first stop element 814. As tension is applied to the release actuator (not shown), the lock element is unlocked from the finger element 810 and allows the collar to slide proximally to the position in FIG. 71, where lock element 834 is locked with the finger element 810 in the second stop element 816.

The collar shown in FIGS. 70 and 71 can be made of a material, such as plastic, upon which an actuation force can be applied without undergoing substantial permanent deformation. However, the collars may be adapted for single use and then discarded, in which case the deformation of the collar may not be of critical importance. For example, it may be desirable only to avoid catastrophic failure during use.

Figure 73:
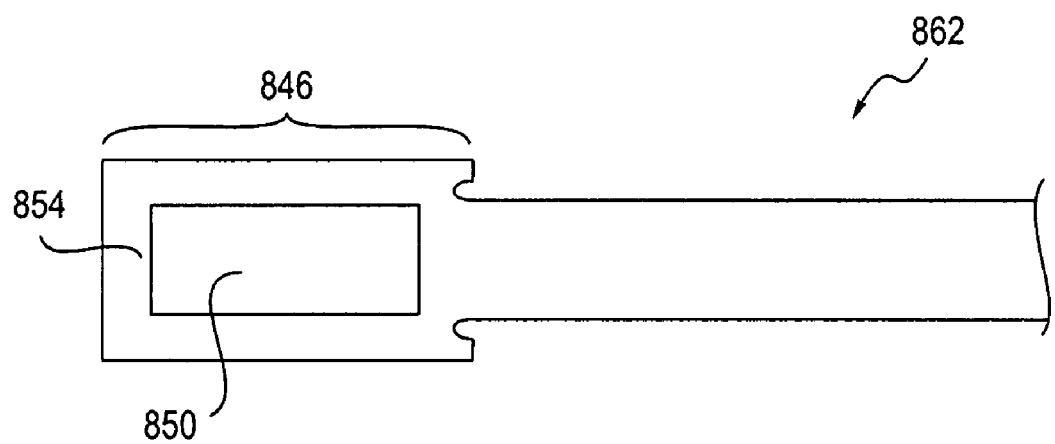
FIG. 73 shows a distal end of the release actuator from FIG. 72.
Figure 74:
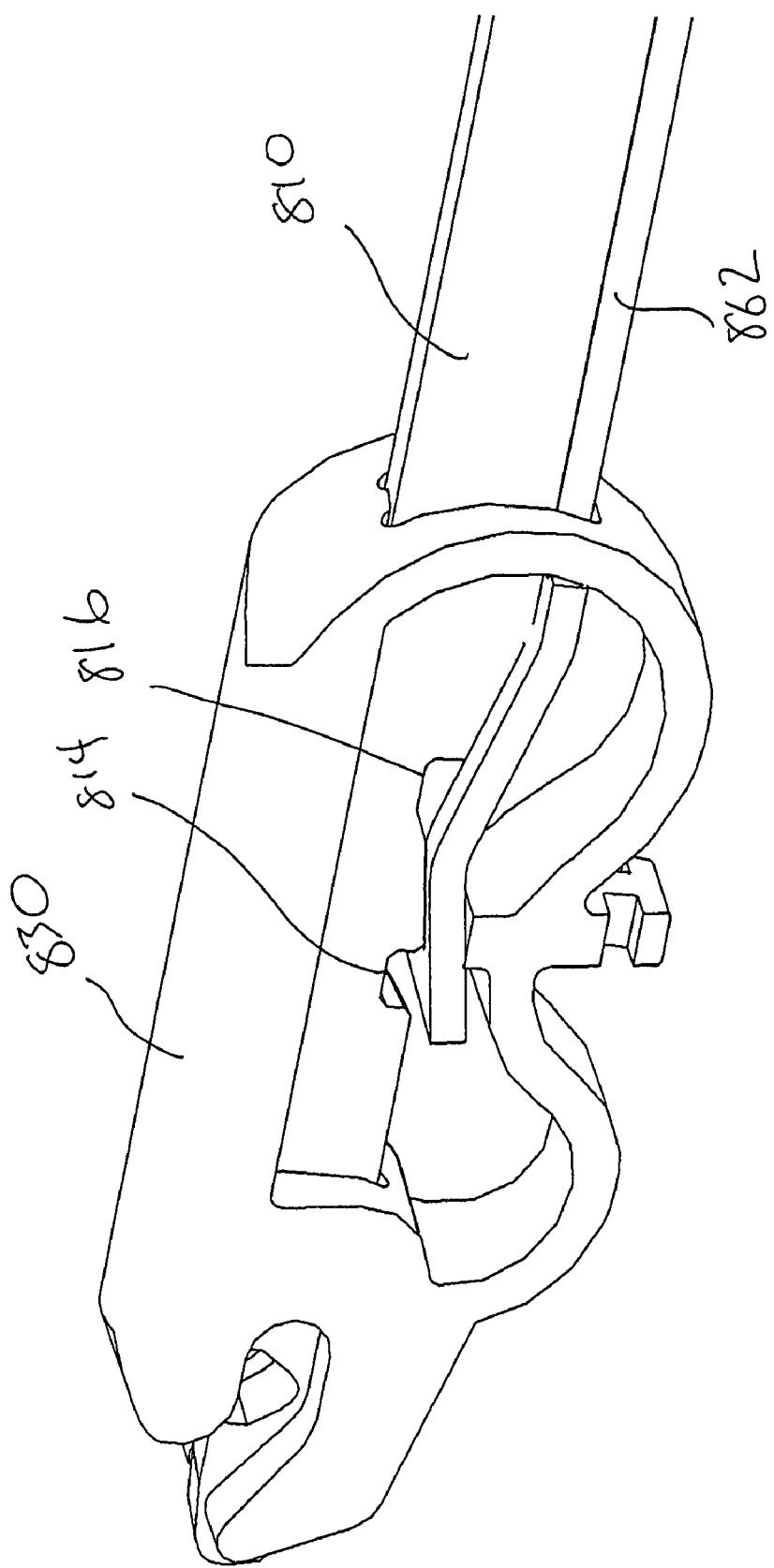
FIG. 74 shows a first actuatable element unlocked and in between a first and second positions.
Figure 75:
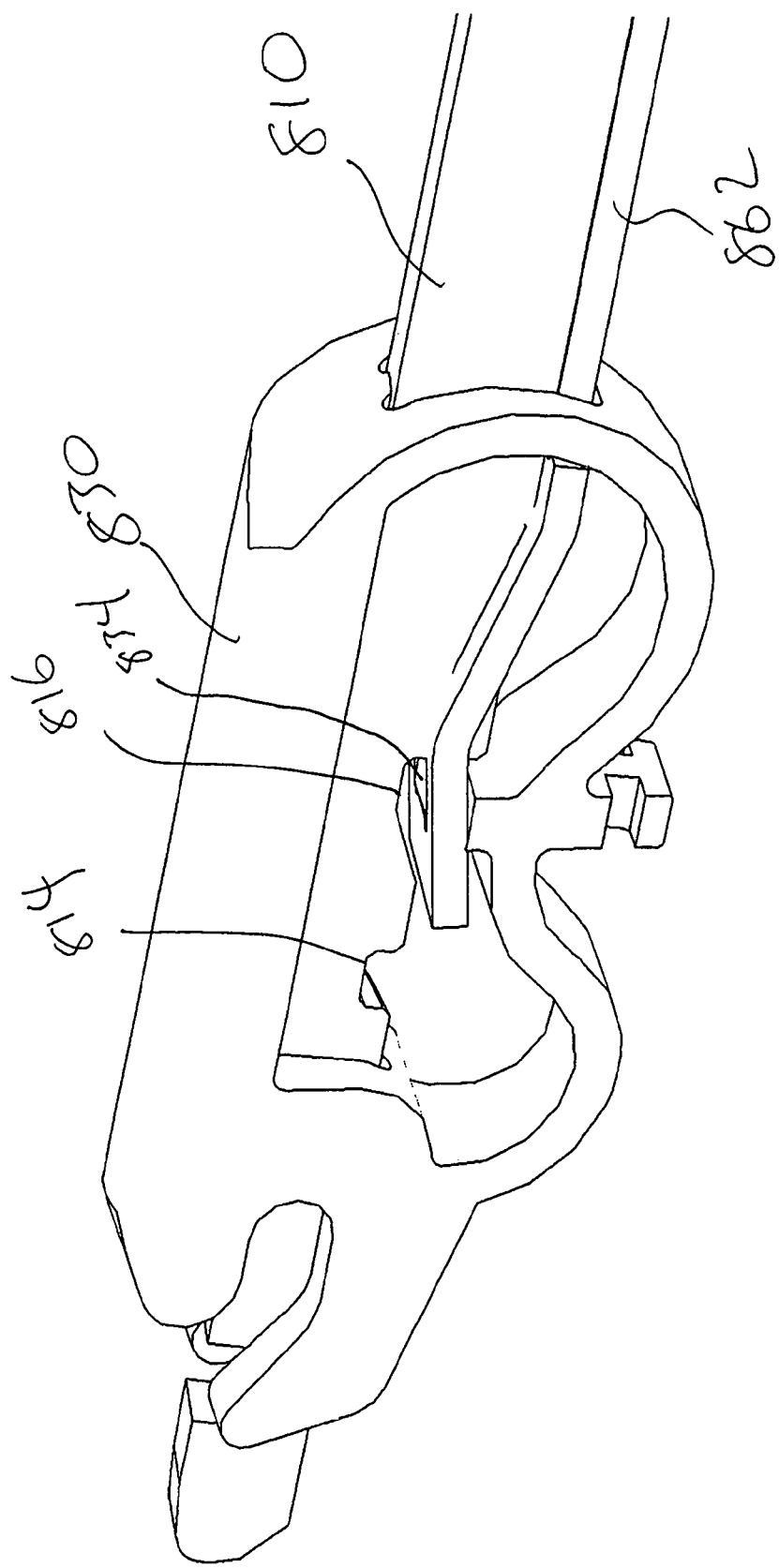
FIG. 75 shows a first actuatable element locked in a second position.

FIGS. 72-75 show an alternate embodiment in which the collar 830 hinge element is configured as a continuous spring-like device. In FIG. 72, release actuator 862 interfaces between finger element 810 and collar 830. The collar is shown in a locked position wherein the lock element 834 (not shown) engages the first stop element 814 of finger element 810. FIG. 73 shows a top view of release actuator 862, which comprises distal region 846, space 850, and wedge element 854. Release actuator 862 has a flexible curved distal region 846 comprising space 850 through which lock element 834 passes through when in a locked position. As a proximally directed force is applied to release actuator 862, release actuator 862 moves in a proximal direction, and wedge element 854 begins to wedge between finger element 810 and collar 830, forcing collar 830 in a downward direction indicated by the arrow in FIG. 72. This causes lock element 834 to disengage from the first stop element, unlocking the collar from the finger element. As a proximal force continues to be applied to the release actuator 862, wedge element 854 engages unlocked lock element 834 and/or a proximal edge of feature 846 engages the collar, either or both of which forces collar 830 to move in a proximal direction, sliding on finger element 810, as shown in FIG. 74. As shown in FIG. 75, when release actuator 862 pulls lock element 834 into the position shown, lock element 834 engages with second stop element 816, preventing further proximal movement of the collar. Similar to other embodiments described herein, ejection element 848 will eject the portion of the implant as it passes the implant interface of the finger element.

Figure 76:
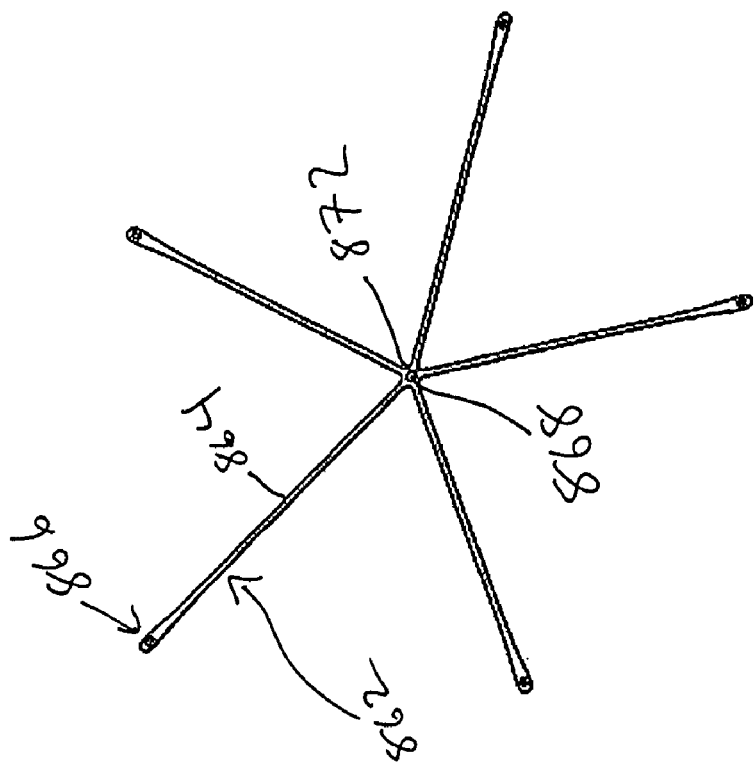
FIG. 76 shows an end view of an exemplary release actuator array.

FIG. 76 illustrates one embodiment of a release actuator array 870 comprising a plurality of release actuators 862 expanding radially outward from hub 872. The release actuators are shown integral with the hub as a single unit. Release actuators 862 comprise release actuator body 864 and release actuator distal end 866. Hub 872 has a bore through it to allow for placement of the array tool 874, as shown in FIG. 77.

FIG. 77 shows an embodiment of array tool 874 through the bore of the hub of the release actuator array. Array tool 874 includes an array tool distal end 876 which has a larger diameter than the body of the array tool so that when a proximal actuation force is applied to the array tool, array tool distal end 876 will engage with the hub of the release actuator hub and apply a proximally directed force to the array. As discussed above, the release actuator engages the collar, and as the proximally directed force is applied to the array, the release actuators apply a proximally directed force to the collar, and, for example, unlock the collar from the finger element or proximally pull the collar to a second position relative to the finger element.

In preferred embodiments, the number of release actuators in the capturing system is preferably the same as the number of collars in the capturing system, which is preferably the same as the number of finger elements. The capturing system may, however, include any number of finger elements (and therefore any number of collars and release actuators).

In some embodiments, however, there may be fewer collars (and similarly fewer release actuators) than finger elements. For example, there may be fifteen (15) finger elements, there may only be ten (10) collars, or even five (5) collars.

In some embodiments it may be advantageous to orient the finger elements in different configurations. For example, in FIGS. 54 and 55 the implant interfaces open in the radially outward direction. It may, however, be desirable for the implant interfaces to open in the radially inward direction. This may provide for a more secure delivery, depending on, for example, the type of implant being delivered. In further embodiments, some of the implant interfaces may open in the radially inward direction and some may open in the radially outward direction. In other embodiments, some fingers may not incorporate an implant interface. Any other configuration of fingers and collars may be used, however.

While there is 1 array with five release actuators shown in FIG. 77, FIG. 78 shows an embodiment wherein the capturing system includes three of the release actuator arrays 870 shown in FIG. 77. Each of the three arrays has five release actuators, and the capturing system includes fifteen release actuators.

The release actuators in each of the release actuator arrays shown in FIGS. 76-79 are spaced substantially equally from other another. In other words, the angle A (as shown in FIG. 77) between adjacent release actuators is the same. Thus, the angle between adjacent release actuators will generally be 360 divided by the number of release actuators in the array. There may, however, be any number of release actuators in each of the array, and the number of release actuators may differ from array to array. Any number of factors may influence the number of arrays used, or the number of release actuators per array, such as the type of medical implant being delivered.

FIG. 79 shows the arrays from FIG. 78 is a "stacked" position, such that a hub of an array engages with a hub of an adjacent array. The arrays may simply be disposed in the position shown in FIG. 79 without being fixed to one another, or the arrays may couple together with, for example, an adhesive, mechanical connection, or any other way to couple the arrays together. The arrays are preferably stacked together such that angles B (shown in FIG. 79) between adjacent release actuators accommodate the angles between the finger elements. FIG. 79 shows fifteen release actuators that are spaced substantially equally apart from an adjacent release actuator.

One advantage of a capturing system that uses multiple arrays is that the hub diameter is not as large as it would be if one array were used. For example, an array with fifteen release actuators would have a hub with a diameter larger than the diameters of the hubs shown in FIG. 79 (assuming the width of the release actuators remains the same). A hub with a smaller diameter potentially allows for a delivery system with a smaller diameter than would be necessary with a hub with a larger diameter. This can be advantageous when endovascularly delivering medical implants. In addition, as the diameter of the hub gets larger (as would occur with an increase in release actuators on an array), the hub may experience a greater peak stress during actuation of the array tool 874. As a proximal force is applied to the array tool, the array tool distal end engages the hub, forcing it in a proximal direction. Because the distal ends of the release actuators engage the collars (and cause an actuation force on the collars), the hub experiences a certain amount of stress, and as the diameter of the hub increases, the amount of stress on the portion of the hub with the greatest diameter can increase, and potentially result in hub failure. Thus, it may also be advantages to maintain the hub diameter(s) as small as possible.

The capturing systems described herein may have any number of release arrays, and there may be any number of release actuators in an array without departing from the invention. And while the arrays shown in FIGS. 77-79 comprise release actuators that are extending substantially perpendicular to the longitudinal axis of the array tool, the release actuators extend in a significantly more distal direction during delivery (collapsed in the catheter), and generally extend in a distal direction while the capturing system is in an expanded configuration (as shown in FIG. 59).

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. A delivery system adapted to deliver a medical implant though a body lumen and release the medical implant at a location within the body, the delivery system comprising:
   a plurality of actuatable elements releasably coupled to the medical implant during delivery of the medical implant, wherein the medical implant comprises an expandable element and a plurality of non-expandable elements secured to the expandable element, wherein the plurality of non-expandable elements are disposed on a proximal end of the expandable element such that the plurality of actuatable elements are releasably coupled to a proximal end of the medical implant, wherein the plurality of actuatable elements are releasably coupled to the plurality of non-expandable elements, and wherein the expandable element comprises a braided material comprising wire segments that slide with respect to one another as the expandable element expands from a delivery configuration.

2. The system of claim 1 wherein the plurality of actuatable elements are adapted to apply an actuatable force on the non-expandable elements to deploy the expandable element.

3. The system of claim 1 wherein the plurality of actuatable elements are rigid elements.

4. The system of claim 1 wherein the expandable element is an expandable anchor, and wherein the medical implant further comprises a plurality of leaflets.

5. The system of claim 1 wherein the plurality of actuatable components are adapted to remain releasably coupled to the plurality of non-expandable elements after the expandable element has been released from within an elongate delivery member.

6. A delivery system adapted to deliver a medical implant though a body lumen and release the medical implant at a location within the body, the delivery system comprising:
a plurality of actuatable elements releasably coupled to the medical implant during delivery of the medical implant, wherein the medical device comprises an expandable element and a plurality of non-expandable elements secured to the expandable element, wherein the plurality of non-expandable elements are disposed on a proximal end of the expandable element such that the plurality of actuatable elements are releasably coupled to a proximal end of the medical implant, wherein the plurality of actuatable elements are releasably coupled to the plurality of non-expandable elements, and wherein the plurality of actuatable elements are adapted to apply a distally directed actuation force on the proximal end of the medical implant to deploy the medical implant.

7. A delivery system adapted to deliver a medical implant though a body lumen and release the medical implant at a location within the body, the delivery system comprising:
a plurality of actuatable elements releasably coupled to the medical implant during delivery of the medical implant, wherein the medical device comprises an expandable element and a plurality of non-expandable elements secured to the expandable element, wherein the plurality of non-expandable elements are a first plurality of locking elements adapted to lockingly engage with a second plurality of locking elements to maintain the expandable element in an expanded configuration.

8. A delivery system adapted to deliver a medical implant though a body lumen and release the medical implant at a location within the body, the delivery system comprising:
a plurality of actuatable elements releasably coupled to the medical implant during delivery of the medical implant, wherein the medical device comprises an expandable element and a plurality of non-expandable elements secured to the expandable element, wherein the plurality of non-expandable elements are a first plurality of locking elements adapted to lockingly engage with a second plurality of locking elements to maintain the expandable element in an foreshortened configuration.

9. A replacement heart valve system, comprising
a replacement heart valve comprising an expandable element, a plurality of leaflets, and a plurality of non-expandable elements secured to a proximal portion of the expandable element;
a delivery system comprising a plurality of actuatable elements releasably coupled to the plurality of non-expandable elements, wherein the plurality of non-expandable elements are a first plurality of locking elements adapted to lockingly engage a second plurality of locking components that are disposed distal to the first plurality of locking elements to lock the expandable element in a foreshortened configuration.

10. The system of claim 9 wherein the plurality of actuation elements are adapted to remain releasably coupled to the plurality of non-expandable elements after the expandable element had been released from within an elongate delivery member.

\* \* \* \* \*